US 7,423,142 B2
Sep. 9, 2008

(12) United States Patent
Vornlocher

(54) COMPOSITIONS AND METHODS FOR INHIBITING EXPRESSION OF ANTI-APOPTOTIC GENES

(75) Inventor: Hans-Peter Vornlocher, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/229,183

(22) Filed: Sep. 15, 2005

(65) Prior Publication Data

US 2006/0084621 A1 Apr. 20, 2006

Related U.S. Application Data

(63) Continuation-in-part of application No. 10/941,663, filed on Sep. 15, 2004, which is a continuation-in-part of application No. 10/384,260, filed on Mar. 7, 2003, which is a continuation-in-part of application No. PCT/EP02/00151, filed on Jan. 9, 2002.

(30) Foreign Application Priority Data

Jan. 9, 2001 (DE) ............... 101 00 586.5

(51) Int. Cl.
*C07H 21/04* (2006.01)
*C07H 21/02* (2006.01)
*C12Q 1/68* (2006.01)
*C12N 15/85* (2006.01)
*C12N 15/86* (2006.01)

(52) U.S. Cl. .................. 536/24.5; 435/6; 435/325; 435/375; 536/23.1; 536/24.3

(58) Field of Classification Search .................. None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,212,295 A | 5/1993 | Cook | |
| 5,328,470 A | 7/1994 | Nabel et al. | |
| 5,521,302 A | 5/1996 | Cook | |
| 5,587,361 A | 12/1996 | Cook et al. | |
| 5,712,257 A | 1/1998 | Carter | |
| 5,998,203 A | 12/1999 | Matulic-Adamic et al. | |
| 6,054,299 A | 4/2000 | Conrad | |
| 6,127,533 A | 10/2000 | Cook et al. | |
| 6,166,197 A | 12/2000 | Cook et al. | |
| 6,271,358 B1 | 8/2001 | Manoharan et al. | |
| 6,423,489 B1 | 7/2002 | Anderson et al. | |
| 6,486,299 B1 | 11/2002 | Shimkets | |
| 6,506,559 B1 | 1/2003 | Fire et al. | |
| 2002/0086356 A1 | 7/2002 | Tuschl et al. | |
| 2002/0114784 A1 | 8/2002 | Li et al. | |
| 2002/0123034 A1 | 9/2002 | Canaani et al. | |
| 2002/0132346 A1 | 9/2002 | Cibelli | |
| 2002/0162126 A1 | 10/2002 | Beach et al. | |
| 2002/0173478 A1 | 11/2002 | Gerwitz | |
| 2003/0027783 A1 | 2/2003 | Zernicka-Goetz et al. | |
| 2003/0108923 A1 | 6/2003 | Tuschl et al. | |
| 2003/0125281 A1 | 7/2003 | Lewis et al. | |
| 2003/0143732 A1 | 7/2003 | Fosnaugh et al. | |
| 2003/0148341 A1 | 8/2003 | Sin et al. | |
| 2003/0157030 A1 | 8/2003 | Davis et al. | |
| 2003/0176671 A1 | 9/2003 | Reed et al. | |
| 2003/0180756 A1 | 9/2003 | Shi et al. | |
| 2003/0190635 A1 | 10/2003 | McSwiggen | |
| 2003/0198627 A1 | 10/2003 | Arts et al. | |
| 2004/0001811 A1 | 1/2004 | Kreutzer et al. | |
| 2004/0072779 A1 | 4/2004 | Kreutzer et al. | |

FOREIGN PATENT DOCUMENTS

| | | |
|---|---|---|
| DE | 199 56 568 A1 | 1/1999 |
| DE | 196 18 797 | 3/2000 |
| EP | 1 144 623 B1 | 8/2002 |
| EP | 1 230 375 B1 | 7/2005 |
| WO | WO 89/02468 | 3/1989 |
| WO | WO 89/05345 | 6/1989 |
| WO | WO 89/07136 | 8/1989 |

(Continued)

OTHER PUBLICATIONS

Elbashir et al., Functional anatomy of siRNAs for mediating efficient RNAi in Drosophila melanogaster embryo lysate, 2001, The EMBO Journal, vol. 20, No. 23, pp. 6877-6888.*

(Continued)

*Primary Examiner*—J. E. Angell
*Assistant Examiner*—Amy H. Bowman
(74) *Attorney, Agent, or Firm*—Lowrie, Lando & Anastasi LLP

(57) ABSTRACT

The present invention relates to a double-stranded ribonucleic acid (dsRNA) for inhibiting the expression of an anti-apoptotic gene, comprising an antisense strand having a nucleotide sequence which is less that 25 nucleotides in length and which is substantially complementary to at least a part of an apoptotic gene, such as a Bcl gene. The invention also relates to a pharmaceutical composition comprising the dsRNA together with a pharmaceutically acceptable carrier; methods for treating diseases caused by the expression of an anti-apoptotic gene using the pharmaceutical composition; and methods for inhibiting the expression of an anti-apoptotic gene in a cell.

5 Claims, 3 Drawing Sheets

FOREIGN PATENT DOCUMENTS

| WO | WO 92/07573 | | 5/1992 |
|---|---|---|---|
| WO | WO 92/19732 | | 11/1992 |
| WO | WO 94/01550 | A3 | 1/1994 |
| WO | WO 98/05770 | A1 | 2/1998 |
| WO | WO 98/53083 | | 11/1998 |
| WO | WO 99/15682 | | 4/1999 |
| WO | WO 99/32619 | | 7/1999 |
| WO | WO 99/19029 | | 9/1999 |
| WO | WO 99/53050 | | 10/1999 |
| WO | WO 99/54459 | * | 10/1999 |
| WO | WO 99/61631 | | 12/1999 |
| WO | WO 00/01846 | | 1/2000 |
| WO | WO 00/22113 | | 4/2000 |
| WO | WO 00/22114 | | 4/2000 |
| WO | WO 00/44495 | | 8/2000 |
| WO | WO 00/44895 | | 8/2000 |
| WO | WO 00/44914 | | 8/2000 |
| WO | WO 00/63364 | | 10/2000 |
| WO | WO 00/68374 | | 11/2000 |
| WO | WO 01/18197 | A1 | 3/2001 |
| WO | WO 01/29058 | A1 | 4/2001 |
| WO | WO 01/36646 | A1 | 5/2001 |
| WO | WO 01/42443 | A1 | 6/2001 |
| WO | WO 01/48183 | A2 | 7/2001 |
| WO | WO 03/035083 | A1 | 5/2003 |
| WO | WO 03/035868 | A1 | 5/2003 |
| WO | WO 03/035869 | A1 | 5/2003 |
| WO | WO 03/035870 | A1 | 5/2003 |
| WO | WO 03/035876 | A1 | 5/2003 |
| WO | WO 03/070283 | A2 | 8/2003 |
| WO | WO 03/070750 | A2 | 8/2003 |
| WO | WO 03/070969 | A2 | 8/2003 |
| WO | WO 03/070972 | A2 | 8/2003 |
| WO | WO 03/074654 | A2 | 9/2003 |
| WO | WO 03/080794 | A2 | 10/2003 |
| WO | WO 03/080807 | A2 | 10/2003 |
| WO | 2004027030 | | 4/2004 |
| WO | 2004045543 | | 6/2004 |
| WO | WO 2004/065601 | | 8/2004 |
| WO | WO 2005/012357 | | 2/2005 |

OTHER PUBLICATIONS

Hammond et al., Post-Transcriptional Gene Silencing by Double-Stranded RNA. 2001, Nature Reviews, Genetics, vol. 2, pp. 110-119.*

Ambros, "Dicing Up RNAs" *Science* 293:811-813 (2001).

Aoki et al., "RNA Interference May be More Potent than Antisense RNA in Human Cancer Cell Lines" *Clin. Exp. Pharm. Phys.* 30:96-102 (2003).

Armentano et al., "Expression of human factor IX in rabbit hepatocytes by retrovirus-mediated gene transfer: Potential for gene therapy of hemophilia B" *Proc. Natl. Acad. Sci. USA* 87:6141-6145 (1990).

Basbaum et al., "Focalized proteolysis: spatial and temporal regulation of extra cellular matrix degradation at the cell surface" *Curr. Opin. Cell Biol.* 8:731-738 (1996).

Bass, "Double-Stranded RNA as a Template for Gene Silencing" *Cell* 101:235-238 (2000).

Beck, "Unknotting the Complexities of Multidrug Resistance: The Involvement of DNA Topoisomerases in Drug Action and Resistance" *J. Natl. Cancer Inst.* 81:1683-1685 (1989).

Berkner et al., "Development of Adenovirus Vectors for the Expression of Heterologous Genes" *BioTechniques* 6(7):616-629 (1998).

Birkedal-Hansen et al., "Matrix Metalloproteinases: A Review" *Crit. Rev.Oral Biol. Med.* 4:197-250 (1993).

Boyd, "Invasion and metastasis" *Cancer Metastasis Rev.* 15(1):77-89 (1996).

Braasch et al., "Locked nucleic acid (LNA): fine-tuning the recognition of DNA and RNA" *Chem. Biol.* 8:1-7 (2001).

Brinckerhoff et al., "Matrix metalloproteinases: a tail of a frog that became a prince" *Nature Reviews* 3:207-214 (2002).

Bucchini et al., "Pancreatic Expression of Human Insulin Gene in Transgenic Mice" *PNAS USA* 83:2511-2515 (1986).

Caplen et al., "Specific Inhibition of Gene Expression by Small Double-Stranded RNAs in Invertebrate and Vertebrate Systems" *PNAS USA* 98(17):9742-9747 (2001).

Caplen, "A New Approach to the Inhibition of Gene Expression" *Trends in Biotech.* 20(2):49-51 (2002).

Chao et al., "BCL-2 Family: Regulators of Cell Death" *Annu. Rev. Immunol.* 16:395-419 (1998).

Chen et al., "Gene therapy for brain tumors: regression of experimental gliomas by adenovirus-mediated gene transfer in vivo" *Proc. Natl. Acad. Sci. USA* 91:3054-3057 (1994).

Childs et al., "The MDR Superfamily of Genes and Its Biological Implications" *Imp. Adv. Oncol.* 21-36 (1994).

Chowdhury et al., "Long-Term Improvement of Hypercholesterolemia After Ex Vivo Gene Therapy in LDLR-Deficient Rabbits" *Science* 254:1802-1805 (1991).

Cioca et al., "RNA interference is a functional pathway with therapeutic potential in human myeloid leukemia cell lines" *Cancer Gene Therapy* 10:125-133 (2003).

Cobaleda et al., "In vivo inhibition by a site-specific catalytic RNA subunit of Rnase P designed against the BCR-ABL oncogenic products: a novel approach for cancer treatment" *Blood* 95(3):731-737 (2000).

Cole et al., "Overexpression of a Transporter Gene in a Multidrug-Resistant Human Lung Cancer Cell Line" *Science* 258:1650-1654 (1992).

Cornetta et al., "Safety Issues Related to Retroviral-Mediated Gene Transfer in Humans" *Human Gene Therapy* 2 (1):5-10 (1991).

Cone et al., "High-efficiency gene transfer into mammalian cells: Generation of helper-free recombinant retrovirus with broad mammalian host range" *Proc. Natl. Acad. Sci. USA* 81:6349-6353 (1984).

Cook, "Medicinal chemistry of antisense oligonucleotides—future opportunities" *Anti-Cancer Drug Design* 6:585-607 (1991).

Couture et al., "Anti-gene therapy: the use of ribozymes to inhibit gene function" *Trends in Genetics* 12(12):510-515 (1996).

Crooke et al., "Pharmacokinetic Properties of Several Novel Oligonucleotide Analogs in Mice" *J. Pharmacol. Exp. Ther.* 277:923 (1996).

Dai et al., "Gene therapy via primary myoblasts: Long-term expression of factor IX protein following transplantation in vivo" *Proc. Natl. Acad. Sci. USA* 89:10892-10895 (1992).

Danos et al., "Safe and efficient generation of recombinant retroviruses with amphotropic and ecotropic host ranges" *Proc. Natl. Acad. Sci. USA* 85:6460-6464 (1988).

D'Ari, "Cycle-regulated genes and cell cycle regulation" *Bioassays* 23(7):563-565 (2001).

Delgardo et al., "The Uses and Properties of PEG-Linked Proteins" *Crit. Rev. Therap. Drug Carrier Sys.* 9 (3,4):249-304 (1992).

Docherty et al., "Nutrient regulation of insulin gene expression" *FASEB J.* 8:20-27 (1994).

Doench et al., "siRNAs can function as miRNAs" *Genes & Development* 17:438-442 (2003).

Donzé et al., "RNA interference in mammalian cells using siRNAs synthesized with T7 RNA Polymerase" *Nucleic Acids Research* 30(10):e46 (2002).

Downward et al., "Identification of a nucleotide exchange-promoting activity for p21$^{ras}$" *PNAS USA* 87:5998-6002 (1990).

Eder "Monitoring of BCR-ABL expression using real-time RT-PCR in CML after bone marrow or peripheral blood stem cell transplantation" et al., *Leukemia* 13:1383-1389 (1999).

Eglitis et al., "Gene Expression in Mice After High Efficiency Retroviral-Mediated Gene Transfer" *Science* 230:1395-1398 (1985).

Elbashir et al., "Duplexes of 21-nucleotide RNAs mediate RNA interference in cultured mammalian cells" *Nature* 41:494-498 (2001).

Elbashir et al., "Functional anatomy of siRNAs for mediating efficient RNAi in *Drosophila melanogaster* embryo lysate" *EMBO J.* 20(23):6877-6888 (2001).

Elbashir et al., "RNA interference is mediated by 21- and 22-nucleotide RNAs" *Genes and Development* 15:188-200 (2001).

Eriksson et al., "Establishment and characterization of mouse stain (TLL) that spontaneously develops T-cell lymphomas/leukemia" *Exp. Hematol.* 27(4):682-688 (1999).

Fan et al., "Reversal of Multidrug Resistance in Cancer", ed. Kellen, CRC, Boca Raton, FL, 93-125.

Ferry et al., "Retroviral-mediated gene transfer into hepatocytes in vivo" *Proc. Natl. Acad. Sci. USA* 88:8377-8381 (1991).

Fire et al., "Potent specific genetic interference by double-stranded RNA in *Caenorhabditis elegans*" *Nature* 391:806-811 (1998).

Fire,"RNA-triggered gene silencing" *TIG* 15(9):358-363 (1999).

Fotedar et al., "Apoptosis and the cell cycle" *Prog. Cell Cycle Res.* 2:147-163 (1996).

Gassmann et al., "Maintenance of an extrachomosomal plasmid vector in mouse embryonic stem cells" *PNAS USA* 92:1292 (1995).

Gautschi et al., "Activity of a Novel bcl-2/bcl-xL-Bispecific Antisense Oligonucleotide Against Tumors of Diverse Histologic Origins" *J. Natl. Cancer Institute* 93(6):463-471 (2001).

GenBank Accession No. M13994, "Human B-cell leukemia/lymphoma 2 (bcl-2) proto-oncogene mRNA encoding bcl-2-beta protein," Oct. 31, 1994.

GenBank Accession No. M13995, "Human B-cell leukemia/lymphoma 2 (bcl-2) proto-oncogene mRNA encoding bcl-2-beta protein," Oct. 31, 1994.

GenBank Accession No. U55763, "Cloning vector pEGFP-C1, complete sequence, enhanced green fluorescent protein (egfp) and neomycin phosphottransferase genes," Jun. 15, 1996.

Gibbs et al., "Purification of ras GTPase activating protein from bovine brain" *PNAS USA* 85:5026-5030 (1988).

Hamm et al., "Incorporation of 2'-Deoxy-2'mercaptocytidine into Oligonucleotides via Phosphoramidite Chemisty" *J. Org. Chem.* 62:3415-3420 (1997).

Hammond et al., "An RNA-directed nuclease mediates post-transcriptional gene silencing in *Drosophila* cells" *Nature* 404:293-296 (2000).

Hanahan et al., "The Hallmarks of Cancer" *Cell* 100:57-70 (2000).

Harborth et al., "Identification of essential genes in cultured mammalian cells using small interfering RNAs" *J. Cell Science* 114(24):4557-4565 (2001).

Harris et al., "The Eµ-*myc* Transgenic Mouse A Model for High-incidence Spontaneous Lymphoma and Leukemia of Early B Cells" *J. Exp. Med.* 167(2):353-371 (1988).

Holen et al., "Positional effects of short interfering RNAs targeting the human coagulation trigger Tissue Factor" *Nucleic Acids Research* 30(8):1757-1766 (2002)

Hsu et al., "Immunogenicity of Recombinant Adenovirus-Respiratory Syncytial Virus Vaccines with Adenovirus Types 4, 5, and 7 Vectors in Dogs and a Chimpanzee" *J. Infectious Disease* 166:769-775 (1992).

Huber et al., "Retroviral-mediated gene therapy for the treatment of hepatocellular carcinoma: An innovative approach for cancer therapy" *Proc. Natl. Acad. Sci. USA* 88:8039-8043 (1991).

Hwu et al., "Functional and Molecular Characterization of Tumor-Infiltrating Lymphocytes Transduced with Tumor Necrosis Factor-α cDNA for the Gene Therapy of Cancer in Humans" *J. Immunol.* 150(9):4104-4115 (1993).

James et al., "The Therapeutic Potential of Ribozymes" *Blood* 91(2):371-382(1998).

Kabanov et al., "A new class of antivirals: antisense oligonucleotides combined with a hydrophobic substituent effectively inhibit influenza virus reproduction and synthesis of virus-specific proteins in MDCK cells" *FEBS Lett.* 259(2):327-330 (1990).

Kay et al., "Hepatic Gene Therapy: Persistent Expression of Human α1-Antitrypsin in Mice after Direct Gene Delivery In Vivo" *Human Gene Therapy* 3:641-647 (1992).

Koshkin et al., "LNA (Locked Nucleic Acids)" Synthesis of the Adenine, Cytosine, Guanine, 5-Methylcytosine, Thymine and Uracil Bicyclonucleoside Monomers, Oligomerisation, and Unprecedented Nucleic Acid recognition *Tetrahedron* 54:3607-3630 (1998).

Kovalchuk et al., "Burkitt Lymphoma in the Mouse" *J. Exp. Med.* 192(8):1183-1190 (2000).

Krepela, "Cysteine proteinases in tumor cell growth and apoptosis" *Neoplasma* 48(5):332-349 (2001).

Letsinger et al., "Cholesteryl-conjugated oligonucleotides: Synthesis, properties, and activity as inhibitors of replication of human immunodeficiency virus in cell culture" *PNAS USA* 86:6553-6556 (1989).

Lewis et al., "Efficient delivery of siRNA for inhibition of gene expression in postnatal mice" *Nature Genetics* 32:107-108 (2002).

Li et al., "Folate-Mediated Targeting of Antisense Oligodeoxynucleotides to Ovarian Cancer Cells" *Pharm. Res.* 15(10):1540-1545 (1998).

Lipardi et al., "RNAi as Random Degradative PCR: siRNA Primers Convert mRNA into dsRNAs that are Degraded to Generate New siRNAs" *Cell* 107:297-307 (2001).

Lowy et al., "Function and Regulation of RAS" *Annu. Rev. Biochem.* 62:851-891 (1993).

Manche et al., "Interactions between Double-Stranded RNA Regulators and the Protein Kinase DAI" *Mol. and Cell. Biol.* 12(11):5238-5248 (1992).

Manoharan, "Oligonucleotide Conjugates as Potential Antisense Drugs with Improved Uptake, Biodistribution, Targeted Delivery and Mechanism of Action" *Antisense and Nucleic Acid Drug Development* 12:103-128 (2002).

Manoharan et al., "Chemical Modifications to Improve Uptake and Bioavailability of Antisense Oligonucleotides" *Ann. NY Acad. Sci.* 660:306-309 (1992).

Manoharan et al., "Introduction of a Lipophilic Thioether Tether in the Minor Groove of Nucleic Acids for Antisense Applications" *Bioorg. Med. Chem. Lett.* 3(12):2765-2770 (1993).

Manoharan et al., "Cholic Acid-Oligonucleotide Conjugates for Antisense Applications" *Bioorg. Med. Chem. Lett.* 4(8):1053-1060 (1994).

Manoharan et al., "Oligonucleotide Conjugates Alteration of the Pharmacokinetic Properties of Antisense Agents" *Nucleosides & Nucleotides* 14:969-973 (1995).

Manoharan et al., "Lipidic Nucleic Acids" *Tetrahedron* 36:3651-3654 (1995).

Maru, "Molecular Biology of Chronic Myeloid Leukemia" *Int. J. Hematol.* 73:308-322 (2001).

Matrisian, "Cancer biology: Extracellular proteinases in malignancy" *Curr. Biol.* 9(20):R776-778 (1999).

McCaffrey et al., "RNA interference in adult mice" *Nature* 418:38-39 (2002).

Mendelsohn et al., "The EGF receptor family as target for cancer therapy" *Oncogene* 19(56):6550-6565 (2000).

Mignatti et al., "Biology and Biochemistry of proteinases in Tumor Invasion" *Physiol. Rev.* 73:161-195 (1993).

Mishra et al., "Improved leishmanicidal effect of phosphorotioate antisense oligonucleotides by LDL-mediated delivery" *Biochim. Biophys. Acta.* 1264:229-237 (1995).

Montgomery et al., "Double-stranded RNA as a mediator in sequence-specific gentic silencing and co-suppression" *TIG* 14(7):255-258 (1998).

Muellauer et al., "Mutations in apoptosis genes: a pathogenetic factor for human disease" *Mutat. Res.* 488(3):211-231 (2001).

Muzyczaka, "Use of Adeno-Associated Virus as a General Transduction Vector for Mammalian Cells" *Curr. Topics Micro. Immunol.* 158:97-129 (1992).

Ngô et al., "Double-stranded RNA induces mRNA degradation in *Trypanosoma brucei*" *PNAS USA* 95:14687-14692 (1998).

Normanno et al., "The role of EGF-Related Peptides in Tumor Growth" *Front. Biosci.* 6:D685-707 (2001).

Oberhauser et al., "Effective incorporation of 2'-O-methyl-oligoribonucleotides into liposomes and enhanced cell association through modification with thiocholesterol" *Nucl. Acids Res.* 20:533-538 (1992).

Obika et al., "Stability and structural features of the duplexes containing nucleoside analogues with a fixed N-type conformation, 2'-*O*,4'-*C*-methyleneribonucleosides" *Tetrahedron* 39:5401-5404 (1998).

Ouchi et al., "Synthesis and Antitumor Activity of Poly(Ethylene Glycol)s Linked to 5-Fluorouracil via a Urethane or Urea Bond" *Drug Design and Discovery* 9:93-105 (1992).

Paddison et al., "Short hairpin RNAs (siRNAs) induce sequence-specific silencing in mammalian cells" *Genes & Development* 16:948-958 (2002).

Pandolfi, "In vivo analysis of the molecular genetics of acute promyelocytic leukemia" *Oncogene* 20:5726-5735 (2001).

Phillips et al., "The NZB Mouse as Model for Chronic Lymphocytic Leukemia" *Cancer Res.* 52(2):437-443 (2000).

Pollock et al., "Mouse models of acute promyelocytic leukemia" *Curr. Opin. Hematol.* 8:206-211 (2001).

Polushin et al., "Synthesis of Oligonucleotides Containing 2'-Azido- and 2'-Amino-2'-deoxyuridine Using Phosphotriester Chemistry" *Tetrahedron* 37:3227-3230 (1996).

Randall et al., "Clearance of replicating hepatitis C virus replicon RNAs in cell culture by small interfering RNAs" *PNAS USA* 100(1):235-240 (2003).

Ravasio, "Selective Hydrogenations Promoted by Copper Catalysts. 1. Chemoselectivity, Regioselectivity, and Stereoselectivity in the Hydrogenation of 3-Substituted Steroids" *J. Org. Chem.* 56:4329-4333 (1991).

Reed, "Mechanisms of Apoptosis" *Am. J. Pathol.* 157(5):1415-1430 (2000).

Rego et al., "Analysis of the Molecular Genetics of Acute Promyelocytic Leukemia in Mouse Models" *Semin. in Hemat.* 38:54-70 (2001).

Rosenfeld et al., "Adenovirus-Mediated Transfer of a Recombinant a!-Antitrypsin Gene to the Lung Epithelium in Vivo" *Science* 252:431-434 (1991).

Rosenfeld et al., "In Vivo Transfer to the Human Cystic Fibrosis Transmembrane Conductance Regulator Gene to the Airway Epithelium" *Cell* 68:143-155 (1992).

Saison-Behmoaras et al., "Short modified antisense oligonucleotides directed against Ha-*ras* point mutation induce selective cleavage of the mRNA and inhibit T24 cells proliferation" *EMBO J.* 10:111-118 (1991).

Scheffer et al., "The drug resistance-related protein LRP is the human major vault protein" *Nat. Med.* 1(6):578-582 (1995).

Scherr et al., "Quantitative Determination of Lentiviral Vector Particle Numbers by Real-Time PCR" *BioTechniques* 31:520-526 (2001).

Secrist et al., Abstract 21, *Program & Abstracts, Tenth International Roundtable, Nucleosides, Nucleotides and their Biological Applications*, Park City, Utah, Sep. 16-20 (1992).

Shannon et al., "Modeling myeloid leukemia tumors suppressor gene inactivation in the mouse" *Semin. Cancer Biol.* 11:191-200 (2001).

Sharp, "RNA interference—2001" *Genes & Development* 15:485-490 (2001).

Shea et al., "Synthesis, hybridization properties and antiviral activity of lipid-oligodeoxynucleotide conjugates" *Nucl. Acids Res.* 18:3777-3783 (1990).

Sijen et al., "On the Role of RNA Amplification in dsRNA-Triggered Gene Silencing" *Cell* 107:465-476 (2001).

Skorski et al., "Suppression of Philadelphia[1] leukemia cell growth in mice by BCR-ABL antisense oligodeoxynucleotide" *Proc. Natl. Acad. Sci. USA* 91:4504-4508 (1994).

Stetler-Stevenson et al., "Tumor Cell Interactions with the Extracellular Matrix During Invasion and Metastasis" *Annu. Rev. Cell Biol.* 9:541-573 (1993).

Strasser et al, "Apoptosis Signaling" *Annu. Rev. Biochem.* 69:217-245 (2000).

Svinarchuk et al., "Inhibition of HIV proliferation in MT-4 cells by antisense oligonucleotide conjugated to lipophilic groups" *Biochimie* 75:49-54 (1993).

Thomson et al., "Synthesis and Properties of Diuridine Phosphate Analogues Containign Thio and Amino Modifications" *J. Org. Chem.* 61:6273-6281 (1996).

Tijsterman et al., "The Genetics of RNA Silencing" *Annu. Rev. Genet.* 36:489-519 (2002).

Tuschl et al., "Targeted mRNA degradation by double-stranded RNA in vitro" *Genes & Development* 13:3191-3197 (1999).

Van Beusechem et al., "Long-term expression of human adenosine deaminase in rhesus monkeys transplanted with retrovirus-infected bone-marrow cells" *Proc. Natl. Acad. Sci. USA* 89:7640-7649 (1992).

Van Etten, "Pathogenesis and treatment of Ph[+] leukemia: recent insights from mouse models" *Curr. Opin. Hematol.* 8:224-230 (2001).

Wagner, "The state of the art in antisense research" *Nat. Med.* 1:1116-1118 (1995).

Wianny et al., "Specific interference with gene function by double-stranded RNA in early mouse development" *Nature Cell Biology* 2:70-75 (2000).

Wild et al., "The 2 Å structure of helix 6 of the human signal recognition particle RNA" *Structure* 7(11):1345-1352 (1999).

Williams et al., Thermodynamic Comparison of the Salt Dependence of Natural RNA Hairpins and RNA Hairpins with Non-Nucleotide Spacers *Biochemistry* 35:14665-14670 (1996).

Wilson et al., "Retrovirus-mediated transduction of adult hepatocytes" *Proc. Natl. Acad. Sci. USA* 85:3014-3018 (1988).

Wong et al., "Modeling Philadelphia chromosome positive leukemias" *Oncogene* 20:5644-5659 (2001).

Yang et al., "Evidence that processed small dsRNAs may mediate sequence-specific mRNA degradation during RNAi in *Drosophila* embryos" *Current Biology* 10:1191-1200 (2000).

Yokota, "Tumor progression and metastasis" *Carcinogenesis* 21:497-503 (2000).

Yu et al., "RNA interference by expression of short-interfering RNAs and hairpin RNAs in mammalian cells" *PNAS USA* 99(9):6047-6052 (2002).

Zamore et al., "RNAi: Double-Stranded RNA Directs the ATP-Dependent Cleavage of mRNA at 21 to 23 Nucleotide Intervals" *Cell* 101:25-33 (2000).

Zeng et al., "The Fetal Origin of B-Precursor Leukemia in the Eμ-ret Mouse" *Blood* 92(10):3529-3536 (1988).

U.S. Appl. No. 60/117,635, Li et al. (filed Jan. 28, 1999).

U.S. Appl. No. 60/130,377, Pachuk et al. (filed Apr. 21, 1999).

Agrawal et al., "Self-Stabilized Oligonucleotides as Novel Antisense Agents" *Delivery Strategies for Antisense Oligonucleotide Therapeutics*, Edited by Saghir Akhtar, CRC Press, pp. 105-121 (1995).

Bahramian et al., "Transcriptional and Posttranscriptional Silencing of Rodent α1 (I) Collagen by a Homologous Transcriptionally Self-Silenced Transgene" *Mol. Cell. Biol.* 19:274-283 (1999).

Barawkar et al., "Synthesis, biophysical properties, and nuclease resistance properties of mixed backbone oligodeoxynucleotides containing cationic internucleoside guanidinium linkages: Deoxynucleic guanidine/DNA chimeras" *Proc. Natl. Acad. Sci. USA* 95:11047-11052 (1998).

Barber et al., "Mutants of the RNA-Dependent Protein Kinase (PKR) Lacking Double-Stranded RNA Binding Domain I Can Act as Transdominant Inhibitors and Induce Malignant Transformation" *Mol. Cell. Biol.* 15:3138-3146 (1995).

Bhan et al., "2',5'-Linked oligo-3'-deoxyribonucleoside phosphorothioate chimeras: thermal stability and antisense inhibition of gene expression" *Nucleic Acids Res.* 25:3310-3317 (1997).

Billy et al., "Specific interference with gene expression induced by long, double-stranded RNA in mouse embryonal teratocarcinoma cell lines" *Proc. Natl. Acad. Sci. USA* 98:14428-14433 (2001).

Borecky et al., "Therapeutic use of double-stranded RNAs in man" *Tex. Rep. Biol. Med.* 41:575-581 (1981-1982) (Abstract only).

Braich et al., "Regiospecific Solid-Phase Synthesis of Branched Oligonucleotides. Effect of Vicinal 2',5'-(or 2'.3'-) and 3',5'-Phosphodiester Linkages on the Formation of Hairpin DNA" *Bioconjug. Chem.* 8:370-377 (1997).

Brennicke et al., "RNA editing" *FEMS Microbiology Reviews* 23:297-316 (1999).

Byrom et al., "Inducing RNAi with siRNA Cocktails Generated by RNase III" *TechNotes* 10(1), Ambion website (2004).

Chien et al., "Novel cationic cardiolipin analogur-based liposome for efficient DNA and small interfering RNA delivery in vitro and in vivo" *Cancer Gene Therapy* pp. 1-8 (2004).

Couzin, "Small RNAs Make Big Splash" *Science* 298:2296-2297 (2002).

Czauderna et al., "Structural variations and stabilizing modifications of synthetic siRNAs in mammalian cells" *Nucleic Acids Res.* 31:1-12 (2003).

Dellweg et al., ed., *Römpp Lexikon Biotechnologie*, p. 354 and p. 673 (1992) (in German).

Elbashir et al., "Analysis of gene function in somatic mammalian cells using small interfering RNAs" *Methods* 26:199-213 (2002).

Fallert-Müller, ed., *Encyclopedia of Biochemistry*, vol. J-Z, pp. 448-449 (2000) (in German).

Grasby et al., "Purine Functional Groups in Essential Residues of the Hairpin Ribozyme Required for Catalytic Cleavage of RNA" *Biochemistry* 34:4068-4076 (1995).

Griffey et al., "2'-O-Aminopropyl Ribonucleotides: A Zwitterionic Modification That Enhances the Exonuclease Resistance and Biological Activity of Antisense Oligonucleotides" *J. Med. Chem.* 39:5100-5109 (1996).

Gryaznov et al., "Template controlled coupling and recombination of oligonucleotide blocks containing thiophosphoryl groups" *Nucleic Acids Res.* 21:1403-1408 (1993).

Ha et al., "a bulged *lin-4lin114* RNA duplex is sufficient for *Caenorhabditis elegans lin-14* temporal gradient formation" *Genes & Development* 10:3041-3050 (1996).

Hamilton et al., "A Species of Small Antisense RNA in Post-transcriptional Gene Silencing in Plants" *Science* 286:950-952 (1999).

Hedges, "The Orgin and Evolution of Model Organisms" *Nature Reviews* 3:838-849 (2002).

Hoke et al., "Effects of phosphorothioate capping on antisense oligonucleotide stability, hybridization and antivivral efficacy versus herpes simplex virus infection" *Nucleic Acids Res.* 19:5743-5748 (1991).

Horn et al., "Chemical synthesis and characterization of branched oligodeoxyribonucleotides (bDNA) for use as signal amplifiers in nucleic acid quantification assays" *Nucleic Acids Res.* 25:4842-4849 (1997).

Hornung et al., "Sequence-specific potent induction of IFN-α by short interfering RNA in plasmacytoid dendritic cells through TLR7" *Nature Medicine* 11:263-270 (2005).

Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma" *Cancer Res.* 65:8984-8992 (2005).

Hunter et al., "The characteristics of inhibition of protein synthesis by double stranded ribonucleic acid in reticulocyte lysates" *J. Biol. Chem.* 250:409-417 (1975).

"InBase, The Intein Database: The Intein Registry—Inteins Sorted by Species" http://tools.neb.com/inbase/list.php (database updated on May 22, 2006).

International Preliminary Examination Report from PCT/DE00/00244.

"Introduction of DNA into Mammalian Cells" *Current Protocols in Molecular Biology*, Supplement 48, Edited by Frederick M. Ausubel et al., John Wiley & Sons, Inc., pp. 9.4.7-9.4.8 (1999).

Iwase et al., "Gene regulation by decoy approach (I): synthesis and properties of photo-crosslinked oligonucleotides" *Nucleic Acids Symp. Ser.* 37:203-204 (1997).

Judge et al., "Sequence-dependent stimulation of the mammalian innate immune response by synthetic siRNA" *Nat. Biotechnol.* pp. 1-6 (2005) (8 pages of supplementary content included).

Kennerdell et al., "Use of dsRNA-Mediated Genetic Interference to Demonstrate that *frizzled* and *frizzled 2* Act in the Wingless Pathway" *Cell* 95:1017-1026 (1998).

Kitabwalla et al., "RNA-Interference—A New Weapon Against HIV and Beyond" *N. Engl. J. Med.* 347:1364-1367 (2002).

Kreutzer et al., "Specific inhibition of viral gene expression by double-stranded RNA in vitro" *Annual Fall Meeting of the GBH*, Abstract for Poster Paper No. 328, p. S169 (1999).

Kumar et al., "Antisense RNA: function and fate of duplex RNA in cells of higher eukaryotes" *Microbiol. Mol. Biol. Rev.* 62:1415-1434 (1998).

Lee et al., "The *C. elegans* Heterochronic Gene *lin-4* Encodes Small RNAs with Antisense Complementarity to *lin-1*" *Cell* 75:843-854 (1993).

Letter to the International Examining Authority from Gassner & Partner in the prosecution of PCT/DE00/00244 (WO 00/44895), 5 pages (Mar. 28, 2001) (in German).

Li et al., "Double-stranded RNA injection produces null phenotypes in zebrafish" *Dev. Biol.* 210:238, Abstract No. 346 (1999).

Lin et al., "Policing rogue genes" *Nature* 402:128-129 (1999).

Lipinski et al., "Experimental and computational approaches to estimate solubility and permeability in drug discovery and development settings" *Adv. Drug Deliv. Rev.* 23:3-25 (1997).

Ma et al., "Design and Synthesis of RNA Miniduplexes via a Synthetic Linker Approach" *Biochemistry* 32:1751-1758 (1993).

Majumdar et al., "Targeted gene knockout mediated by triple helix forming oligonucleotides" *Nat. Genet.* 20:212-214 (1998).

Marques et al., "Activation of the mammalian immune system by siRNAs" *Nat. Biotechnol.*, 23(11):1399-1405 (2005).

Martinez et al., "Single-Stranded Antisense siRNAs Guide Target RNA Cleavage in RNAi" *Cell*, 110:563-574 (2002).

McManus et al., "Gene Silencing in Mammals by Small Interfering RNAs" *Nat. Rev. Genet.*, 3:737-747 (2002).

Milhaud et al., "Free and Liposome-Encapsulated Double-Stranded RNAs as Inducers of Interferon, Interleukin-6, and Cellular Toxicity" *J. Interferon Res.*, 11:261-265 (1991).

Minks et al., "Structural Requirements of Double-stranded RNA for the Activation of 2',5'-Oligo(A) Polymerase and Protein Kinase of Interferon-treated HeLa Cells" *J. Biol. Chem.* 254(20):10180-10183 (1979).

Montgomery et al., "RNA as a target of double-stranded RNA-mediated genetic interference in *Caenorhabditis elegans*" *Proc. Natl. Acad. Sci. USA* 95:15502-15507 (1998).

Moss et al., "The Cold Shock Domain Protein LIN-28 Controls Developmental Timing in *C. elegans* and Is Regulated by the *lin-4* RNA" *Cell* 88:637-646 (1997).

Nielsen et al., "A novel class of conformationally restricted oligonucleotide analogues: synthesis of 2',3'-bridged monomers and RNA-selective hybridization" *Chem. Commun.* pp. 825-826 (1997).

Nikiforov et al., "Oligodeoxynucleotides containing 4-thiothymidine and 6-thiodeoxyguanosine as affinity labels for the Eco RV restriction endonuclease and modification methylase" *Nucleic Acids Res.* 20:1209-1214 (1992).

PCT/GB00/04404 as filed (Nov. 19, 1999).

Pegram et al., "Phase II Study of Receptor-Enhanced Chemosensitivity Using Recombinant Humanized Anti-p185[HER2]/*neu* Monoclonal Antibody Plus Cisplatin in Patients With HER2/*neu*-Overexpressing Metastic Breast Cancer Refractory to Chemotherapy Treatment" *J. Clin. Oncol.* 16:2659-2671 (1998).

Perler, "InBase: the Intein Database" *Nucleic Acids Res.* 30:383-384 (2002).

Regalado, "Turning Off Genes Sheds New Light On How They Work" *The Wall Street Journal*, 4 pages (Aug. 6, 2002).

Robbins et al., "Sensing the danger in RNA" *Nat. Med.* 11(3):250-251 (2005).

Schwarz et al., "Evidence that siRNAs Function as Guides, Not Primers, in the *Drosophila* and Human RNAi Pathways" *Mol. Cell* 10:537-548 (2002).

Sharp et al., "RNAi and double-strand RNA" *Genes Dev.* 13:139-141 (1999).

Shi et al., "A CBP/p300 homolog specifies multiple differentiation pathways in *Caenorhabditis elegans*" *Genes Dev.* 12:943-955 (1998).

Sinha, "Large-scale Synthesis. Approaches to Large-scale Synthesis of Oligodeoxynucleotides and their Analogs" *Antisense—From Technology to Therapy*, vol. 6, Edited by Reimar Schlingensiepen et al., pp. 29-58 (1997).

Skripkin et al., "Psoralen crosslinking between human immunodeficiency virus type 1 RNA and primer tRNA$_3^{Lys}$" *Nucleic Acids Res.* 24:509-514 (1996).

Sledz et al., "Activation of the interferon system by short-interfering RNAs" *Nat. Cell Biol.* 5(9):834-839 (2003).

Soutschek et al., "Therapeutic silencing of an endogenous gene by systemic administration of modified siRNAs" *Nature* 432:173-178 (2004).

Strauss, "Candidate 'Gene Silencers' Found" *Science* 286:886 (1999).

Timmons et al., "Specific interference by ingested dsRNA" *Nature* 395:854 (1998).

Uhlmann et al., "Antisense Oligonucleotides: A New Therapeutic Principle" *Chemical Reviews* 90:543-584 (1990).

Voinnet et al., "Systemic signalling in gene silencing" *Nature* 389:553 (1997).

Wargelius et al., "Double-Stranded RNA Induces Specific Developmental Defects in Zebrafish Embryos" *Biochem. Biophys. Res. Commun.* 263:156-161 (1999).

Waterhouse et al., "Virus resistance and gene silencing in plants can be induced by simultaneous expression of sense and antisense RNA" *Proc. Natl. Acad. Sci. USA* 95:13959-13964 (1998).

Wess et al., "Early days for RNAi" *BioCentury* 11:A1-A8 (2003).

Zeng et al., "RNA interference in human cells is restricted to the cytoplasm" *RNA* 8:855-860 (2002).

Zhao et al., "Double-Stranded RNA Injection Produces Nonspecific Defects in Zebrafish" *Dev. Biol.* 229:215-223 (2001).

Zheng et al., "Activation of the protein kinase PKR by short double-stranded RNAs with single-stranded tails" *RNA* 10:1934-1945 (2004).

Vickers, T. et al., "Efficient Reduction of Target RNAs by Small Interfering RNA and RNase H-Dependent Antisense Agents," The J. of Biological Chem., 278(9), 7108-7118, Feb. 28, 2003.

Luo et al., "The Gene-Silencing Effciency of siRNA is Strongly Dependant on the Local Structure of mRNA at the Targeted Region," Biochemical and Biophysical Research Communications, vol. 318(1):303-10 (2004).

Wacheck, et al., "Small Interfering RNA Targeting Bcl-2 Sensitizes Malignant Melanoma," Oligonucleotides, vol. 13 (5):393-400 (2003).

* cited by examiner

SEQUENCE LISTING

<160> NUMBER OF SEQ ID NOS: 491

<210> SEQ ID NO 1
<211> LENGTH: 22
<212> TYPE: RNA
<213> ORGANISM: Artificial Sequence

```
<220> FEATURE:
<223> OTHER INFORMATION: Sense strand of dsRNA that is complementary to
      a Sequence of the human Bcl-2 gene

<400> SEQUENCE: 1
caggaccucg ccgcugcaga cc                                              22

<210> SEQ ID NO 2
<211> LENGTH: 24
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 2
ggucugcagc ggcgaggucc uggc                                            24

<210> SEQ ID NO 3
<211> LENGTH: 22
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 3
gccuuugugg aacuguacgg cc                                              22

<210> SEQ ID NO 4
<211> LENGTH: 24
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 4
ggccguacag uuccacaaag gcau                                            24

<210> SEQ ID NO 5
<211> LENGTH: 22
<212> TYPE: RNA
<213> ORGANISM: Artificial Sequence
<220> FEATURE:
<223> OTHER INFORMATION: Sense strand of dsRNA that is complementary to
      a Sequence of the neomycin resistance gene

<400> SEQUENCE: 5
caaggaugag gaucguuucg ca                                              22

<210> SEQ ID NO 6
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the neomycin resistance gene

<400> SEQUENCE: 6
gcgaaacgau ccucauccug ucu                                             23

<210> SEQ ID NO 7
<211> LENGTH: 21
<212> TYPE: RNA
<213> ORGANISM: Artificial Sequence
<220> FEATURE:
```

```
<223> OTHER INFORMATION: Sense strand of dsRNA that is complementary to
      a Sequence of the human Bcl-2 gene

<400> SEQUENCE: 7
ccgggagaua gugaugaagu a                                              21

<210> SEQ ID NO 8
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 8
uacuucauca cuaucuccg guu                                             23

<210> SEQ ID NO 9
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 9
gacugaguac cugaaccggc a                                              21

<210> SEQ ID NO 10
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 10
ugccgguuca gguacucagu cau                                            23

<210> SEQ ID NO 11
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 11
cgauaaccgg gagauaguga u                                              21

<210> SEQ ID NO 12
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 12
aucacuaucu cccgguuauc gua                                            23

<210> SEQ ID NO 13
<211> LENGTH: 21
<212> TYPE: RNA
<213> ORGANISM: Artificial Sequence
<220> FEATURE:
<223> OTHER INFORMATION: Sense strand of dsRNA that is complementary to
``` a Sequence of the human Bcl-2 gene

<400> SEQUENCE: 13
gguacgauaa ccgggagaua g                                              21

<210> SEQ ID NO 14
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 14
cuaucucccg guuaucguac ccc                                            23

<210> SEQ ID NO 15
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 15
guacgauaac cgggagauag u                                              21

<210> SEQ ID NO 16
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 16
acuaucuccc gguuaucgua ccc                                            23

<210> SEQ ID NO 17
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 17
uguggaugac ugaguaccug a                                              21

<210> SEQ ID NO 18
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 18
ucagguacuc agucauccac agg                                            23

<210> SEQ ID NO 19
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

```
<400> SEQUENCE: 19
ggucaugugu guggagagcg u                                              21

<210> SEQ ID NO 20
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 20
acgcucucca cacacaugac ccc                                            23

<210> SEQ ID NO 21
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 21
guggaugacu gaguaccuga a                                              21

<210> SEQ ID NO 22
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 22
uucagguacu cagucaucca cag                                            23

<210> SEQ ID NO 23
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 23
cccuguggau gacugaguac c                                              21

<210> SEQ ID NO 24
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 24
gguacucagu cauccacagg gcg                                            23

<210> SEQ ID NO 25
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene
```

```
<400> SEQUENCE: 25
uguggaugac ugaguaccug a                                              21

<210> SEQ ID NO 26
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 26
ucagguacuc agucauccac agg                                            23

<210> SEQ ID NO 27
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 27
accgggcauc uucuccuccc a                                              21

<210> SEQ ID NO 28
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 28
ugggaggaga agaugcccgg ugc                                            23

<210> SEQ ID NO 29
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 29
ggccuucuuu gaguucggug g                                              21

<210> SEQ ID NO 30
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 30
ccaccgaacu caaagaaggc cac                                            23

<210> SEQ ID NO 31
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 31
```
cugaguaccu gaaccggcac c                                              21

<210> SEQ ID NO 32
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 32
ggugccgguu cagguacuca guc                                            23

<210> SEQ ID NO 33
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 33
guggccuucu uugaguucgg u                                              21

<210> SEQ ID NO 34
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 34
accgaacuca aagaaggcca caa                                            23

<210> SEQ ID NO 35
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 35
uccauuauaa gcugucgcag a                                              21

<210> SEQ ID NO 36
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 36
ucugcgacag cuuauaaugg aug                                            23

<210> SEQ ID NO 37
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 37

```
ggggucaugu guguggagag c                                      21
```

<210> SEQ ID NO 38
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 38

```
gcucuccaca cacaugaccc cac                                    23
```

<210> SEQ ID NO 39
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 39

```
ggaugacuga guaccugaac c                                      21
```

<210> SEQ ID NO 40
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 40

```
gguucaggua cucagucauc cac                                    23
```

<210> SEQ ID NO 41
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 41

```
guaccugaac cggcaccugc a                                      21
```

<210> SEQ ID NO 42
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 42

```
ugcaggugcc gguucaggua cuc                                    23
```

<210> SEQ ID NO 43
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 43

```
ggacaacauc gcccugugga u                                      21
```

<210> SEQ ID NO 44
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 44
auccacaggg cgauguuguc cac                                             23

<210> SEQ ID NO 45
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 45
cauuauaagc ugucgcagag g                                               21

<210> SEQ ID NO 46
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 46
ccucugcgac agcuuauaau gga                                             23

<210> SEQ ID NO 47
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 47
gggucaugug uguggagagc g                                               21

<210> SEQ ID NO 48
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 48
cgcucuccac acacaugacc cca                                             23

<210> SEQ ID NO 49
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 49
gggagauagu gaugaaguac a                                               21

<210> SEQ ID NO 50
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 50
uguacuucau cacuaucucc cgg                                            23

<210> SEQ ID NO 51
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 51
caugugugug gagagcguca a                                              21

<210> SEQ ID NO 52
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 52
uugacgcucu ccacacacau gac                                            23

<210> SEQ ID NO 53
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 53 gugggguucau guguguggag a                                             21

<210> SEQ ID NO 54
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 54
ucuccacaca caugaccccca ccg                                           23

<210> SEQ ID NO 55
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 55
ugaaguacau ccauuauaag c                                              21

```
<210> SEQ ID NO 56
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 56
gcuuauaaug gauguacuuc auc                                                23

<210> SEQ ID NO 57
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 57
ccuguggaug acugaguacc u                                                  21

<210> SEQ ID NO 58
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 58
agguacucag ucauccacag ggc                                                23

<210> SEQ ID NO 59
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 59
ucaugugugu ggagagcguc a                                                  21

<210> SEQ ID NO 60
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 60
ugaggcucuc cacacacaug acc                                                23

<210> SEQ ID NO 61
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 61
cgcccugugg augacugagu a                                                  21

<210> SEQ ID NO 62
```

```
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 62
uacucaguca uccacagggc gau                                              23

<210> SEQ ID NO 63
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 63
uggaugacug aguaccugaa c                                                21

<210> SEQ ID NO 64
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 64
guucagguac ucagucaucc aca                                              23

<210> SEQ ID NO 65
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 65
acaccuggau ccaggauaac g                                                21

<210> SEQ ID NO 66
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 66
cguuauccug gauccaggug ugc                                              23

<210> SEQ ID NO 67
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 67
ggaugccuuu guggaacugu a                                                21

<210> SEQ ID NO 68
<211> LENGTH: 23
```

```
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 68
uacaguucca caaaggcauc cca                                               23

<210> SEQ ID NO 69
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 69
gucaugugug uggagagcgu c                                                 21

<210> SEQ ID NO 70
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 70
gacgcucucc acacacauga ccc                                               23

<210> SEQ ID NO 71
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 71
gccucuguuu gauuucuccu g                                                 21

<210> SEQ ID NO 72
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 72
caggagaaau caaacagagg ccg                                               23

<210> SEQ ID NO 73
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 73
cggccucugu uugauuucuc c                                                 21

<210> SEQ ID NO 74
<211> LENGTH: 23
<212> TYPE: RNA
```

```
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 74
ggagaaauca aacagaggcc gca                                          23

<210> SEQ ID NO 75
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 75
ggcuacgagu gggaugcggg a                                            21

<210> SEQ ID NO 76
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 76
ucccgcaucc cacucguagc ccc                                          23

<210> SEQ ID NO 77
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 77
aggguacgau aaccgggaga u                                            21

<210> SEQ ID NO 78
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 78
aucucccggu uaucguaccc ugu                                          23

<210> SEQ ID NO 79
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 79
caggguacga uaaccgggag a                                            21

<210> SEQ ID NO 80
<211> LENGTH: 23
<212> TYPE: RNA
<213> ORGANISM: Artificial Sequence
```

```
<220> FEATURE:
<223> OTHER INFORMATION: Antisense strand of dsRNA that is complementary
      to a Sequence of the human Bcl-2 gene

<400> SEQUENCE: 80
ucucccgguu aucguacccu guu                                              23

<210> SEQ ID NO 81
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 81
cgguggdguc augugugugg a                                                21

<210> SEQ ID NO 82
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 82
uccacacaca ugaccccacc gaa                                              23

<210> SEQ ID NO 83
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 83
acgauaaccg ggagauagug a                                                21

<210> SEQ ID NO 84
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 84
ucacuaucuc ccgguuaucg uac                                              23

<210> SEQ ID NO 85
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 85
uggccuucuu ugaguucggu g                                                21

<210> SEQ ID NO 86
<211> LENGTH: 23
<212> TYPE: RNA
<213> ORGANISM: Artificial Sequence
<220> FEATURE:
```

<223> OTHER INFORMATION: Antisense strand of dsRNA that is complementary
     to a Sequence of the human Bcl-2 gene

<400> SEQUENCE: 86
caccgaacuc aaagaaggcc aca                                             23

<210> SEQ ID NO 87
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 87
cgggagauag ugaugaagua c                                               21

<210> SEQ ID NO 88
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 88
guacuucauc acuaucuccc ggu                                             23

<210> SEQ ID NO 89
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 89
aaguacaucc auuauaagcu g                                               21

<210> SEQ ID NO 90
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 90
cagcuuauaa uggauguacu uca                                             23

<210> SEQ ID NO 91
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 91
cauccauuau aagcugucgc a                                               21

<210> SEQ ID NO 92
<211> LENGTH: 23
<212> TYPE: RNA
<213> ORGANISM: Artificial Sequence
<220> FEATURE:
<223> OTHER INFORMATION: Antisense strand of dsRNA that is complementary to a Sequence of the human Bcl-2 gene

<400> SEQUENCE: 92
ugcgacagcu uauaauggau gua                                                    23

<210> SEQ ID NO 93
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 93
uguggccuuc uuugaguucg g                                                      21

<210> SEQ ID NO 94
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 94
ccgaacucaa agaaggccac aau                                                    23

<210> SEQ ID NO 95
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 95
cuacgagugg gaugcgggag a                                                      21

<210> SEQ ID NO 96
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 96
ucucccgcau cccacucgua gcc                                                    23

<210> SEQ ID NO 97
<211> LENGTH: 21
<212> TYPE: RNA
<213> ORGANISM: Artificial Sequence
<220> FEATURE:
<223> OTHER INFORMATION: Sense strand of dsRNA that is complementary
      to a Sequence of the human Bcl-2 gene

<400> SEQUENCE: 97
augaaguaca uccauuauaa g                                                      21

<210> SEQ ID NO 98
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

```
<400> SEQUENCE: 98
cuuauaaugg auguacuuca uca                                              23

<210> SEQ ID NO 99
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 99
gccuucuuug aguucggugg g                                                21

<210> SEQ ID NO 100
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 100
cccaccgaac ucaaagaagg cca                                              23

<210> SEQ ID NO 101
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 101
augugugugg agagcgucaa c                                                21

<210> SEQ ID NO 102
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 102
guugacgcuc uccacacaca uga                                              23

<210> SEQ ID NO 103
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 103
uaaccgggag auagugauga a                                                21

<210> SEQ ID NO 104
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene
```

```
<400> SEQUENCE: 104
uucaucacua ucucccgguu auc                                            23

<210> SEQ ID NO 105
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 105
cuguggauga cugaguaccu g                                              21

<210> SEQ ID NO 106
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 106
cagguacuca gucauccaca ggg                                            23

<210> SEQ ID NO 107
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 107
gacgacuucu cccgccgcua c                                              21

<210> SEQ ID NO 108
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 108
guagcggcgg gagaagucgu cgc                                            23

<210> SEQ ID NO 109
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 109
ccuucuuuga guucgguggg g                                              21

<210> SEQ ID NO 110
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 110
```
ccccaccgaa cucaaagaag gcc                                              23

<210> SEQ ID NO 111
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 111
gacaacaucg cccuguggau g                                                21

<210> SEQ ID NO 112
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 112
cauccacagg gcgauguugu cca                                              23

<210> SEQ ID NO 113
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 113 uguguguqga gagcgucaac c                                                21

<210> SEQ ID NO 114
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 114
gguugacgcu cuccacacac aug                                              23

<210> SEQ ID NO 115
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 115
gcccugugga ugacugagua c                                                21

<210> SEQ ID NO 116
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 116
guacucaguc auccacaggg cga                                              23

<210> SEQ ID NO 117
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 117
ccauuauaag cugucgcaga g                                                21

<210> SEQ ID NO 118
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 118
cucugcgaca gcuuauaaug gau                                              23

<210> SEQ ID NO 119
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 119
ugccuuugug gaacuguacg g                                                21

<210> SEQ ID NO 120
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 120
ccguacaguu ccacaaaggc auc                                              23

<210> SEQ ID NO 121
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 121
cuucuuugag uucggugggg u                                                21

<210> SEQ ID NO 122
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 122
accccaccga acucaaagaa ggc                                              23

```
<210> SEQ ID NO 123
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 123
gaugacugag uaccugaacc g                                              21

<210> SEQ ID NO 124
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 124
cgguucaggu acucagucau cca                                            23

<210> SEQ ID NO 125
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 125
cgacuucgcc gagaugucca g                                              21

<210> SEQ ID NO 126
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 126
cuggacaucu cggcgaaguc gcc                                            23

<210> SEQ ID NO 127
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 127
gcgacuucgc cgagaugucc a                                              21

<210> SEQ ID NO 128
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 128
uggacaucuc ggcgaagucg cgg                                            23
```

<210> SEQ ID NO 129
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 129
uggggucaug uguguggaga g                                                 21

<210> SEQ ID NO 130
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 130
cucuccacac acaugacccc acc                                               23

<210> SEQ ID NO 131
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 131
gacgacuucu cccgccgcua c                                                 21

<210> SEQ ID NO 132
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 132
guagcggcgg gagaagucgu cgc                                               23

<210> SEQ ID NO 133
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 133
accgggagau agugaugaag u                                                 21

<210> SEQ ID NO 134
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 134
acuucaucac uaucucccgg uua                                               23

```
<210> SEQ ID NO 135
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 135
accgggagau agugaugaag u                                                 21

<210> SEQ ID NO 136
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 136
acuucaucac uaucucccgg uua                                               23

<210> SEQ ID NO 137
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 137
cacgcuggga gaacggggua c                                                 21

<210> SEQ ID NO 138
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 138
guaccccguu cucccagcgu gcg                                               23

<210> SEQ ID NO 139
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 139
gggcuacgag ugggaugcgg g                                                 21

<210> SEQ ID NO 140
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 140
cccgcauccc acucguagcc ccu                                               23

<210> SEQ ID NO 141
```

```
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 141
caucgcccug uggaugacug a                                              21

<210> SEQ ID NO 142
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 142
ucagucaucc acagggcgau guu                                            23

<210> SEQ ID NO 143
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 143
acaacaucgc ccuguggaug a                                              21

<210> SEQ ID NO 144
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 144
ucauccacag ggcgauguug ucc                                            23

<210> SEQ ID NO 145
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 145
cgacgacuuc ucccgccgcu a                                              21

<210> SEQ ID NO 146
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 146
uagcggcggg agaagucguc gcc                                            23

<210> SEQ ID NO 147
<211> LENGTH: 21
```

```
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 147
gggagaacgg gguacgacaa c                                               21

<210> SEQ ID NO 148
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 148
guugucguac cccguucucc cag                                             23

<210> SEQ ID NO 149
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 149
uguggagagc gucaaccggg a                                               21

<210> SEQ ID NO 150
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 150
ucccgguuga cgcucuccac aca                                             23

<210> SEQ ID NO 151
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 151
ggagagcguc aaccgggaga u                                               21

<210> SEQ ID NO 152
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 152
aucucccggu ugacgcucuc cac                                             23

<210> SEQ ID NO 153
<211> LENGTH: 21
<212> TYPE: RNA
```

```
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 153
guguguggag agcgucaacc g                                                   21

<210> SEQ ID NO 154
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 154
cgguugacgc ucuccacaca cau                                                 23

<210> SEQ ID NO 155
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 155
cgggcaucuu cuccucccag c                                                   21

<210> SEQ ID NO 156
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 156
gcugggagga gaagaugccc ggu                                                 23

<210> SEQ ID NO 157
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 157
cuggauccag gauaacggag g                                                   21

<210> SEQ ID NO 158
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 158
ccuccguuau ccuggaucca ggu                                                 23

<210> SEQ ID NO 159
<211> LENGTH: 21
<212> TYPE: RNA
<213> ORGANISM: Artificial Sequence
```

```
<220> FEATURE:
<223> OTHER INFORMATION: Sense strand of dsRNA that is complementary to
      a Sequence of the human Bcl-2 gene

<400> SEQUENCE: 159
gaaguacauc cauuauaagc u                                              21

<210> SEQ ID NO 160
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 160
agcuuauaau ggauguacuu cau                                            23

<210> SEQ ID NO 161
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 161
gcggccucug uuugauuucu c                                              21

<210> SEQ ID NO 162
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 162
gagaaaucaa acagaggccg cau                                            23

<210> SEQ ID NO 163
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 163
uucgccgaga uguccagcca g                                              21

<210> SEQ ID NO 164
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 164
cuggcuggac aucucggcga agu                                            23

<210> SEQ ID NO 165
<211> LENGTH: 21
<212> TYPE: RNA
<213> ORGANISM: Artificial Sequence
<220> FEATURE:
```

<223> OTHER INFORMATION: Sense strand of dsRNA that is complementary to
     a Sequence of the human Bcl-2 gene

<400> SEQUENCE: 165
auccauuaua agcugucgca g                                        21

<210> SEQ ID NO 166
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 166
cugcgacagc uuauaaugga ugu                                      23

<210> SEQ ID NO 167
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 167
uggagagcgu caaccgggag a                                        21

<210> SEQ ID NO 168
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 168
ucucccgguu gacgcucucc aca                                      23

<210> SEQ ID NO 169
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 169
ggagagcguc aaccgggaga u                                        21

<210> SEQ ID NO 170
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 170
aucucccggu ugacgcucuc cac                                      23

<210> SEQ ID NO 171
<211> LENGTH: 21
<212> TYPE: RNA
<213> ORGANISM: Artificial Sequence
<220> FEATURE:
<223> OTHER INFORMATION: Sense strand of dsRNA that is complementary to a Sequence of the human Bcl-2 gene

<400> SEQUENCE: 171
uguguggaga gcgucaaccg g                                              21

<210> SEQ ID NO 172
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 172
ccgguugacg cucuccacac aca                                            23

<210> SEQ ID NO 173
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 173
acuucgccga gauguccagc c                                              21

<210> SEQ ID NO 174
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 174
ggcuggacau cucggcgaag ucg                                            23

<210> SEQ ID NO 175
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 175
aaccgggaga uagugaugaa g                                              21

<210> SEQ ID NO 176
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 176
cuucaucacu aucucccggu uau                                            23

<210> SEQ ID NO 177
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene -continued

<400> SEQUENCE: 177
gcccuggugg gagcuugcau c					21

<210> SEQ ID NO 178
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 178
gaugcaagcu cccaccaggg cca					23

<210> SEQ ID NO 179
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 179
gcccuggugg gagcuugcau c					21

<210> SEQ ID NO 180
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 180
gaugcaagcu cccaccaggg cca					23

<210> SEQ ID NO 181
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 181
uggacaacau cgcccugugg a					21

<210> SEQ ID NO 182
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 182
uccacagggc gauguugucc acc					23

<210> SEQ ID NO 183
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

```
<400> SEQUENCE: 183
caacaucgcc cuguggauga c                                              21

<210> SEQ ID NO 184
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 184
gucauccaca gggcgauguu guc                                            23

<210> SEQ ID NO 185
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 185
cgcugggaga acgggguacg a                                              21

<210> SEQ ID NO 186
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 186
ucguaccccg uucucccagc gug                                            23

<210> SEQ ID NO 187
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 187
caccuggauc caggauaacg g                                              21

<210> SEQ ID NO 188
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 188
ccguuauccu ggauccaggu gug                                            23

<210> SEQ ID NO 189
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 189
```
ucgcccugug gaugacugag u                                                    21

<210> SEQ ID NO 190
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 190
acucagucau ccacagggcg aug                                                  23

<210> SEQ ID NO 191
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 191
accuggaucc aggauaacgg a                                                    21

<210> SEQ ID NO 192
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 192
uccguuaucc uggauccagg ugu                                                  23

<210> SEQ ID NO 193
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 193
accgccgcga cuucgccgag a                                                    21

<210> SEQ ID NO 194
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 194
ucucggcgaa gucgcggcgg uag                                                  23

<210> SEQ ID NO 195
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 195
ucuuugaguu cgguggggguc a          21

<210> SEQ ID NO 196
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 196
ugaccccacc gaacucaaag aag          23

<210> SEQ ID NO 197
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 197
aucgcccugu ggaugacuga g          21

<210> SEQ ID NO 198
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 198
cucagucauc cacagggcga ugu          23

<210> SEQ ID NO 199
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 199
ccuggaucca ggauaacgga g          21

<210> SEQ ID NO 200
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 200
cuccguuauc cuggauccag gug          23

<210> SEQ ID NO 201
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 201
uucuuugagu ucgguggggu c          21

```
<210> SEQ ID NO 202
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 202
gaccccaccg aacucaaaga agg                                           23

<210> SEQ ID NO 203
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 203
augacugagu accugaaccg g                                             21

<210> SEQ ID NO 204
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 204
ccgguucagg uacucaguca ucc                                           23

<210> SEQ ID NO 205
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 205
gacgcuuugc cacgguggug g                                             21

<210> SEQ ID NO 206
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 206
ccaccaccgu ggcaaagcgu ccc                                           23

<210> SEQ ID NO 207
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 207
auaaccggga gauagugaug a                                             21
```

```
<210> SEQ ID NO 208
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 208
ucaucacuau cucccgguua ucg                                            23

<210> SEQ ID NO 209
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 209
acugaguacc ugaaccggca c                                              21

<210> SEQ ID NO 210
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 210
gugccgguuc agguagucag uca                                            23

<210> SEQ ID NO 211
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 211
ugggagaaca ggguacgaca a                                              21

<210> SEQ ID NO 212
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 212
uugucguacc cuguucuccc agc                                            23

<210> SEQ ID NO 213
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 213
caccgggcau cuucuccucc c                                              21
```

```
<210> SEQ ID NO 214
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 214
gggaggagaa gaugcccggu gcg                                            23

<210> SEQ ID NO 215
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 215
ggacgcuuug ccacgguggu g                                              21

<210> SEQ ID NO 216
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 216
caccaccgug gcaaagcguc ccc                                            23

<210> SEQ ID NO 217
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 217
gaguucggug gggucaugug u                                              21

<210> SEQ ID NO 218
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 218
acacaugacc ccaccgaacu caa                                            23

<210> SEQ ID NO 219
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 219
cgcuuugcca cgguggugga g                                              21

<210> SEQ ID NO 220
```

```
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 220
caccaccacc guggcaaagc guc                                            23

<210> SEQ ID NO 221
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 221
acauccauua uaagcugucg c                                              21

<210> SEQ ID NO 222
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 222
gcgacagcuu auaauggaug uac                                            23

<210> SEQ ID NO 223
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 223
cgagugggau gcgggagaug u                                              21

<210> SEQ ID NO 224
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 224
acaucucccg caucccacuc gua                                            23

<210> SEQ ID NO 225
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 225
ggacgcuuug ccacgguggu g                                              21

<210> SEQ ID NO 226
<211> LENGTH: 23
```

```
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 226
caccaccgug gcaaagcguc ccc                                          23

<210> SEQ ID NO 227
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 227
acauccauua uaagcugucg c                                            21

<210> SEQ ID NO 228
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 228
gcgacagcuu auaauggaug uac                                          23

<210> SEQ ID NO 229
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 229
acaucgcccu guggaugacu g                                            21

<210> SEQ ID NO 230
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 230
cagucaucca cagggcgaug uug                                          23

<210> SEQ ID NO 231
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 231
guacauccau uauaagcugu c                                            21

<210> SEQ ID NO 232
<211> LENGTH: 23
<212> TYPE: RNA
```

```
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 232
gacagcuuau aauggaugua cuu                                              23

<210> SEQ ID NO 233
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 233
cacaccugga uccaggauaa c                                                21

<210> SEQ ID NO 234
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 234
guuauccugg auccaggugu gca                                              23

<210> SEQ ID NO 235
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 235
cgcgacuucg ccgagauguc c                                                21

<210> SEQ ID NO 236
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 236
ggacaucucg gcgaagucgc ggc                                              23

<210> SEQ ID NO 237
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 237
ugacugagua ccugaaccgg c                                                21

<210> SEQ ID NO 238
<211> LENGTH: 23
<212> TYPE: RNA
<213> ORGANISM: Artificial Sequence
```

```
<220> FEATURE:
<223> OTHER INFORMATION: Antisense strand of dsRNA that is complementary
      to a Sequence of the human Bcl-2 gene

<400> SEQUENCE: 238
gccgguucag guacucaguc auc                                            23

<210> SEQ ID NO 239
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 239
uggauccagg auaacggagg c                                              21

<210> SEQ ID NO 240
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 240
gccuccguua uccuggaucc agg                                            23

<210> SEQ ID NO 241
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 241
gcuacgagug ggaugcggga g                                              21

<210> SEQ ID NO 242
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 242
cucccgcauc ccacucguag ccc                                            23

<210> SEQ ID NO 243
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 243
ugaguucggu ggggucaugu g                                              21

<210> SEQ ID NO 244
<211> LENGTH: 23
<212> TYPE: RNA
<213> ORGANISM: Artificial Sequence
<220> FEATURE:
```

```
<223> OTHER INFORMATION: Antisense strand of dsRNA that is complementary
      to a Sequence of the human Bcl-2 gene

<400> SEQUENCE: 244
cacaugaccc caccgaacuc aaa                                              23

<210> SEQ ID NO 245
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 245
guucgguggg gucaugugug u                                                21

<210> SEQ ID NO 246
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 246
acacacauga ccccaccgaa cuc                                              23

<210> SEQ ID NO 247
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 247
gauaacggag gcugggaugc c                                                21

<210> SEQ ID NO 248
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 248
ggcaucccag ccuccguuau ccu                                              23

<210> SEQ ID NO 249
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 249
ccugguggga gcuugcauca c                                                21

<210> SEQ ID NO 250
<211> LENGTH: 23
<212> TYPE: RNA
<213> ORGANISM: Artificial Sequence
<220> FEATURE:
<223> OTHER INFORMATION: Antisense strand of dsRNA that is complementary
``` to a Sequence of the human Bcl-2 gene

<400> SEQUENCE: 250
gugaugcaag cucccaccag ggc                                              23

<210> SEQ ID NO 251
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 251
ggggcuacga gugggaugcg g                                                21

<210> SEQ ID NO 252
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 252
ccgcauccca cucguagccc cuc                                              23

<210> SEQ ID NO 253
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 253
uacgacaacc gggagauagu g                                                21

<210> SEQ ID NO 254
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 254
cacuaucucc cgguugucgu acc                                              23

<210> SEQ ID NO 255
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 255
ggccggcgac gacuucuccc g                                                21

<210> SEQ ID NO 256
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

```
<400> SEQUENCE: 256
cgggagaagu cgucgccggc cug                                              23

<210> SEQ ID NO 257
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 257
gacuucgccg agauguccag c                                                21

<210> SEQ ID NO 258
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 258
gcuggacauc ucggcgaagu cgc                                              23

<210> SEQ ID NO 259
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 259
gguggacaac aucgcccugu g                                                21

<210> SEQ ID NO 260
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 260
cacagggcga uguuguccac cag                                              23

<210> SEQ ID NO 261
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 261
acgaguggga ugcgggagau g                                                21

<210> SEQ ID NO 262
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene
```

```
<400> SEQUENCE: 262
caucucccgc aucccacucg uag                                              23

<210> SEQ ID NO 263
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 263
ccgggcaucu ucuccuccca g                                                21

<210> SEQ ID NO 264
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 264
cugggaggag aagaugcccg gug                                              23

<210> SEQ ID NO 265
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 265
ugaaccggca ccugcacacc u                                                21

<210> SEQ ID NO 266
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 266
aggugugcag gugccgguuc agg                                              23

<210> SEQ ID NO 267
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 267
ggugggguca uguguguggA g                                                21

<210> SEQ ID NO 268
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 268
```

-continued cuccacacac augacccac cga                          23

<210> SEQ ID NO 269
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 269
cuuugaguuc ggugggguca u                           21

<210> SEQ ID NO 270
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 270 augacccac cgaacucaaa gaa                          23

<210> SEQ ID NO 271
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 271
cuggugggag cuugcaucac c                           21

<210> SEQ ID NO 272
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 272
ggugaugcaa gcucccacca ggg                         23

<210> SEQ ID NO 273
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 273
cgccgcgacu ucgccgagau g                           21

<210> SEQ ID NO 274
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 274

```
caucucggcg aagucgcggc ggu                                               23

<210> SEQ ID NO 275
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 275
gcacgcuggg agaacggggu a                                                 21

<210> SEQ ID NO 276
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 276
uaccccguuc ucccagcgug cgc                                               23

<210> SEQ ID NO 277
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 277
aguucggugg ggucaugugu g                                                 21

<210> SEQ ID NO 278
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 278
cacacaugac cccaccgaac uca                                               23

<210> SEQ ID NO 279
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 279
acgcugggag aacggggua cg                                                 21

<210> SEQ ID NO 280
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 280
cguaccccgu ucucccagcg ugc                                               23
```

```
<210> SEQ ID NO 281
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 281
cucaguuugg cccuggugggg a                                              21

<210> SEQ ID NO 282
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 282
ucccaccagg gccaaacuga gcg                                             23

<210> SEQ ID NO 283
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 283
uacauccauu auaagcuguc g                                               21

<210> SEQ ID NO 284
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 284
cgacagcuua uaauggaugu acu                                             23

<210> SEQ ID NO 285
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 285
cgccgagaug uccagccagc u                                               21

<210> SEQ ID NO 286
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 286
agcuggcugg acaucucggc gaa                                             23
```

-continued

```
<210> SEQ ID NO 287
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 287
cucaguuugg cccuggugggg a                                             21

<210> SEQ ID NO 288
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 288
ucccaccagg gccaaacuga gcg                                            23

<210> SEQ ID NO 289
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 289
ccgccaggcc ggcgacgacu u                                              21

<210> SEQ ID NO 290
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 290
aagucgucgc cggccuggcg gag                                            23

<210> SEQ ID NO 291
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 291
gcuuugccac ggugguggag g                                              21

<210> SEQ ID NO 292
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 292
ccuccaccac cguggcaaag cgu                                            23
```

```
<210> SEQ ID NO 293
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 293
aguacaucca uuauaagcug u                                                    21

<210> SEQ ID NO 294
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 294
acagcuuaua auggauguac uuc                                                  23

<210> SEQ ID NO 295
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 295
ccugaaccgg caccugcaca c                                                    21

<210> SEQ ID NO 296
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 296
gugugcaggu gccgguucag gua                                                  23

<210> SEQ ID NO 297
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 297
gccgcgacuu cgccgagaug u                                                    21

<210> SEQ ID NO 298
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 298
acaucucggc gaagucgcgg cgg                                                  23

<210> SEQ ID NO 299
```

<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 299
ggagaacggg guacgacaac c                                             21

<210> SEQ ID NO 300
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 300
gguugucgua ccccguucuc cca                                           23

<210> SEQ ID NO 301
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 301
gagaacgggg uacgacaacc g                                             21

<210> SEQ ID NO 302
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 302
cgguugucgu accccguucu ccc                                           23

<210> SEQ ID NO 303
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 303
gcugcaccug acgcccuuca c                                             21

<210> SEQ ID NO 304
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 304
gugaagggcg ucaggugcag cug                                           23

<210> SEQ ID NO 305
<211> LENGTH: 21

```
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 305
gggagcuugc aucacccugg g                                              21

<210> SEQ ID NO 306
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 306
cccaggguga ugcaagcucc cac                                            23

<210> SEQ ID NO 307
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 307
ccgcgacuuc gccgagaugu c                                              21

<210> SEQ ID NO 308
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 308
gacaucucgg cgaagucgcg gcg                                            23

<210> SEQ ID NO 309
<211> LENGTH: 21
<212> TYPE: RNA
<213> ORGANISM: Artificial Sequence
<220> FEATURE:
<223> OTHER INFORMATION: Sense strand of dsRNA that is complementary to
     a Sequence of the human Bcl-2 gene

<400> SEQUENCE: 309
ccgccgcgac uucgccgaga u                                              21

<210> SEQ ID NO 310
<211> LENGTH: 23
<212> TYPE: RNA
<213> ORGANISM: Artificial Sequence
<220> FEATURE:
<223> OTHER INFORMATION: Antisense strand of dsRNA that is complementary
     to a Sequence of the human Bcl-2 gene

<400> SEQUENCE: 310
aucucggcga agucgcggcg gua                                            23

<210> SEQ ID NO 311
<211> LENGTH: 21
<212> TYPE: RNA
```

```
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 311
ucgccgagau guccagccag c                                           21

<210> SEQ ID NO 312
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 312
gcuggcugga caucucggcg aag                                         23

<210> SEQ ID NO 313
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 313
uugaguucgg uggggucaug u                                           21

<210> SEQ ID NO 314
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 314
acaugacccc accgaacuca aag                                         23

<210> SEQ ID NO 315
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 315
gagugggaug cgggagaugu g                                           21

<210> SEQ ID NO 316
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 316
cacaucuccc gcaucccacu cgu                                         23

<210> SEQ ID NO 317
<211> LENGTH: 21
<212> TYPE: RNA
<213> ORGANISM: Artificial Sequence
```

```
<220> FEATURE:
<223> OTHER INFORMATION: Sense strand of dsRNA that is complementary to
      a Sequence of the human Bcl-2 gene

<400> SEQUENCE: 317
gggaugccuu uguggaacug u                                              21

<210> SEQ ID NO 318
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 318
acaguuccac aaaggcaucc cag                                            23

<210> SEQ ID NO 319
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 319
gcucaguuug gcccuggugg g                                              21

<210> SEQ ID NO 320
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 320
cccaccaggg ccaaacugag cag                                            23

<210> SEQ ID NO 321
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 321
uacgaguggg augcgggaga u                                              21

<210> SEQ ID NO 322
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 322
aucucccgca ucccacucgu agc                                            23

<210> SEQ ID NO 323
<211> LENGTH: 21
<212> TYPE: RNA
<213> ORGANISM: Artificial Sequence
<220> FEATURE:
```

```
<223> OTHER INFORMATION: Sense strand of dsRNA that is complementary to
      a Sequence of the human Bcl-2 gene

<400> SEQUENCE: 323
cgcaccgggc aucuucuccu c                                                    21

<210> SEQ ID NO 324
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 324
gaggagaaga ugcccggugc ggg                                                  23

<210> SEQ ID NO 325
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 325
aggccggcga cgacuucucc c                                                    21

<210> SEQ ID NO 326
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 326
gggagaaguc gucgccggcc ugg                                                  23

<210> SEQ ID NO 327
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 327
aucacccugg gugccuaucu g                                                    21

<210> SEQ ID NO 328
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 328
cagauaggca cccaggguga ugc                                                  23

<210> SEQ ID NO 329
<211> LENGTH: 21
<212> TYPE: RNA
<213> ORGANISM: Artificial Sequence
<220> FEATURE:
<223> OTHER INFORMATION: Sense strand of dsRNA that is complementary to
``` a Sequence of the human Bcl-2 gene

<400> SEQUENCE: 329
ccaggccggc gacgacuucu c						21

<210> SEQ ID NO 330
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 330
gagaagucgu cgccggccug gcg						23

<210> SEQ ID NO 331
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 331
gccaggccgg cgacgacuuc u						21

<210> SEQ ID NO 332
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 332
agaagucguc gccggccugg cgg						23

<210> SEQ ID NO 333
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 333
caccugacgc ccuucaccgc g						21

<210> SEQ ID NO 334
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 334
cgcggugaag ggcgucaggu gca						23

<210> SEQ ID NO 335
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

```
<400> SEQUENCE: 335
guuuggcccu gugggagcu u                                          21

<210> SEQ ID NO 336
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 336
aagcucccac cagggccaaa cug                                       23

<210> SEQ ID NO 337
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 337
ugccuuugug gaacuguacg g                                         21

<210> SEQ ID NO 338
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 338
ccguacaguu ccacaaaggc auc                                       23

<210> SEQ ID NO 339
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 339
cugcaccuga cgcccuucac c                                         21

<210> SEQ ID NO 340
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 340
ggugaagggc gucaggugca gcu                                       23

<210> SEQ ID NO 341
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene
```

<400> SEQUENCE: 341
aacaucgccc uguggaugac u                                          21

<210> SEQ ID NO 342
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 342
agucauccac agggcgaugu ugu                                        23

<210> SEQ ID NO 343
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 343
ugcucaguuu ggcccuggug g                                          21

<210> SEQ ID NO 344
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 344
ccaccagggc caaacucagc aga                                        23

<210> SEQ ID NO 345
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 345
guggagagcg ucaaccggga g                                          21

<210> SEQ ID NO 346
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 346
cucccgguug acgcucucca cac                                        23

<210> SEQ ID NO 347
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 347
ugaguaccug aaccggcacc u                                              21

<210> SEQ ID NO 348
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 348
aggugccggu ucagguacuc agu                                            23

<210> SEQ ID NO 349
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 349
ugguggacaa caucgcccug u                                              21

<210> SEQ ID NO 350
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 350
acagggcgau guguccacc agg                                             23

<210> SEQ ID NO 351
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 351
acgcuuugcc acgguggugg a                                              21

<210> SEQ ID NO 352
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 352
uccaccaccg uggcaaagcg ucc                                            23

<210> SEQ ID NO 353
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 353

```
gcaccugacg cccuucaccg c                                              21
```

<210> SEQ ID NO 354
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 354

```
gcggugaagg gcgucaggug cag                                            23
```

<210> SEQ ID NO 355
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 355

```
ggugggagcu ugcaucaccc u                                              21
```

<210> SEQ ID NO 356
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 356

```
agggugaugc aagcucccac cag                                            23
```

<210> SEQ ID NO 357
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 357

```
ggauccagga uaacggaggc u                                              21
```

<210> SEQ ID NO 358
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 358

```
agccuccguu auccuggauc cag                                            23
```

<210> SEQ ID NO 359
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 359

```
aacaggguac gauaaccggg a                                              21
```

<210> SEQ ID NO 360
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 360
ucccgguuau cguacccugu ucu                                            23

<210> SEQ ID NO 361
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 361
ggauaacgga ggcugggaug c                                              21

<210> SEQ ID NO 362
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 362
gcaucccagc cuccguuauc cug                                            23

<210> SEQ ID NO 363
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 363
uuuggcccug gugggagcuu g                                              21

<210> SEQ ID NO 364
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 364
caagcuccca ccagggccaa acu                                            23

<210> SEQ ID NO 365
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 365
gaacagggua cgauaaccgg g                                              21

```
<210> SEQ ID NO 366
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 366
cccgguuauc guacccagaa cuc                                              23

<210> SEQ ID NO 367
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 367
ugcaccugac gcccuucacc g                                                21

<210> SEQ ID NO 368
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 368
cggugaaggg cgucaggugc agc                                              23

<210> SEQ ID NO 369
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 369
uuuggcccug gugggagcuu g                                                21

<210> SEQ ID NO 370
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 370
caagcuccca ccagggccaa acu                                              23

<210> SEQ ID NO 371
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 371
acaggguacg auaaccggga g                                                21
```

<210> SEQ ID NO 372
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 372
cucccgguua ucguacccug uuc                                            23

<210> SEQ ID NO 373
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 373
caggccggcg acgacuucuc c                                              21

<210> SEQ ID NO 374
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 374
ggagaagucg ucgccggccu ggc                                            23

<210> SEQ ID NO 375
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 375
gccggcgacg acuucucccg c                                              21

<210> SEQ ID NO 376
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 376
gcgggagaag ucgucgccgg cuu                                            23

<210> SEQ ID NO 377
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 377
acgacuucuc ccgccgcuac c                                              21

<210> SEQ ID NO 378

<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 378
gguagcggcg ggagaagucg ucg                                              23

<210> SEQ ID NO 379
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 379
uucggugggg ucaugugugu g                                                21

<210> SEQ ID NO 380
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 380
cacacacaug accccaccga acu                                              23

<210> SEQ ID NO 381
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 381
gcugggagaa caggguacga c                                                21

<210> SEQ ID NO 382
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 382
gucguacccu guucucccag cgu                                              23

<210> SEQ ID NO 383
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 383
ccgcaccggg caucuucucc u                                                21

<210> SEQ ID NO 384
<211> LENGTH: 23

```
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 384
aggagaagau gcccggugcg ggg                                          23

<210> SEQ ID NO 385
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 385
cgacuucucc cgccgcuacc g                                            21

<210> SEQ ID NO 386
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 386
cgguagcggc gggagaaguc guc                                          23

<210> SEQ ID NO 387
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 387
uugcaucacc cugggugccu a                                            21

<210> SEQ ID NO 388
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 388
uaggcaccca gggugaugca agc                                          23

<210> SEQ ID NO 389
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 389
uugcaucacc cugggugccu a                                            21

<210> SEQ ID NO 390
<211> LENGTH: 23
<212> TYPE: RNA
```

```
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 390
uaggcaccca gggugaugca agc                                              23

<210> SEQ ID NO 391
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 391
guggacaaca ucgcccugug g                                                21

<210> SEQ ID NO 392
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 392
ccacagggcg auguugucca cca                                              23

<210> SEQ ID NO 393
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 393
gcaucuucuc cucccagccc g                                                21

<210> SEQ ID NO 394
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 394
cgggcuggga ggagaagaug ccc                                              23

<210> SEQ ID NO 395
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 395
cuuugccacg gugguggagg a                                                21

<210> SEQ ID NO 396
<211> LENGTH: 23
<212> TYPE: RNA
<213> ORGANISM: Artificial Sequence
```

```
<220> FEATURE:
<223> OTHER INFORMATION: Antisense strand of dsRNA that is complementary
      to a Sequence of the human Bcl-2 gene

<400> SEQUENCE: 396
uccuccacca ccguggcaaa gcg                                              23

<210> SEQ ID NO 397
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 397
gcaccgggca ucuucuccuc c                                                21

<210> SEQ ID NO 398
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 398
ggaggagaag augcccggug cgg                                              23

<210> SEQ ID NO 399
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 399
uguacggccc cagcaugcgg c                                                21

<210> SEQ ID NO 400
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 400
gccgcaugcu ggggccguac agu                                              23

<210> SEQ ID NO 401
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 401
acucugcuca guuuggcccu g                                                21

<210> SEQ ID NO 402
<211> LENGTH: 23
<212> TYPE: RNA
<213> ORGANISM: Artificial Sequence
<220> FEATURE:
```

```
<223> OTHER INFORMATION: Antisense strand of dsRNA that is complementary
      to a Sequence of the human Bcl-2 gene

<400> SEQUENCE: 402
cagggccaaa cugagcagag ucu                                              23

<210> SEQ ID NO 403
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 403
uuggcccugg ugggagcuug c                                                21

<210> SEQ ID NO 404
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 404
gcaagcuccc accagggcca aac                                              23

<210> SEQ ID NO 405
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 405
uggcccuggu gggagcuugc a                                                21

<210> SEQ ID NO 406
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 406
ugcaagcucc caccagggcc aaa                                              23

<210> SEQ ID NO 407
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 407
gcaucacccu gggugccuau c                                                21

<210> SEQ ID NO 408
<211> LENGTH: 23
<212> TYPE: RNA
<213> ORGANISM: Artificial Sequence
<220> FEATURE:
<223> OTHER INFORMATION: Antisense strand of dsRNA that is complementary
``` to a Sequence of the human Bcl-2 gene

<400> SEQUENCE: 408
gauaggcacc cagggugaug caa                                            23

<210> SEQ ID NO 409
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 409
uggugggagc uugcaucacc c                                              21

<210> SEQ ID NO 410
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 410
gggugaugca agcucccacc agg                                            23

<210> SEQ ID NO 411
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 411
uacggcccca gcaugcggcc u                                              21

<210> SEQ ID NO 412
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 412
aggccgcaug cugggggccgu aca                                            23

<210> SEQ ID NO 413
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 413
ugggaugccu uuguggaacu g                                              21

<210> SEQ ID NO 414
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene -continued

<400> SEQUENCE: 414
caguuccaca aaggcauccc agc                                          23

<210> SEQ ID NO 415
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 415
agaacagggu acgauaaccg g                                            21

<210> SEQ ID NO 416
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 416
ccgguuaucg uacccuguuc ucc                                          23

<210> SEQ ID NO 417
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 417
gacuucuccc gccgcuaccg c                                            21

<210> SEQ ID NO 418
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 418
gcgguagcgg cgggagaagu cgu                                          23

<210> SEQ ID NO 419
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 419
agacucugcu caguuuggcc c                                            21

<210> SEQ ID NO 420
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

```
<400> SEQUENCE: 420
gggccaaacu gagcagaguc uuc                                              23

<210> SEQ ID NO 421
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 421
ugggagcuug caucacccug g                                                21

<210> SEQ ID NO 422
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 422
ccagggugau gcaagcuccc acc                                              23

<210> SEQ ID NO 423
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 423
gugggagcuu gcaucacccu g                                                21

<210> SEQ ID NO 424
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 424
cagggugaug caagcuccca cca                                              23

<210> SEQ ID NO 425
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 425
cgccaggccg gcgacgacuu c                                                21

<210> SEQ ID NO 426
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 426
```
gaagucgucg ccggccuggc gga                                          23

<210> SEQ ID NO 427
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 427
gaggggcuac gagugggaug c                                            21

<210> SEQ ID NO 428
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 428
gcaucccacu cguagccccu cug                                          23

<210> SEQ ID NO 429
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 429
acacgcccca uccagccgca u                                            21

<210> SEQ ID NO 430
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 430
augcggcugg auggggcgug ugc                                          23

<210> SEQ ID NO 431
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 431
agcuugcauc acccuggguG c                                            21

<210> SEQ ID NO 432
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 432

-continued gcacccaggg ugaugcaagc ucc                                              23

<210> SEQ ID NO 433
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 433
cagaggggcu acgaguggga u                                                21

<210> SEQ ID NO 434
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 434
aucccacucg uagccccucu gcg                                              23

<210> SEQ ID NO 435
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 435
cuguacggcc ccagcaugcg g                                                21

<210> SEQ ID NO 436
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 436
ccgcaugcug gggccguaca guu                                              23

<210> SEQ ID NO 437
<211> LENGTH: 21
<212> TYPE: RNA
<213> ORGANISM: Artificial Sequence
<220> FEATURE:
<223> OTHER INFORMATION: Sense strand of dsRNA that is complementary to
      a Sequence of the human Bcl-2 gene

<400> SEQUENCE: 437
cuugcaucac ccugggugcc u                                                21

<210> SEQ ID NO 438
<211> LENGTH: 23
<212> TYPE: RNA
<213> ORGANISM: Artificial Sequence
<220> FEATURE:
<223> OTHER INFORMATION: Antisense strand of dsRNA that is complementary
      to a Sequence of the human Bcl-2 gene

<400> SEQUENCE: 438
aggcacccag ggugaugcaa gcu                                              23

<210> SEQ ID NO 439
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 439
ugcaucaccc ugggugccua u                                              21

<210> SEQ ID NO 440
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 440
auaggcaccc agggugaugc aag                                            23

<210> SEQ ID NO 441
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 441
ccugggugcc uaucugggcc a                                              21

<210> SEQ ID NO 442
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 442
uggcccagau aggcacccag ggu                                            23

<210> SEQ ID NO 443
<211> LENGTH: 21
<212> TYPE: RNA
<213> ORGANISM: Artificial Sequence
<220> FEATURE:
<223> OTHER INFORMATION: Sense strand of dsRNA that is complementary to
a Sequence of the human Bcl-2 gene

<400> SEQUENCE: 443
uuauaagcug ucgcagaggg g                                              21

<210> SEQ ID NO 444
<211> LENGTH: 23
<212> TYPE: RNA
<213> ORGANISM: Artificial Sequence
<220> FEATURE:
<223> OTHER INFORMATION: Antisense strand of dsRNA that is complementary
to a Sequence of the human Bcl-2 gene

<400> SEQUENCE: 444
ccccucugcg acagcuuaua aug                                            23

```
<210> SEQ ID NO 445
<211> LENGTH: 21
<212> TYPE: RNA
<213> ORGANISM: Artificial Sequence
<220> FEATURE:
<223> OTHER INFORMATION: Sense strand of control dsRNA

<400> SEQUENCE: 445
gaugaggauc guuucgcaug a                                              21

<210> SEQ ID NO 446
<211> LENGTH: 23
<212> TYPE: RNA
<213> ORGANISM: Artificial Sequence
<220> FEATURE:
<223> OTHER INFORMATION: Antisense strand of control dsRNA

<400> SEQUENCE: 446
ucaugcgaaa cgauccucau ccu                                            23

<210> SEQ ID NO 447
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 447
gacugaguac cugaaccggc a                                              21

<210> SEQ ID NO 448
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate
      modification

<400> SEQUENCE: 448
ugccgguuca gguacucagu cau                                            23

<210> SEQ ID NO 449
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 449
cgauaaccgg gagauaguga u                                              21

<210> SEQ ID NO 450
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
```

```
<222> LOCATION: 21
<223> OTHER INFORMATION: gm = 2'-O-methylguanosine-5'-phosphate
      modification
<220> FEATURE:
<221> NAME/KEY: modified_base
<222> LOCATION: 22
<223> OTHER INFORMATION: um = 2'-O-methyluridine-5'-phosphate
      modification

<400> SEQUENCE: 450
aucacuaucu cccgguuauc gua                                                 23

<210> SEQ ID NO 451
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 451
gguacgauaa ccgggagaua g                                                   21

<210> SEQ ID NO 452
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21, 22
<223> OTHER INFORMATION: cm = 2'-O-methylcytidine-5'-phosphate
      modification

<400> SEQUENCE: 452
cuaucucccg guuaucguac ccc                                                 23

<210> SEQ ID NO 453
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 453
guacgauaac cgggagauag u                                                   21

<210> SEQ ID NO 454
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21, 22
<223> OTHER INFORMATION: cm = 2'-O-methylcytidine-5'-phosphate
      modification

<400> SEQUENCE: 454
acuaucuccc gguuaucgua ccc                                                 23

<210> SEQ ID NO 455
<211> LENGTH: 21
<212> TYPE: RNA
<213> ORGANISM: Artificial Sequence
<220> FEATURE:
<223> OTHER INFORMATION: Synthetically generated siRNA
```

```
<400> SEQUENCE: 455
uguggaugac ugaguaccug a                                    21

<210> SEQ ID NO 456
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: am = 2'-O-methyladenosine-5'-phosphate
      modification
<220> FEATURE:
<221> NAME/KEY: modified_base
<222> LOCATION: 22
<223> OTHER INFORMATION: gm = 2'-O-methylguanosine-5'-phosphate
      modification

<400> SEQUENCE: 456
ucagguacuc agucauccac agg                                  23

<210> SEQ ID NO 457
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 457
guggaugacu gaguaccuga a                                    21

<210> SEQ ID NO 458
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate
      modification

<400> SEQUENCE: 458
uucagguacu cagucaucca cag                                  23

<210> SEQ ID NO 459
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 459
cccuguggau gacugaguac c                                    21

<210> SEQ ID NO 460
<211> LENGTH: 23
<212> TYPE: RNA
<213> ORGANISM: Artificial Sequence
<220> FEATURE:
<223> OTHER INFORMATION: Synthetically generated siRNA
```

```
<220> FEATURE:
<221> NAME/KEY: modified_base
<222> LOCATION: 21
<223> OTHER INFORMATION: gm = 2'-O-methylguanosine-5'-phosphate
      modification
<220> FEATURE:
<221> NAME/KEY: modified_base
<222> LOCATION: 22
<223> OTHER INFORMATION: cm = 2'-O-methylcytidine-5'-phosphate
      modification

<400> SEQUENCE: 460
gguacucagu cauccacagg gcg                                          23

<210> SEQ ID NO 461
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 461
accgggcauc uucuccuccc a                                            21

<210> SEQ ID NO 462
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methyluridine-5'-phosphate
      modification
<220> FEATURE:
<221> NAME/KEY: modified_base
<222> LOCATION: 22
<223> OTHER INFORMATION: gm = 2'-O-methylguanosine-5'-phosphate
      modification

<400> SEQUENCE: 462
ugggaggaga agaugcccgg ugc                                          23

<210> SEQ ID NO 463
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 463
ggccuucuuu gaguucggug g                                            21

<210> SEQ ID NO 464
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate
      modification
```

<400> SEQUENCE: 464
ccaccgaacu caaagaaggc cac                                           23

<210> SEQ ID NO 465
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 465
gacugaguac cugaaccggc a                                             21

<210> SEQ ID NO 466
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 22
<223> OTHER INFORMATION: adenosine-5'- phosphorothioate modification
<220> FEATURE:
<221> NAME/KEY: modified_base
<222> LOCATION: 23
<223> OTHER INFORMATION: uridine-5'-phosphorothioate modification

<400> SEQUENCE: 466
ugccgguuca gguacucagu cau                                           23

<210> SEQ ID NO 467
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 467
cgauaaccgg gagauaguga u                                             21

<210> SEQ ID NO 468
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 22
<223> OTHER INFORMATION: uridine-5'-phosphorothioate modification
<220> FEATURE:
<221> NAME/KEY: modified_base
<222> LOCATION: 23
<223> OTHER INFORMATION: adenosine-5'-
    phosphorothioate modification

<400> SEQUENCE: 468
aucacuaucu cccgguuauc gua                                           23

<210> SEQ ID NO 469
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 469
cccuguggau gacugaguac c                                              21

<210> SEQ ID NO 470
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 22
<223> OTHER INFORMATION: cytidine-5'- phosphorothioate modification
<220> FEATURE:
<221> NAME/KEY: modified_base
<222> LOCATION: 23
<223> OTHER INFORMATION: guanosine-5'-phosphorothioate modification

<400> SEQUENCE: 470
gguacucagu cauccacagg gcg                                            23

<210> SEQ ID NO 471
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 471
ggccuucuuu gaguucggug g                                              21

<210> SEQ ID NO 472
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 22
<223> OTHER INFORMATION: adenosine-5'-phosphorothioate modification
<220> FEATURE:
<221> NAME/KEY: modified_base
<222> LOCATION: 23
<223> OTHER INFORMATION: cytidine-5'-phosphorothioate modification

<400> SEQUENCE: 472
ccaccgaacu caaagaaggc cac                                            23

<210> SEQ ID NO 473
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 2, 18, 20, 21
<223> OTHER INFORMATION: guanosine-5'-phosphorothioate modification
<220> FEATURE:
<221> NAME/KEY: modified_base
<222> LOCATION: 3, 4
<223> OTHER INFORMATION: cytidine-5'-phosphorothioate modification
<220> FEATURE:
<221> NAME/KEY: modified_base
<222> LOCATION: 5, 19
<223> OTHER INFORMATION: uridine-5'-phosphorothioate modification

<400> SEQUENCE: 473
ggccuucuuu gaguucggug g                                              21

```
<210> SEQ ID NO 474
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 1, 3, 4, 18, 20
<223> OTHER INFORMATION: cytidine-5'-phosphorothioate modification
<220> FEATURE:
<221> NAME/KEY: modified_base
<222> LOCATION: 2, 19
<223> OTHER INFORMATION: adenosine-5'-phosphorothioate modification

<400> SEQUENCE: 474
ccaccgaacu caaagaaggc cac                                              23

<210> SEQ ID NO 475
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 475
ggccuucuuu gaguucggug g                                                21

<210> SEQ ID NO 476
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate

<400> SEQUENCE: 476
ccaccgaacu caaagaaggc cac                                              23

<210> SEQ ID NO 477
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 477
ggccuucuuu gaguucggug g                                                21

<210> SEQ ID NO 478
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
```

<223> OTHER INFORMATION: am = 2'-O-methyladenosine-5'-phosphate

<400> SEQUENCE: 478
ccaccgaacu caaagaaggc cac                                           23

<210> SEQ ID NO 479
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 479
ggccuucuuu gaguucggug g                                             21

<210> SEQ ID NO 480
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate

<400> SEQUENCE: 480
ccaccgaacu caaagaaggc cac                                           23

<210> SEQ ID NO 481
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 21
<223> OTHER INFORMATION: n = guanine conjugated choresterol

<400> SEQUENCE: 481
ggccuucuuu gaguucggug n                                             21

<210> SEQ ID NO 482
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'- phosphorothioate
      modification
<220> FEATURE:
<221> NAME/KEY: modified_base
<222> LOCATION: 22
<223> OTHER INFORMATION: am = 2'-O-methyladenosine-5'-phosphorothioate
      modification

<400> SEQUENCE: 482
ccaccgaacu caaagaaggc cac                                           23

<210> SEQ ID NO 483

-continued

```
<211> LENGTH: 21
<212> TYPE: RNA
<213> ORGANISM: Artificial Sequence
<220> FEATURE:
<223> OTHER INFORMATION: Synthetically generated siRNA

<400> SEQUENCE: 483
ggccuucuuu gaguucggug g                                              21

<210> SEQ ID NO 484
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 2, 3, 4, 20
<223> OTHER INFORMATION: cytidine-5'-phosphorothioate modification
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate
      modification

<400> SEQUENCE: 484
ccaccgaacu caaagaaggc cac                                            23

<210> SEQ ID NO 485
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 2, 18, 20, 21
<223> OTHER INFORMATION: guanosine-5'-phosphorothioate modification
<220> FEATURE:
<221> NAME/KEY: modified_base
<222> LOCATION: 3, 4
<223> OTHER INFORMATION: cytidine-5'-phosphorothioate modification
<220> FEATURE:
<221> NAME/KEY: modified_base
<222> LOCATION: 5, 19
<223> OTHER INFORMATION: uridine-5'-phosphorothioate modification

<400> SEQUENCE: 485
ggccuucuuu gaguucggug g                                              21

<210> SEQ ID NO 486
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 22
<223> OTHER INFORMATION: am = 2'-O-methyladenosine-5'-phosphate
      modification

<400> SEQUENCE: 486
```

```
ccaccgaacu caaagaaggc cac                                             23

<210> SEQ ID NO 487
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = guanine phosphorothioate modification
      conjugated choresterol
<220> FEATURE:
<221> NAME/KEY: misc_feature
<222> LOCATION: 2, 3, 4, 5, 6, 7, 8, 9, 10, 11, 12, 13, 14,
      15, 16, 17, 18, 19, 20, 21
<223> OTHER INFORMATION: nucleoside-5'-phosphorothioate modification

<400> SEQUENCE: 487
ngccuucuuu gaguucggug g                                               21

<210> SEQ ID NO 488
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = guanine phosphorothioate modification
      conjugated choresterol
<220> FEATURE:
<221> NAME/KEY: modified_base
<222> LOCATION: 2, 18, 20, 21
<223> OTHER INFORMATION: guanosine-5'-
      phosphorothioate modification
<220> FEATURE:
<221> NAME/KEY: modified_base
<222> LOCATION: 3, 4
<223> OTHER INFORMATION: cytidine-5'-phosphorothioate modification
<220> FEATURE:
<221> NAME/KEY: modified_base
<222> LOCATION: 5, 19
<223> OTHER INFORMATION: uridine-5'-phosphorothioate modification

<400> SEQUENCE: 488
ngccuucuuu gaguucggug g                                               21

<210> SEQ ID NO 489
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 1
<223> OTHER INFORMATION: n = cytadine phosphorothioate modification
      conjugated choresterol
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
<222> LOCATION: 21
<223> OTHER INFORMATION: cm = 2'-O-methylcytidine-5'-phosphate
      modification
<220> FEATURE:
<221> NAME/KEY: modified_base
```

```
<222> LOCATION: 22
<223> OTHER INFORMATION: am = 2'-O-methyladenosine-5'- phosphorothioate
      modification
<220> FEATURE:
<221> NAME/KEY: modified_base
<222> LOCATION: 23
<223> OTHER INFORMATION: cytidine-5'-phosphorothioate modification

<400> SEQUENCE: 489
ncaccgaacu caaagaaggc cac                                              23

<210> SEQ ID NO 490
<211> LENGTH: 30
<212> TYPE: DNA
<213> ORGANISM: Artificial Sequence
<220> FEATURE:
<223> OTHER INFORMATION: Primer

<400> SEQUENCE: 490
aaactcgagg cgcacgctgg gagaacgggg                                       30

<210> SEQ ID NO 491
<211> LENGTH: 30
<212> TYPE: DNA
<213> ORGANISM: Artificial Sequence
<220> FEATURE:
<223> OTHER INFORMATION: Primer

<400> SEQUENCE: 491
aaatctagat cacttgtggc tcagataggc                                       30
```

COMPOSITIONS AND METHODS FOR INHIBITING EXPRESSION OF ANTI-APOPTOTIC GENES

RELATED APPLICATIONS

This application is a continuation in part of U.S. application Ser. No. 10/941,663, filed Sep. 15, 2004, which is a continuation-in-part of U.S. application Ser. No. 10/384,260, filed Mar. 7, 2003, which is a continuation-in-part of International Application No. PCT/EP02/00151, which designated the United States and was filed Jan. 9, 2002, and which claims the benefit of German Patent No. 101 00 586.5, filed Jan. 9, 2001. The entire teachings of the above applications are incorporated herein by reference.

SUBMISSIONS ON COMPACT DISC

A Sequence Listing as required under 37 C.F.R. § 1.821(c) is submitted on a compact disc as permitted under 37 C.F.R. § 1.52(e). The data file on the compact disc has the file name 14174-123001.txt, contains 125 KB of data, and was created on Dec. 2, 2005. The contents of the compact disc, ASCII text file, are hereby incorporated by reference in their entirety.

Duplicate copies (Copy 1 and Copy 2) of the compact disc are submitted. The contents of Copy 1 and Copy 2 are identical.

FIELD OF THE INVENTION

This invention relates to double-stranded ribonucleic acid (dsRNA), and its use in mediating RNA interference to inhibit the expression of an anti-apoptotic target gene, such as a Bcl gene.

BACKGROUND OF THE INVENTION

Many diseases, including cancers, arise from the abnormal over-expression or -activity of a particular gene, a group of genes, or a mutant form of protein. The therapeutic benefits of being able to selectively silence the expression of these genes is obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and I. Gibson, *Blood* (1998) 91:371). However, both of these agents have inherent limitations. Antisense approaches, using either single-stranded RNA or DNA, act in a 1:1 stoichiometric relationship and thus have low efficacy (Skorski et al., supra). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.).

Briefly, the RNA III Dicer enzyme processes dsRNA exceeding a certain length into small interfering RNA (siRNA) of approximately 22 nucleotides. One strand of the siRNA (the "guide strand") then serves as a guide sequence to induce cleavage of messenger RNAs (mRNAs) comprising a nucleotide sequence which is at least partially complementary to the sequence of the guide strand by an RNA-induced silencing complex RISC (Hammond, S. M., et al., Nature (2000) 404:293-296). The guide strand is not cleaved or otherwise degraded in this process, and the RISC comprising the guide strand can subsequently effect the degradation of further mRNAs by sequence specific cleavage. In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

Gautschi et al. report that the expression levels of the anti-apoptotic proteins Bcl-1 and Bcl-xL are elevated during the development and progression of tumors (Gautschi, O., et al., *J. Natl. Cancer Inst.* (2001) 93:463-471). Tumor growth (but not size) was reduced by approximately 50-60% in nude mice treated with a combination of single-stranded antisense oligoribonucleotides targeted to Bcl-2 and Bcl-xL genes. However, because of the 1:1 stoichiometric relationship and thus low efficiency of antisense RNA, the anti-Bcl treatment required 20 milligrams of antisense RNA per kilogram body weight of recipient mouse per day. Producing therapeutically sufficient amounts of RNA is not only expensive, but single-stranded antisense RNA is highly susceptible to degradation by serum proteases, thus resulting in a short in vivo half-life.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target anti-apoptotic gene at a low dose, would be highly desirable. Compositions comprising such agents would be useful for treating diseases caused by the expression of these genes.

SUMMARY OF THE INVENTION

The present invention discloses double-stranded ribonucleic acid (dsRNA), as well as compositions and methods for inhibiting the expression of a target gene, such as an anti-apoptotic gene, in a cell using the dsRNA. The present invention also discloses compositions and methods for treating diseases caused by the expression of a target anti-apoptotic gene (e.g., a Bcl gene). The dsRNA of the invention comprises an RNA strand (the antisense strand) having a region which is less than 30 nucleotides in length and is substantially complementary to at least part of an mRNA transcript of an anti-apoptotic target gene, such as Bcl-2, Bcl-XL, Bcl-w, Mcl-1 and A1.

In one aspect, the invention provides for a double-stranded ribonucleic acid (dsRNA) for inhibiting the expression of a bcl-2 gene in a cell. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding bcl-2, and the region of complementarity is less than 30 nucleotides in length. The dsRNA, upon contacting with a cell expressing the bcl-2, inhibits the expression of the bcl-2 gene by at least 20%.

In one embodiment, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In a another preferred embodiment, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a second aspect, the invention provides for a cell comprising a double-stranded ribonucleic acid (dsRNA) for inhibiting the expression of a bcl-2 gene in a cell. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding bcl-2, and the region of complementarity is less than 30 nucleotides in length. The dsRNA, upon contacting with a cell expressing the bcl-2, inhibits the expression of the bcl-2 gene by at least 20%.

In one embodiment of said second aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In another preferred embodiment of said second aspect of the invention, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a third aspect, the present invention provides for a pharmaceutical composition for inhibiting the expression of the bcl-2 gene in an organism, comprising a dsRNA and a pharmaceutically acceptable carrier. The dsRNA comprises at least two sequences that are complementary to each other, wherein a sense strand comprises a first sequence and an antisense strand comprises a second sequence. The antisense strand comprises a region of complementarity which is substantially complementary to at least a part of an mRNA encoding bcl-2. The region of complementarity is less than 30 nucleotides in length. The dsRNA, upon contact with a cell expressing the bcl-2, inhibits the expression of the bcl-2 gene by at least 20%.

In one embodiment of said third aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In a another preferred embodiment of said third aspect of the invention, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a fourth aspect of the invention, a method is provided for inhibiting the expression of the bcl-2 gene in a cell, comprising the following steps:
(a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoding bcl-2, and wherein the region of complementarity is less than 30 nucleotides in length and wherein the dsRNA, upon contact with a cell expressing the bcl-2, inhibits expression of the bcl-2 gene by at least 20%; and
(b) maintaining the cell produced in step (a) for a time sufficient to obtain degradation of the mRNA transcript of the bcl-2 gene, thereby inhibiting expression of the target gene in the cell.

In one embodiment of said fourth aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In a another preferred embodiment of said fourth aspect of the invention, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a fifth aspect, the invention provides for a method of suppressing growth of a cancer cell, comprising contacting the cell with a dsRNA. The dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of an mRNA encoding bcl-2, and wherein the region of complementarity is less than 30 nucleotides in length. The dsRNA, upon contact with a cell expressing the bcl-2, inhibits expression of the bcl-2 gene by at least 20%.

In one embodiment of said fifth aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In a another preferred embodiment of said fifth aspect of the invention, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a sixth aspect of the invention, a method is provided for treating, preventing or managing cancer comprising administering to a patient in need of such treatment, prevention or management a therapeutically or prophylactically effective amount of a dsRNA. The dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of an mRNA encoding bcl-2. The region of complementarity is less than 30 nucleotides in length. The dsRNA, upon contact with a cell expressing the bcl-2, inhibits expression of the bcl-2 gene by at least 20%.

In one embodiment of said sixth aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In a another preferred embodiment of said sixth aspect of the invention, said dsRNA comprises at least one modified nucleotide. Said modified nucleotide may be chosen from the group of: a 2'-O-methyl modified nucleotide, a nucleotide comprising a 5'-phosphorothioate group, and a terminal nucleotide linked to a cholesteryl derivative or dodecanoic acid bisdecylamide group. Alternatively, said modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of SEQ ID NOs: (n) the said second sequence is selected from the group consisting of SEQ ID NOs: (n+1), wherein n is an odd number in the range of 447-474. In another preferred embodiment, the said first sequence is selected from the group consisting of SEQ ID NOs: (n) and said second sequence is selected from the group consisting of SEQ ID NOs: (n+1), wherein n is an odd number selected from the group consisting of: 475, 477, 471, 483, 485, 487, 489, 497, 499, 503.

In a seventh aspect, the invention provides for a vector for inhibiting the expression of a bcl-2 gene in a cell, comprising a regulatory sequence operably linked to a nucleotide sequence that encodes at least one strand of a dsRNA. One of the strands of the dsRNA is substantially complementary to at least a part of an mRNA encoding bcl-2 and the dsRNA is less than 50, preferably less than 30 base pairs in length. Upon introduction of the vector into a cell expressing the bcl-2, and subsequent expression of the at least one strand of the dsRNA from the vector inside the cell, the dsRNA inhibits the expression of the bcl-2 gene by at least 20%.

In one embodiment of said seventh aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

In an eighth embodiment, the invention provides for a cell comprising a vector for inhibiting the expression of a bcl-2 gene in a cell. The vector comprises a regulatory sequence operably linked to a nucleotide sequence that encodes at least one strand of a dsRNA. One of the strands of the dsRNA is substantially complementary to at least a part of a mRNA encoding bcl-2 and (the dsRNA is less than 30 base pairs in length) Upon expression of the at least one strand of a dsRNA from the vector inside the cell, the dsRNA inhibits the expression of the bcl-2 gene in the cell by at least 20%.

In one embodiment of said eighth aspect of the invention, the first sequence of the dsRNA is selected from the group consisting of SEQ ID NOs: (n) and the second sequence is selected from the group consisting of SEQ ID NOs: (n+1), wherein n is an odd number in the range of 7-295. In another embodiment, n is an odd number in the range of 7-209; in this embodiment, the dsRNA inhibits the expression of the bcl-2 gene by at least 30%. In yet another embodiment, n is an odd number in the range of 7-169; in this embodiment, the dsRNA inhibits the expression of the bcl-2 gene by at least 40%. n can also be an odd number in the range of 7-129; in this embodiment, the dsRNA inhibits the expression of the bcl-2 gene by at least 50%. Preferably, n is an odd number in the range of 7-67; in this embodiment, the dsRNA inhibits the expression of the bcl-2 gene by at least 60%. More preferably, n is an odd number in the range of 7-31; in this embodiment, the dsRNA inhibits the expression of the bcl-2 gene by at least 70%. Most preferably, n is an odd number in the range of 7-11; in this embodiment, the dsRNA inhibits the expression of the bcl-2 gene by at least 80%.

DETAILED DESCRIPTION OF THE INVENTION

Figure 1:
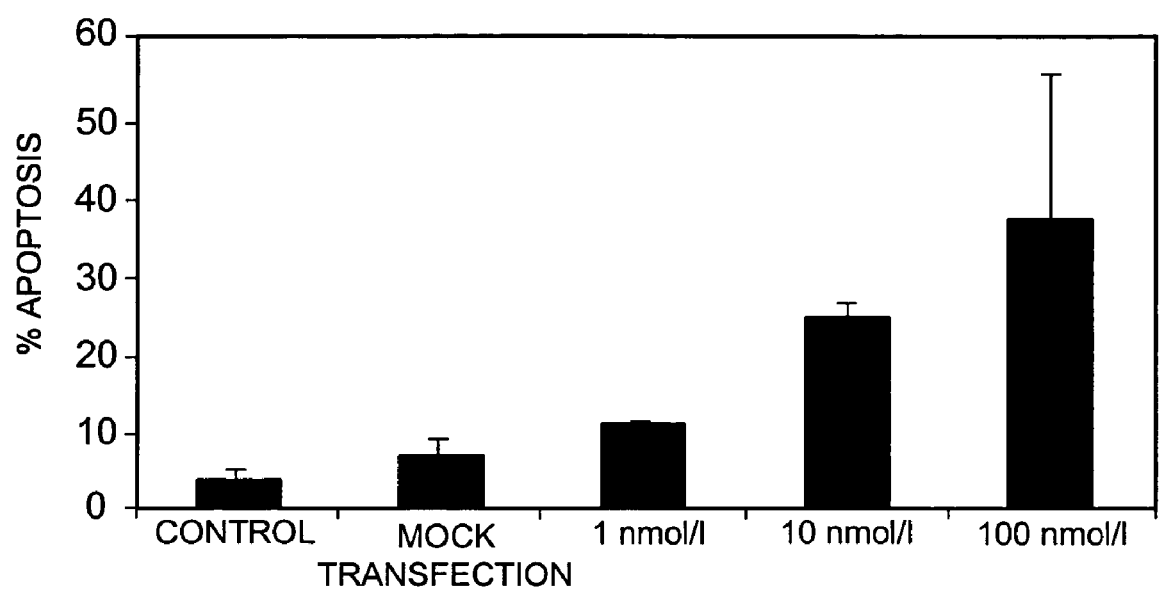
FIG. 1 shows the apoptosis rate (percent) of human pancreatic YAP C cancer cells, 120 hours after transfection with dsRNA 1 that is complementary to a first sequence of the human Bcl-2 gene.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by the expression of an anti-apoptotic gene using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the antisense strand) having a region which is less than 30 nucleotides in length and is substantially complementary to at least part of an mRNA transcript of an anti-apoptotic target gene, such as Bcl-2, Bcl-XL, Bcl-w, Mcl-1, and/or A1. The use of these dsRNAs enables the targeted degradation of mRNAs of genes that are implicated in uncontrolled cell or tissue growth. Using cell-based assays, the present inventors have demonstrated that very low dosages of these dsRNA can specifically and efficiently mediate RNAi, resulting in significant inhibition of expression of the target gene(s). Not only are lower dosages of dsRNA required as compared to traditional antisense RNA, but dsRNA affects apoptosis to such an extent that there is a noticeable reduction in both tumor size and number of tumor cells. Thus, the present invention encompasses these dsRNAs and compositions comprising dsRNA and their use for specifically silencing genes whose protein products either inhibit or prevent apoptosis in tumor cells. Moreover, the dsRNAs of the invention have no apparent effect on neighboring normal cells. Thus, the methods and compositions of the present invention comprising these dsRNAs are useful for treating cellular proliferative and/or differentiation disorders, such as cancer.

The following detailed description discloses how to make and use the dsRNA and compositions containing dsRNA to inhibit the expression of target anti-apoptotic genes, as well as compositions and methods for treating diseases and disorders caused by the expression of these genes. The pharmaceutical compositions of the present invention comprise a dsRNA having an antisense strand comprising a region of complementarity which is less than 30 nucleotides in length and is substantially complementary to at least part of an RNA transcript of an anti-apoptotic target gene, together with a pharmaceutically acceptable carrier. The anti-apoptotic gene may be a member of the Bcl-2 family, such as Bcl-2, Bcl-XL, Bcl-w, Mcl-1, and/or A1. The pharmaceutical composition may comprise a combination of dsRNAs having regions complementary to a plurality of anti-apoptotic genes, for example a combination of Bcl-2, Bcl-XL, Bcl-w, Mcl-1 and/or A1. Since many types of tumor cells are known to express multiple anti-apoptotic genes, compositions comprising a combination of dsRNAs are particularly effective at inhibiting the development and/or growth of tumor cells.

Accordingly, certain aspects of the present invention relate to pharmaceutical compositions comprising the dsRNA of the present invention together with a pharmaceutically acceptable carrier, methods of using the compositions to inhibit expression of a target anti-apoptotic gene, and methods of using the pharmaceutical compositions to treat diseases caused by expression of at least one of these anti-apoptotic genes.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the present invention by a nucleotide containing, for example, inosine. Sequences comprising such replacement moieties are embodiments of the present invention.

As used herein, "target gene" refers to a section of a DNA strand of a double-stranded DNA that is complementary to a section of a DNA strand, including all transcribed regions, that serves as a matrix for transcription. A target gene is a gene whose expression is to be selectively inhibited or silenced through RNA interference. As used herein, the term "target gene" specifically encompasses any cellular gene or gene fragment whose expression or activity is associated with the inhibition or prevention of apoptosis. For example, the target gene may be a gene from the Bcl-2 gene family, such as Bcl-2, Bcl-XL, Bcl-w, Mcl-1, and/or A1.

As used herein, "target sequence" refers to a contiguous portion of the nucleotide sequence of an mRNA molecule formed during the transcription of a target gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the present invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding bcl-2). For example, a polynucleotide is complementary to at least a part of a bcl-2 mRNA if the sequence is substantially complementary to a non-interrupted portion of a mRNA encoding bcl-2.

The term "double-stranded RNA" or "dsRNA", as used herein, refers to a ribonucleic acid molecule, or complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to a target gene, herein refer to the at least partial suppression of the expression of the target gene, as manifested by a reduction of the amount of mRNA transcribed from the target gene which may be isolated from a first cell or group of cells in which the target gene is transcribed and which has or have been treated such that the expression of the target gene is inhibited, as compared to a second cell or group of cells substantially identical to the first cell or group of cells but which has or have not been so treated (control cells). The degree of inhibition is usually expressed in terms of $$\frac{(\text{mRNA in control cells}) - (\text{mRNA in treated cells})}{(\text{mRNA in control cells})} \cdot 100\%$$

Alternatively, the degree of inhibition may be given in terms of a reduction of a parameter that is functionally linked to target gene transcription, e.g. the amount of protein encoded by the target gene which is secreted by a cell, or the number of cells displaying a certain phenotype, e.g apoptosis. In principle, target gene silencing may be determined in any cell expressing the target, either constitutively or by genomic engineering, and by any appropriate assay. However, when a reference is needed in order to determine whether a given siRNA inhibits the expression of the target gene by a certain degree and therefore is encompassed by the instant invention, the KB-GFP-BCL2 and assay of Example 1 herein below shall serve as such reference.

For example, in certain instances, expression of the target gene is suppressed by at least about 20%, 25%, 35%, or 50% by administration of the double-stranded oligonucleotide of the invention. In a preferred embodiment, the target gene is suppressed by at least about 60%, 70%, or 80% by administration of the double-stranded oligonucleotide of the invention. In a more preferred embodiment, the target gene is suppressed by at least about 85%, 90%, or 95% by administration of the double-stranded oligonucleotide of the invention. In a most preferred embodiment, the target gene is suppressed by at least about 98%, 99% or more by administration of the double-stranded oligonucleotide of the invention.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. A "patient" may be a human, but can also be a non-human animal.

As used herein, the phrases "therapeutically effective amount" and "prophylactically effective amount" refer to an amount that provides a therapeutic benefit in the treatment, prevention, or management of a disease or condition, e.g. cancer. The specific amount that is therapeutically effective can be readily determined by ordinary medical practitioner, and may vary depending on factors known in the art, such as, e.g. the type of cancer, the patient's history and age, the stage of cancer, the administration of other anti-cancer agents, including radiation therapy.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-stranded Ribonucleic Acid (dsRNA)

In one embodiment, the invention relates to a double-stranded ribonucleic acid (dsRNA) for inhibiting the expression of a target gene in a cell, wherein the dsRNA comprises an antisense strand comprising a region of complementarity which is complementary to at least a part of an mRNA formed in the expression of the target gene, and wherein the region of complementarity is less than 30 nucleotides in length and wherein said dsRNA, upon contact with a cell expressing said target gene, inhibits the expression of said target gene by at least 20%. The dsRNA comprises two RNA strands that are sufficiently complementary to hybridize to form a duplex structure. One strand of the dsRNA (the antisense strand) comprises a region of complementarity that is substantially complementary, and preferably fully complementary, to a target sequence, derived from the sequence of an mRNA formed during the expression of the target gene, the other strand (the sense strand) comprises a region which is complementary to the antisense strand, such that the two strands hybridize and form a duplex structure when combined under suitable conditions. Preferably, the duplex structure is between 15 and 30, more preferably between 18 and 25, yet more preferably between 19 and 24, and most preferably between 21 and 23 base pairs in length. Similarly, the region of complementarity to the target sequence is between 15 and 30, more preferably between 18 and 25, yet more preferably between 19 and 24, and most preferably between 21 and 23 nucleotides in length. The dsRNA of the present invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the target gene is a member of the Bcl-2 family, e.g., Bcl-2, Bcl-XL, Bcl-w, Mcl-1 or A1. In a particularly preferred embodiment, the target gene is Bcl-2. In specific embodiments, the antisense strand of the dsRNA comprises the sequence set forth in SEQ ID NO:2 and the sense strand comprises the sequence set forth in SEQ ID NO:1; or the antisense strand of the dsRNA comprises the sequence set forth in SEQ ID NO:4 and the sense strand comprises the sequence set forth in SEQ ID NO:3.

In further embodiments, the dsRNA comprises at least one nucleotide sequence selected from the groups of SEQ ID NOs: 7-296, 7-210, 7-170, 7-130, 7-68, 7-32, or 7-12. In other embodiments, the dsRNA comprises at least two sequences selected from these groups, wherein one of the at least two sequences is complementary to another of the at least two sequences, and one of the at least two sequences is substantially complementary to a sequence of an mRNA generated in the expression of a bcl-2 gene. Preferably, the dsRNA comprises two oligonucleotides, wherein one oligonucleotide is described by SEQ ID NO: (n) and the second oligonucleotide is described SEQ ID NO: (n+1), n being an odd number in the range of 7-295, for example in the range of 7-209, 7-169, 7-129, 7-67, 7-31, or 7-11.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences SEQ ID NOs: 7-296, the dsRNAs of the present invention comprise at least one strand of a length of minimally 21 nt. It can be reasonably expected that shorter dsRNAs comprising one of the sequences of SEQ ID NOs: 7-296 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of SEQ ID NOs: 7-296, and differing in their ability to inhibit the expression of a bcl-2 gene in a FACS assay as described herein below by not more than 5, 10, 15, 20, 25, or 30% inhibition from a dsRNA comprising the full sequence, are contemplated by the present invention.

The dsRNA of the present invention can contain one or more mismatches to the target sequence. In a preferred embodiment, the dsRNA of the present invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of a bcl-2 gene, the dsRNA preferably does not contain any mismatch within the central 13 nucleotides. The methods described within the present invention can be used to determine whether a dsRNA containing a mismatch to a target sequence is effective in inhibiting the expression of the target gene. Consideration of the efficacy of dsRNAs with mismatches in inhibiting expression of the target gene is important, especially if the particular region of complementarity in the target gene is known to have polymorphic sequence variation within the population.

In one embodiment, at least one end of the dsRNA has a single-stranded nucleotide overhang of 1 to 4, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Such dsRNAs have improved stability and inhibitory activity, thus allowing administration at low dosages, i.e., less than 5 mg/kg body weight of the recipient per day. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the present invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1,3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540.

Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the present invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the present invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the present invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

The present inventors have identified certain sequence motifs that are particularly prone to degradative attack by endonucleases, see co-pending and co-owned U.S. 60/574,744 and PCT/US2005/018931, both of which are hereby incorporated by reference in their entirety. Consequently, the protecting groups are preferably introduced within these sites of preferential degradation. For example, in certain embodiments, all the pyrimidines of an iRNA agent carry a 2'-protecting group, and the iRNA agent therefore has enhanced resistance to endonucleases. Enhanced nuclease resistance can also be achieved by protecting the 5' nucleotide, resulting, for example, in at least one 5'-uridine-adenine-3' (5'-UA-3') dinucleotide wherein the uridine is a 2'-protected nucleotide; at least one 5'-uridine-guanine-3' (5'-UG-3') dinucleotide, wherein the 5'-uridine is a 2'-protected nucleotide; at least one 5'-cytidine-adenine-3' (5'-CA-3') dinucleotide, wherein the 5'-cytidine is a 2'-protected nucleotide; at least one 5'-uridine-uridine-3' (5'-UU-3') dinucleotide, wherein the 5'-uridine is a 2'-protected nucleotide; or at least one 5'-cytidine-cytidine-3' (5'-CC-3') dinucleotide, wherein the 5'-cytidine is a 2'-protected nucleotide. The iRNA agent can include at least 2, at least 3, at least 4 or at least 5 of such protected dinucleotides. Most preferably, the 5'-most pyrimidines in all occurrences of the sequence motifs 5'-UA-3', 5'-CA-3', 5'-UU-3', and 5'-UG-3' are 2'-protected nucleotides. Alternatively, all pyrimidines of the sense strand of an iRNA agent carry a 2'-protecting group, and all occurrences of the sequence motifs 5'-UA-3', 5'-CA-3', 5'-UU-3', and 5'-UG-3' in the antisense strand are 2'-protected nucleotides.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis, 3rd International Symposium,* 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the present invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the present invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the present invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,808,027; all of which are hereby incorporated by reference.

In certain embodiments, the oligonucleotides employed in the ligand-conjugated oligonucleotides of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula $(O-alkyl)_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (J. Org. Chem. 1991, 56:4329); and Delgardo et. al. (Critical Reviews in Therapeutic Drug Carrier Systems 1992, 9:249), each of which is hereby incorporated by reference in its entirety. Further sugar modifications are disclosed by Cook (Anti-Cancer Drug Design, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-$NR_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (J. Org. Chem., 1997, 62:3415-3420). 2'-NR nucleosides are disclosed by Goettingen, M., J. Org. Chem., 1996, 61, 6273-6281; and Polushin et al., Tetrahedron Lett., 1996, 37, 3227-3230. Further representative 2'-substituent groups amenable to the present invention include those having one of formula I or II:

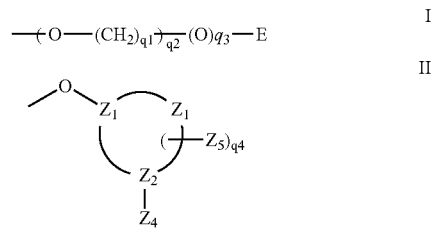

wherein,

E is $C_1$-$C_{10}$ alkyl, $N(Q_3)(Q_4)$ or $N=C$ $(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;
$q_2$ is an integer from 1 to 10;
$q_3$ is 0 or 1;
$q_4$ is 0, 1 or 2;

each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, $C(=NH)N(H)M_2$, $C(=O)N(H)M_2$ or $OC(=O)N(H)M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, $CH_2$, CHF, and $CF_2$. See, e.g., Secrist et al., Abstract 21, Program & Abstracts, Tenth International Roundtable, Nucleosides, Nucleotides and their Biological Applications, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300;

5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of an anti-apoptotic gene.

In another embodiment, the invention relates to a pharmaceutical composition comprising at least two dsRNAs, designed to target different anti-apoptotic genes, and a pharmaceutically acceptable carrier. The anti-apoptotic genes may be members of the Bcl-2 family, such as Bcl-2, Bcl-XL, Bcl-w, Mcl-1, and/or A1. Due of the targeting of mRNA of multiple anti-apoptotic genes, pharmaceutical compositions comprising a plurality of dsRNAs may provide improved efficiency of treatment as compared to compositions comprising a single dsRNA, at least in tumor cells expressing these multiple genes. In this embodiment, the individual dsRNAs are prepared as described in the preceding section, which is incorporated by reference herein. One dsRNA can have a nucleotide sequence which is substantially complementary to at least part of one anti-apoptotic gene; additional dsRNAs are prepared, each of which has a nucleotide sequence that is substantially complementary to part of a different anti-apoptotic gene. For example, one dsRNA may have a nucleotide sequence that is substantially complementary to a Bcl-2 gene, another dsRNA may have a nucleotide sequence that is substantially complementary to a Bcl-xL gene, and yet another dsRNA may have a nucleotide sequence that is substantially complementary to a Bcl-w gene. The multiple dsRNAs may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to target genes from the Bcl-2 family, the present invention encompasses any gene or combination of genes that have an inhibitory or preventive effect on apoptosis.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov ), as well as the NCI-MMHCC mouse repository. Examples of the genetic tools that are currently available for the modeling of leukemia and lymphomas in mice, and which are useful in practicing the present invention, are described in the following references: Maru, Y., *Int. J. Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A. W., et al, *J. Exp. Med.* (1988) 167(2):353-71; Zeng XX et al., *Blood*. (1988) 92(10):3529-36; Eriksson, B., et al., *Exp. Hematol.* (1999) 27(4):682-8; and Kovalchuk, A., et al., *J. Exp. Med.* (2000) 192(8):1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Diseases Caused by Expression of an Anti-apoptotic Gene.

In one embodiment, the invention relates to a method for treating a subject having a disease or at risk of developing a disease caused by the expression of an anti-apoptotic target gene. In this embodiment, the dsRNA can act as novel therapeutic agents for controlling one or more of cellular proliferative and/or differentiative disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA comprising a sequence substantially complementary to all or part of an mRNA formed in the transcription of a mutated gene associated with cancer, or one expressed at high levels in tumor cells, e.g. aurora kinase, may be brought into contact with or introduced into a cancerous cell or tumor.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of pancreas, prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The present invention also contemplates the simultaneous inhibition of expression of other genes. Preferably, other genes are selected which act additively or synergistically with the inhibition of the anti-apoptotic target gene described above in enhancing the overall action, for example, in suppressing growth of a cancer cell, or in treating, preventing or managing cancer. Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20): R776-8; Krepela, E., *Neoplasma* (2001) 48(5):332-49; Basbaum and Werb, *Curr. Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3):211-31; Fotedar, R., et al., *Prog. Cell Cycle Res.* (1996) 2:147-63; Reed, J. C., *Am. J. Pathol.* (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In one embodiment, a pharmaceutical compositions comprising dsRNA is used to inhibit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995)1:578-582) and mutation of DNA topoisomerase II (Beck, W. T., *J. Natl. Cancer Inst.* (1989) 81:1683-1685 ) also may render MDR.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of an Anti-apoptotic Gene

In yet another aspect, the invention relates to a method for inhibiting the expression of an anti-apoptotic gene in an organism. The method comprises administering a composition of the invention to the organism such that expression of the target anti-apoptotic gene is silenced. The organism may be an animal or a plant. Because of their high specificity, the dsRNAs of the present invention specifically target RNAs (primary or processed) of target anti-apoptotic genes, and at surprisingly low dosages. Compositions and methods for inhibiting the expression of these target genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the target anti-apoptotic gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibiting the expression of a target gene can be applied to any gene or group of genes that have a direct or indirect inhibitory affect on apoptosis. Examples of human genes which can be targeted for silencing according to the methods of the present invention include, without limitation, an oncogene; a gene that expresses molecules that induce angiogenesis; genes of proteins that are involved in metastasizing and/or invasive processes; and genes of proteases as well as of molecules that regulate apoptosis and the cell cycle. In a preferred embodiment, the tumor disease to be treated is a pancreatic carcinoma. There is no known treatment for pancreatic cancer, which currently has a survival rate of approximately 3%, the lowest of all carcinomas.

The methods for inhibition the expression of a target gene can also be applied to any plant anti-apoptotic gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

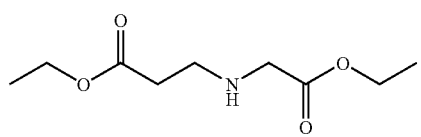

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-ylmethoxycarbonyl-amino)-hexanoyl]-amino}-propionic acid ethyl ester AB

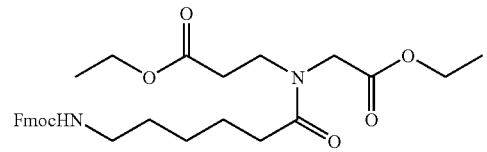

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

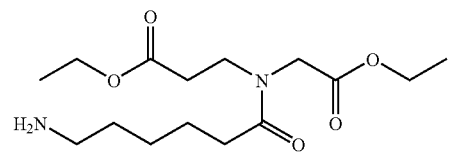

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

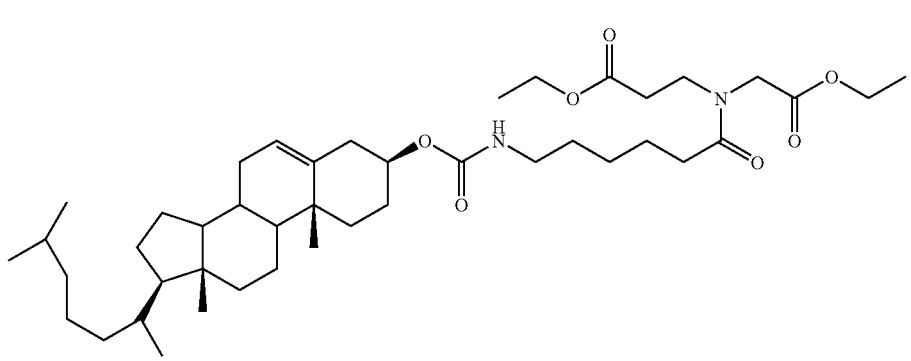

The hydrochloride salt of 3-[(6-Amino-hexanoyl)-ethoxy-carbonylmethyl-amino]-propionic acid ethyl ester AC (4.7 g, 14.8 mmol) was taken up in dichloromethane. The suspension was cooled to 0° C. on ice. To the suspension diisopropyl-ethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

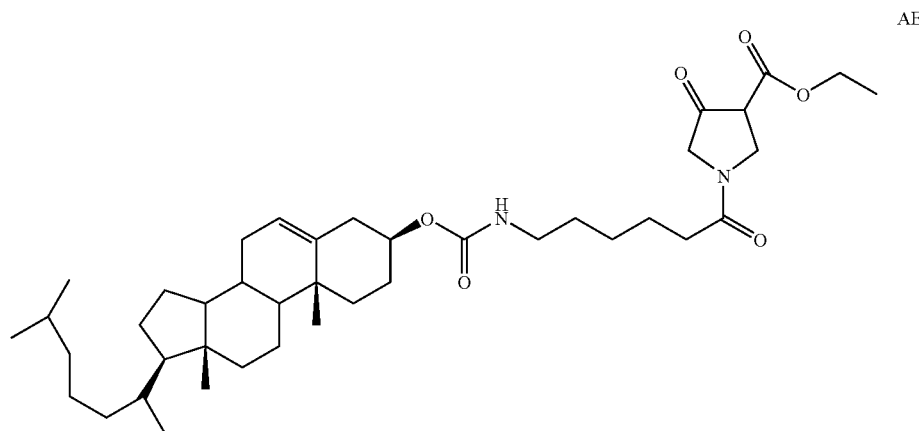

AE

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C.

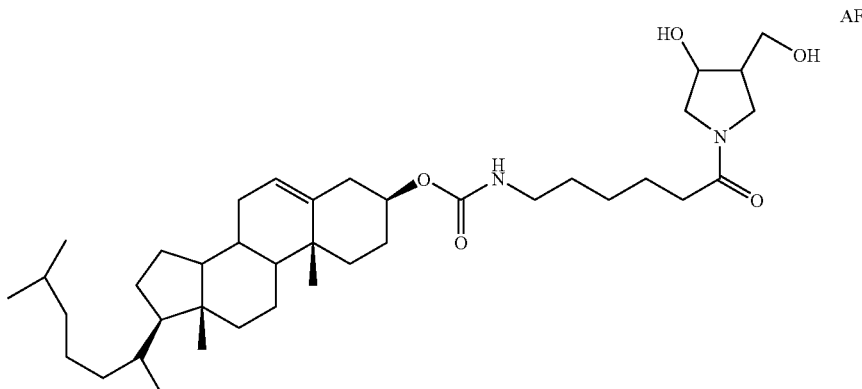

AF and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h.

After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

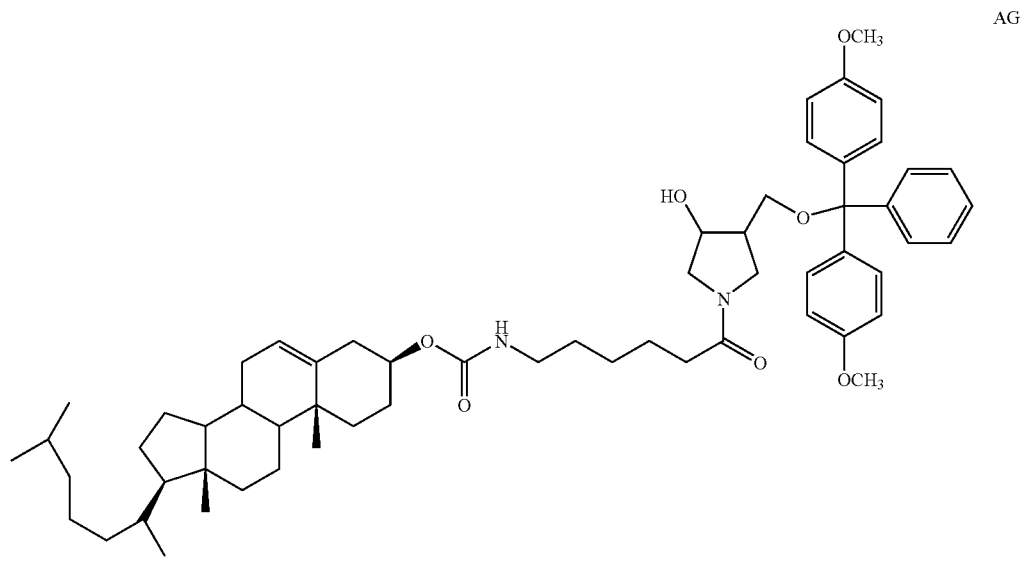

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual

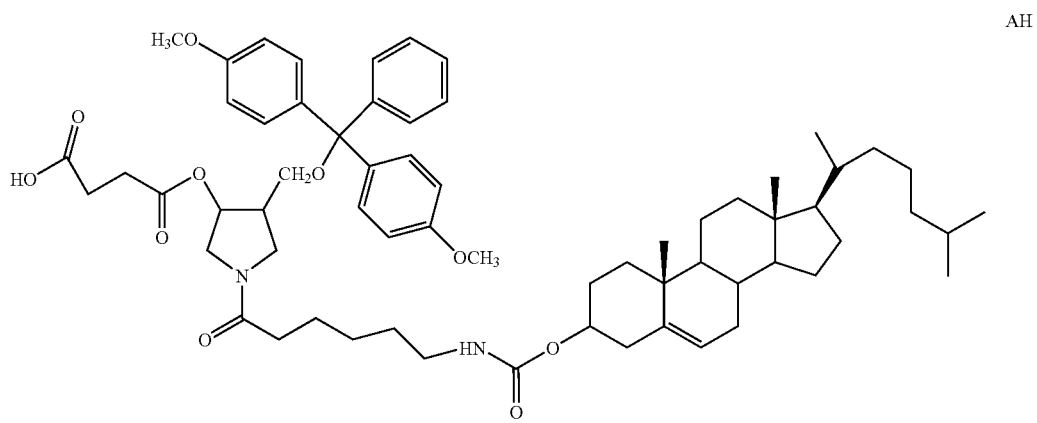

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

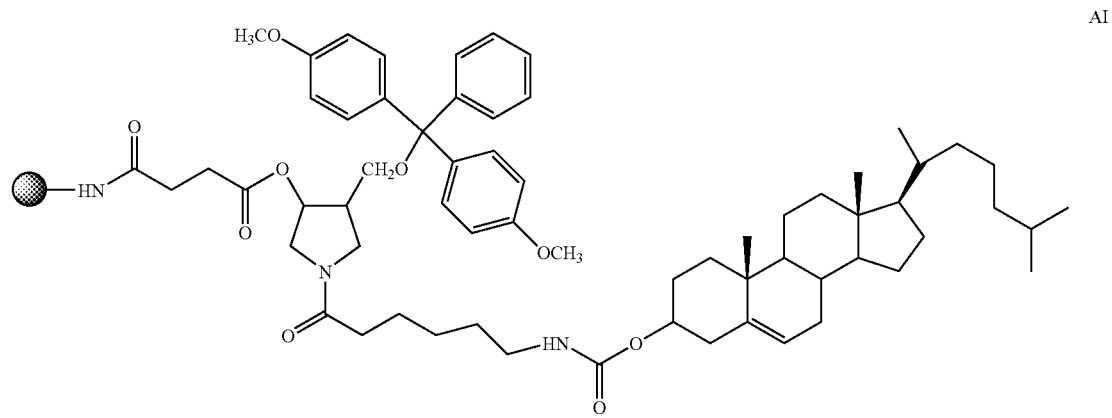

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
| --- | --- |
| A, a | 2'-deoxy-adenosine-5'-phosphate, adenosine-5'-phosphate |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
| --- | --- |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| am | 2'-O-methyladenosine-5'-phosphate |
| cm | 2'-O-methylcytidine-5'-phosphate |
| gm | 2'-O-methylguanosine-5'-phosphate |
| tm | 2'-O-methyl-thymidine-5'-phosphate |
| um | 2'-O-methyluridine-5'-phosphate |
| af | 2'-fluoro-2'-deoxy-adenosine-5'-phosphate |
| cf | 2'-fluoro-2'-deoxy-cytidine-5'-phosphate |
| gf | 2'-fluoro-2'-deoxy-guanosine-5'-phosphate |
| tf | 2'-fluoro-2'-deoxy-thymidine-5'-phosphate |
| uf | 2'-fluoro-2'-deoxy-uridine-5'-phosphate |
| <u>A</u>, <u>C</u>, <u>G</u>, <u>T</u>, <u>U</u>, <u>a</u>, <u>c</u>, <u>g</u>, <u>t</u>, <u>u</u> | underlined: nucleoside-5'-phosphorothioate |
| <u>am</u>, <u>cm</u>, <u>gm</u>, <u>tm</u>, <u>um</u> | underlined: 2-O-methyl-nucleoside-5'-phosphorothioate |

[a]capital letters represent 2'-deoxyribonucleotides (DNA), lower case letters represent ribonucleotides (RNA)

Example 1

Walking of Bcl-2

Selection of Sequences for siRNA Synthesis

Sequential BLAST searches (using the following parameters: Word size 7, Expect value 1000, mismatch penatlty −1)

were performed to identify sequences of 23 nucleotides within the sequence of human bcl-2 alpha (GenBank accession number M13994) or bcl-2 beta (GenBank accession number M13995) with 3 or more mismatches to any other human mRNA or genomic sequence. The 21 nucleotide sequence from position 3 to 23 of the 23mers were used for the synthesis of the sense strands of approximately 220 siRNAs. The corresponding antisense strands were synthesized to comprise a nucleotide sequence fully complementary to the 23mer search query, resulting in a 2-nucleotide single stranded overhang on the 3' end of the antisense strand of the siRNA. The sequences of all siRNAs thus selected and synthesized are shown in Table 1, SEQ ID 7 to 444.

The 23 nucleotide sequences thus selected were further compared by BLAST searching to identify those sequences identically found in mouse bcl-2 mRNA, but with 3 or more mismatched to any other mouse mRNA; the search parameters given above were again used. An siRNA capable of selectively inhibiting the expression of bcl-2 both in mice and humans could have certain advantages in clinical testing.

A dsRNA referred to herein as "K4," consisting of single strands with the sequences of SEQ ID 445 and 446, none of which is complementary to a sequence of a human mRNA, was synthesized to serve as a null reference of inhibition. The nucleotide sequence of the sense strand of K4 corresponds to nucleotide positions 2608-2630 in the sequence of vector pEGFP-C1 (GenBank Accession No. U55763).

Creation of Cell Line KB-GFP-BCL2

A reporter cell line for estimating the efficacy of siRNAs in inhibiting the expression of BCL2 is constructed by transfecting KB cells (ATCC order number CCL-17) with a reporter construct from which an mRNA is transcribed encoding an eGFP-BCL2 fusion protein. The efficacy of inhibition may be measured in such cells by comparing the fluorescence intensity of eGFP in such cells after treatment with an siRNA comprising a BCL2 sequence with the fluorescence intensity in such cells treated with a control siRNA.

The open reading frame of human BCL-2 (alpha splice form, GenBank accession number M13994) is PCR-amplified from a human BD™ Marathon-Ready cDNA library (BD Biosciences Clontech, Palo Alto, Calif., USA, Cat. #: 639343) using the BD Advantage HF 2 PCR kit (BD Biosciences Clontech, Palo Alto, Calif., USA Cat. #: 639123). Primer, nucleotide and enzyme concentration are used according to manufacturer's instructions. Amplification is performed in 30 cycles with the following three steps in each cycle: 20 sec. 95° C., 30 sec. 62° C., 60 sec. 72° C. A final step of 120 sec at 72° C. terminates the amplification reaction. Primers are AAA *CTC GAG* GCG CAC GCT GGG AGA ACG GGG (SEO ID NO:490) (introducing a XhoI (italics) restriction site upstream of the codon coding for amino acid 2 of BCL2) and AAA *TCT AGA* <u>TCA</u> CTT GTG GCT CAG ATA GGC (SEQ ID NO:491) (introducing a XbaI restriction site (italics) after the BCL2 stop codon (double underlined)). The PCR product is gel-purified on a 0.8% agarose gel, digested with XhoI and XbaI and ligated into pEGFP-C3 (BD Biosciences Clontech, Palo Alto Calif., USA; Cat. #: 632315) digested with XhoI and XbaI. The correct insertion of the cDNA is verified by sequencing. The plasmid is transfected into KB cells (ATCC order no. CCL17) by lipofection with Lipofectamin 2000 and Neomycin-resistant and fluorescing clones are identified in three rounds of: selection in the presence of G418 for 48 h followed by selection of fluorescent cells and replating of single cells using FACS-analysis.

Introduction of siRNAs into KB-GFP-BCL2-Cells and Determination of Gene Expression Inhibition by FACS Analysis KB-GFP-BCL2-Cells (about 80% confluent) were trypsinized from 96 mm Petri dishes with 5 ml trypsin-EDTA (0.25% Trypsin; 1 mM $Na_4$-EDTA; Gibco/Invitrogen, Karlsruhe, Germany) for 3-5 min at 37° C. The trypsin solution was gently removed, 5 ml cell culture medium (RPMI 1640 supplemented with 10% FCS, both Biochrom AG Berlin, Germany) were added and cells were centrifuged at 400 g for 5 minutes at room temperature. The cell pellet was resuspended in 250 µl cell culture medium and the cell number per unit volume determined in a Neubauer chamber. The resuspended cells were diluted to a density of 4 millions of cells per ml cell culture medium and 500 µl of this suspension were added to a 0.4 cm cuvette (Gene Pulser Cuvette, Bio-Rad Laboratories, Inc., Hercules, USA). 5 µl of a 20 µM stock solution of the respective siRNA in annealing buffer (100 mM NaCl, 10 mM $Na_2HPO_4$, 10 mM $NaH_2PO_4$, pH 6.8) was added to the cell suspension, for a total concentration of the siRNA in the incubation mixture of 200 nM, and gentle mixing was achieved by repeated aspiration/expulsion of the suspension using a 1 ml pipette (100-1000, Eppendorf AG, Hamburg, Germany). Electroporation was performed at 250V and 2500 µF with an exponential pulse in a Gene Pulser X cell with CE module (Bio-Rad Laboratories, Inc., Hercules, Calif., USA). 200 µl of the suspension were seeded in one well of a 6-well-plate, 2 ml cell culture medium per well were added and the plates were incubated at 37° C. and 5% $CO_2$ for 48 h (Heracell incubator, Kendro Laboratory products GmbH, Langenselbold, Germany).

Cells were harvested by removing the cell culture medium, adding 500 µl trypsin-EDTA (Gibco-Invitrogen GmbH, Karlsruhe, Germany) per well and incubating for 3-5 min at 37° C. After removing the trypsin solution and resuspending cells in 500 µl cell culture medium, the suspension was transferred to FACS tubes (5 ml, Sarstedt AG & Co., Nümbrecht, Germany) and centrifuged at 400 g for 5 min. Pellets were resuspended in 1 ml PBS (Biochrom, Cambridge, UK) and eGFP-fluorescence was measured by flow-cytometry (XL-MCL, Beckman Coulter GmbH, Krefeld, Germany) 10,000 cells were counted per tube and the percentage of eGFP-positive cells was multiplied with the mean fluorescence intensity of all measured cells to yield an overall fluorescence intensity per 10,000 cells ($FI_{10000}$).

Inhibition of expression of the eGFP-BCL2 fusion protein by the various siRNA species is summarized in Table 2. Therein, the efficacy in inhibiting the expression of eGFP-BCL2 is expressed as the amount by which $FI_{10000}$ is reduced by incubation of KB-GFP-BCL2-cells with individual siRNAs compared to incubation with the unrelated reference siRNA K4, as given by the following equation $$\text{Efficacy} = \left(1 - \frac{FI_{10000}(\text{siRNA})}{FI_{10000}(\text{K4})}\right) \times 100\%$$

Triplicate determinations were performed for each siRNA species to obtain average values and standard deviations.

The average transfection efficiency of the above method was estimated separately by transfecting unmodified KB cells (ATCC order number CCL-17) with plasmid pEGFP-C1, using 1 µg plasmid in 2 µl TE buffer (100 mM Tris-HCl, pH 7.3, 10 mM EDTA, pH 8.0) in place of the siRNA stock solution in the above procedure. Average transfection efficiency was estimated as 80±5%.

TABLE 2

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B31 | 31 | s: 5'-ccgggagauagugaugaagua-3'<br>as: 3'-uuggcccucuaucacuacuucau-5' | human | 84 ± 1 | SEQ ID NO:7<br>SEQ ID NO:8 |
| B529 | 529 | s: 5'-gacugaguaccugaaccggca-3'<br>as: 3'-uacugacucauggacuuggccgu-5' | human + mouse | 81 ± 0 | SEQ ID NO:9<br>SEQ ID NO:10 |
| B25 | 25 | s: 5'-cgauaaccgggagauagugau-3'<br>as: 3'-augcuauuggcccucuaucacua-5' | human | 80 ± 1 | SEQ ID NO:11<br>SEQ ID NO:12 |
| B21 | 21 | s: 5'-gguacgauaaccgggagauag-3'<br>as: 3'-ccccaugcuauuggcccucuauc-5' | human | 79 ± 2 | SEQ ID NO:13<br>SEQ ID NO:14 |
| B22 | 22 | s: 5'-guacgauaaccgggagauagu-3'<br>as: 3'-cccaugcuauuggcccucuauca-5' | human | 79 ± 1 | SEQ ID NO:15<br>SEQ ID NO:16 |
| B522 | 522 | s: 5'-uguggaugacugaguaccuga-3'<br>as: 3'-ggacaccuacugacucauggacu-5' | human | 79 ± 3 | SEQ ID NO:17<br>SEQ ID NO:18 |
| B463 | 463 | s: 5'-ggucaugugugggagagcgu-3'<br>as: 3'-ccccaguacacaccucucgca-5' | human | 78 ± 0 | SEQ ID NO:19<br>SEQ ID NO:20 |
| B523 | 523 | s: 5'-guggaugacugaguaccugaa-3'<br>as: 3'-gacaccuacugacucauggacuu-5' | human + mouse | 75 ± 2 | SEQ ID NO:21<br>SEQ ID NO:22 |
| B519 | 519 | s: 5'-cccuguggaugacugaguacc-3'<br>as: 3'-gcgggacaccuacugacucaugg-5' | human + mouse | 73 ± 0 | SEQ ID NO:23<br>SEQ ID NO:24 |
| B522 | 522 | s: 5'-uguggaugacugaguaccuga-3'<br>as: 3'-ggacaccuacugacucauggacu-5' | human | 71 ± 3 | SEQ ID NO:25<br>SEQ ID NO:26 |
| B133 | 133 | s: 5'-accgggcaucuucuccuccca-3'<br>as: 3'-cguggcccguagaagaggaggu-5' | human | 70 ± 1 | SEQ ID NO:27<br>SEQ ID NO:28 |
| B442 | 442 | s: 5'-ggccuucuuugaguucggugg-3'<br>as: 3'-caccggaagaaacucaagccacc-5' | human + mouse | 70 ± 5 | SEQ ID NO:29<br>SEQ ID NO:30 |
| B531 | 531 | s: 5'-cugaguaccugaaccggcacc-3'<br>as: 3'-cugacucauggacuuggccgugg-5' | human | 70 ± 3 | SEQ ID NO:31<br>SEQ ID NO:32 |
| B440 | 440 | s: 5'-guggccuucuuugaguucggu-3'<br>as: 3'-aacaccggaagaaacucaagcca-5' | human + mouse | 69 ± 1 | SEQ ID NO:33<br>SEQ ID NO:34 |
| B54 | 54 | s: 5'-uccauuauaagcugucgcaga-3'<br>as: 3'-guagguaauauucgacagcgucu-5' | human | 69 ± 1 | SEQ ID NO:35<br>SEQ ID NO:36 |
| B461 | 461 | s: 5'-ggggucaugugugggagagc-3'<br>as: 3'-caccccaguacacaccucucg-5' | human | 69 ± 1 | SEQ ID NO:37<br>SEQ ID NO:38 |
| B525 | 525 | s: 5'-ggaugacugaguaccugaacc-3'<br>as: 3'-caccuacugacucauggacuugg-5' | human + mouse | 68 ± 8 | SEQ ID NO:39<br>SEQ ID NO:40 |
| B535 | 535 | s: 5'-guaccugaaccggcaccugca-3'<br>as: 3'-cucauggacuuggccguggacgu-5' | human | 68 ± 8 | SEQ ID NO:41<br>SEQ ID NO:42 |
| B508 | 508 | s: 5'-ggacaacaucgcccugugau-3'<br>as: 3'-caccuguuguagcgggacaccua-5' | human + mouse | 67 ± 2 | SEQ ID NO:43<br>SEQ ID NO:44 |
| B56 | 56 | s: 5'-cauuauaagcugucgcagagg-3'<br>as: 3'-agguaauauucgacagcgucucc-5' | human | 67 ± 1 | SEQ ID NO:45<br>SEQ ID NO:46 |

TABLE 2-continued

List of siRNAs employed in the identification of siRNAs capable of efficiently inhibiting the expression of bcl2 in mammalian cells. Columns refer to: the denomination given to the siRNA, the number of the nucleotide within the human bcl-2 mRNA sequence, counting from its 5'-end, which marks the start of the 23mer sequence which the antisense strand of the siRNA is complementary to, the sequences of the sense (s) and the antisense (as) strand of the siRNA, the specificity for human bcl-2, human and mouse bcl-2 or the human splice variant bcl-2α, the efficacy of gene expression inhibition of human bcl-2 as determined by the FACS assay described hereinabove, given as % inhibition, ± standard deviation, in comparison to cells transfected with the null control siRNA denominated K4 and derived from the mRNA of the neomycin resistance gene, and the SEQ. ID of the strand sequences

| Name | 5'-Start nucleotide | Sequence | Specificity | Efficacy | Seq. ID |
|---|---|---|---|---|---|
| B462 | 462 | s: 5'-gggucaugugugugggagagcg-3'<br>as: 3'-accccaguacacacaccucucgc-5' | human + mouse | 66 ± 3 | SEQ ID NO:47<br>SEQ ID NO:48 |
| B33 | 33 | s: 5'-gggagauagugaugaaguaca-3'<br>as: 3'-ggcccucuaucacuacuucaugu-5' | human | 66 ± 6 | SEQ ID NO:49<br>SEQ ID NO:50 |
| B466 | 466 | s: 5'-caugugugugggagagcgucaa-3'<br>as: 3'-caguacacacaccucucgcaguu-5' | human + mouse | 64 ± 1 | SEQ ID NO:51<br>SEQ ID NO:52 |
| B459 | 459 | s: 5'-guggggucaugugugugggaga-3'<br>as: 3'-gccaccccaguacacacaccucu-5' | human | 63 ± 5 | SEQ ID NO:53<br>SEQ ID NO:54 |
| B45 | 45 | s: 5'-ugaaguacauccauuauaagc-3'<br>as: 3'-cuacuucauguagguaauauucg-5' | human | 63 ± 3 | SEQ ID NO:55<br>SEQ ID NO:56 |
| B520 | 520 | s: 5'-ccuguggaugacugaguaccu-3'<br>as: 3'-cgggacaccuacugacucaugga-5' | human + mouse | 62 ± 2 | SEQ ID NO:57<br>SEQ ID NO:58 |
| B465 | 465 | s: 5'-ucaugugugugggagagcguca-3'<br>as: 3'-ccaguacacacaccucucggagu-5' | human + mouse | 61 ± 7 | SEQ ID NO:59<br>SEQ ID NO:60 |
| B517 | 517 | s: 5'-cgcccuguggaugacugagua-3'<br>as: 3'-uagcgggacaccuacugacucau-5' | human + mouse | 61 ± 3 | SEQ ID NO:61<br>SEQ ID NO:62 |
| B524 | 524 | s: 5'-uggaugacugaguaccugaac-3'<br>as: 3'-acaccuacugacucauggacuug-5' | human + mouse | 61 ± 2 | SEQ ID NO:63<br>SEQ ID NO:64 |
| B555 | 555 | s: 5'-acaccuggauccaggauaacg-3'<br>as: 3'-cguguggaccuaggccuauugc-5' | human + mouse | 60 ± 4 | SEQ ID NO:65<br>SEQ ID NO:66 |
| B583 | 583 | s: 5'-ggaugccuuugugaacugua-3'<br>as: 3'-acccuacggaaacaccuugacau-5' | human | 60 ± 5 | SEQ ID NO:67<br>SEQ ID NO:68 |
| B464 | 464 | s: 5'-gucaugugugugggagagcguc-3'<br>as: 3'-cccaguacacacaccucucgcag-5' | human + mouse | 59 ± 4 | SEQ ID NO:69<br>SEQ ID NO:70 |
| B619 | 619 | s: 5'-gccucuguuugauuucuccug-3'<br>as: 3'-gccggagacaaacuaaagaggac-5' | human α | 59 ± 4 | SEQ ID NO:71<br>SEQ ID NO:72 |
| B617 | 617 | s: 5'-cggccucuguuugauuucucc-3'<br>as: 3'-acgccggagacaaacuaaagagg-5' | human α | 59 ± 1 | SEQ ID NO:73<br>SEQ ID NO:74 |
| B77 | 77 | s: 5'-ggcuacgagugggaugcggga-3'<br>as: 3'-ccccgaugcucacccuacgcccu-5' | human | 59 ± 6 | SEQ ID NO:75<br>SEQ ID NO:76 |
| B19 | 19 | s: 5'-aggguacgauaaccgggagau-3'<br>as: 3'-ugucccaugcuauuggcccucua-5' | human | 58 ± 3 | SEQ ID NO:77<br>SEQ ID NO:78 |
| B18 | 18 | s: 5'-cagggtacgauaaccgggaga-3'<br>as: 3'-uugucccaugcuauuggcccucu-5' | human | 57 ± 8 | SEQ ID NO:79<br>SEQ ID NO:80 |
| B457 | 457 | s: 5'-cgguggggucaugugugugga-3'<br>as: 3'-aagccaccccaguacacacaccu-5' | human + mouse | 57 ± 3 | SEQ ID NO:81<br>SEQ ID NO:82 |
| B24 | 24 | s: 5'-acgauaaccgggagauaguga-3'<br>as: 3'-caugcuauuggcccucuaucacu-5' | human | 56 ± 1 | SEQ ID NO:83<br>SEQ ID NO:84 |
| B411 | 411 | s: 5'-uggccuucuuugaguucggug-3'<br>as: 3'-acaccggaagaaacucaagccac-5' | human + mouse | 56 ± 4 | SEQ ID NO:85<br>SEQ ID NO:86 |

TABLE 2-continued

List of siRNAs employed in the identification of siRNAs capable of efficiently inhibiting the expression of bcl2 in mammalian cells. Columns refer to: the denomination given to the siRNA, the number of the nucleotide within the human bcl-2 mRNA sequence, counting from its 5'-end, which marks the start of the 23mer sequence which the antisense strand of the siRNA is complementary to, the sequences of the sense (s) and the antisense (as) strand of the siRNA, the specificity for human bcl-2, human and mouse bcl-2 or the human splice variant bcl-2α, the efficacy of gene expression inhibition of human bcl-2 as determined by the FACS assay described hereinabove, given as % inhibition, ± standard deviation, in comparison to cells transfected with the null control siRNA denominated K4 and derived from the mRNA of the neomycin resistance gene, and the SEQ. ID of the strand sequences

| Name | 5'-Start nucleotide | Sequence | Specificity | Efficacy | Seq. ID |
|---|---|---|---|---|---|
| B32 | 32 | s: 5'-cgggagauagugaugaaguac-3'<br>as: 3'-uggcccucuaucacuacuucaug-5' | human | 56 ± 4 | SEQ ID NO:87<br>SEQ ID NO:88 |
| B47 | 47 | s: 5'-aaguacauccauuauaagcug-3'<br>as: 3'-acuucauguagguaauauucgac-5' | human | 56 ± 1 | SEQ ID NO:89<br>SEQ ID NO:90 |
| B52 | 52 | s: 5'-cauccauuauaagcugucgca-3'<br>as: 3'-auguagguaauauucgacagcgu-5' | human | 56 ± 3 | SEQ ID NO:91<br>SEQ ID NO:92 |
| B439 | 439 | s: 5'-uguggccuucuuugaguucgg-3'<br>as: 3'-uaacaccggaagaaacucaagcc-5' | human + mouse | 55 ± 7 | SEQ ID NO:93<br>SEQ ID NO:94 |
| B79 | 79 | s: 5'-cuacgaguggggaugcgggaga-3'<br>as: 3'-ccgaugcucacccuacgcccucu-5' | human | 55 ± 9 | SEQ ID NO:95<br>SEQ ID NO:96 |
| B44 | 44 | s: 5'-augaaguacauccauuauaag-3'<br>as: 3'-acuacuucauguagguaauauuc-5' | human | 55 ± 5 | SEQ ID NO:97<br>SEQ ID NO:98 |
| B443 | 443 | s: 5'-gccuucuuugaguucgguggg-3'<br>as: 3'-accggaagaaacucaagccaccc-5' | human + mouse | 54 ± 4 | SEQ ID NO:99<br>SEQ ID NO:100 |
| B467 | 467 | s: 5'-auguguggagagcgucaac-3'<br>as: 3'-aguacacacaccucucgcaguug-5' | human + mouse | 54 ± 3 | SEQ ID NO:101<br>SEQ ID NO:102 |
| B28 | 28 | s: 5'-uaaccgggagauagugaugaa-3'<br>as: 3'-cuauuggcccucuaucacuacuu-5' | human | 54 ± 3 | SEQ ID NO:103<br>SEQ ID NO:104 |
| B521 | 521 | s: 5'-cugugaugacugaguaccug-3'<br>as: 3'-gggacaccuacugacucauggac-5' | human | 54 ± 1 | SEQ ID NO:105<br>SEQ ID NO:106 |
| B302 | 302 | s: 5'-gacgacuucucccgccgcuac-3'<br>as: 3'-cgcugcugaagagggcggcgaug-5' | human | 54 ± 1 | SEQ ID NO:107<br>SEQ ID NO:108 |
| B444 | 444 | s: 5'-ccuucuuugaguucgguggg-3'<br>as: 3'-ccggaagaaacucaagccacccc-5' | human + mouse | 53 ± 2 | SEQ ID NO:109<br>SEQ ID NO:110 |
| B509 | 509 | s: 5'-gacaacaucgcccugugaugau-3'<br>as: 3'-accuguuagcgggacaccuac-5' | human + mouse | 53 ± 5 | SEQ ID NO:111<br>SEQ ID NO:112 |
| B468 | 468 | s: 5'-ugugugggagagcgucaacc-3'<br>as: 3'-guacacacaccucucgcaguugg-5' | human | 53 ± 1 | SEQ ID NO:113<br>SEQ ID NO:114 |
| B518 | 518 | s: 5'-gcccuguggaugacugaguac-3'<br>as: 3'-agcgggacaccuacugacucaug-5' | human + mouse | 52 ± 4 | SEQ ID NO:115<br>SEQ ID NO:116 |
| B55 | 55 | s: 5'-ccauuauaagcugucgcagag-3'<br>as: 3'-uagguaauauucgacagcgucuc-5' | human | 52 ± 3 | SEQ ID NO:117<br>SEQ ID NO:118 |
| B586 | 586 | s: 5'-ugccuuugugguaacuguacgg-3'<br>as: 3'-cuacggaaacaccuugacaugcc-5' | human | 52 ± 9 | SEQ ID NO:119<br>SEQ ID NO:120 |
| B445 | 445 | s: 5'-cuucuuugaguucggugggu-3'<br>as: 3'-cggaagaaacucaagccacccca-5' | human + mouSe | 51 ± 3 | SEQ ID NO:121<br>SEQ ID NO:122 |
| B526 | 526 | s: 5'-gaugacugaguaccugaaccg-3'<br>as: 3'-accuacugacucauggacuuggc-5' | human + mouse | 51 ± 1 | SEQ ID NO:123<br>SEQ ID NO:124 |
| B328 | 328 | s: 5'-cgacuucgccgagauguccag-3'<br>as: 3'-ccgcugaagcggcucuacagguc-5' | human | 51 ± 1 | SEQ ID NO:125<br>SEQ ID NO:126 |

TABLE 2-continued

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B327 | 327 | s: 5'-gcgacuucgccgagaugucca-3'<br>as: 3'-ggcgcugaagcggcucuacaggu-5' | human | 51 ± 4 | SEQ ID NO:127<br>SEQ ID NO:128 |
| B460 | 460 | s: 5'-uggggucaugugugugggagag-3'<br>as: 3'-ccaccccaguacacacaccucuc-5' | human | 51 ± 2 | SEQ ID NO:129<br>SEQ ID NO:130 |
| B302 | 302 | s: 5'-gacgacuucucccgccgcuac-3'<br>as: 3'-cgcugcugaagagggcggcgaug-5' | human | 49 ± 1 | SEQ ID NO:131<br>SEQ ID NO:132 |
| B30 | 30 | s: 5'-accgggagauagugaugaagu-3'<br>as: 3'-auuggcccucuaucacuacuuca-5' | human | 49 ± 1 | SEQ ID NO:133<br>SEQ ID NO:134 |
| B30 | 30 | s: 5'-accgggagauagugaugaagu-3'<br>as: 3'-auuggcccucuaucacuacuuca-5' | human | 49 ± 1 | SEQ ID NO:135<br>SEQ ID NO:136 |
| B5 | 5 | s: 5'-cacgcugggagaacggggua c-3'<br>as: 3'-gcgugcgacccucuugcccaug-5' | human | 48 ± 1 | SEQ ID NO:137<br>SEQ ID NO:138 |
| B76 | 76 | s: 5'-gggcuacgaguggga ugcggg-3'<br>as: 3'-uccccgaugcucacccuacgccc-5' | human | 48 ± 2 | SEQ ID NO:139<br>SEQ ID NO:140 |
| B514 | 514 | s: 5'-caucgcccuguggaugacuga-3'<br>as: 3'-uuguagcgggacaccuacugacu-5' | human + mouse | 46 ± 2 | SEQ ID NO:141<br>SEQ ID NO:142 |
| B510 | 510 | s: 5'-acaacaucgcccuguggauga-3'<br>as: 3'-ccuguuguagcgggacaccuacu-5' | human + mouse | 45 ± 1 | SEQ ID NO:143<br>SEQ ID NO:144 |
| B301 | 301 | s: 5'-cgacgacuucucccgccgcua-3'<br>as: 3'-ccgcugcugaagagggcggcgau-5' | human | 45 ± 2 | SEQ ID NO:145<br>SEQ ID NO:146 |
| B11 | 11 | s: 5'-gggagaacggggua cgacaac-3'<br>as: 3'-gacccucuugccccaugcuguug-5' | human | 45 ± 2 | SEQ ID NO:147<br>SEQ ID NO:148 |
| B472 | 472 | s: 5'-uguggagagcgucaaccggga-3'<br>as: 3'-acacaccucucgcaguuggcccu-5' | human | 45 ± 11 | SEQ ID NO:149<br>SEQ ID NO:150 |
| B475 | 475 | s: 5'-ggagagcgucaaccgggagau-3'<br>as: 3'-caccucucgcaguuggcccucua-5' | human | 44 ± 1 | SEQ ID NO:151<br>SEQ ID NO:152 |
| B469 | 469 | s: 5'-gugugguggagagcgucaaccg-3'<br>as: 3'-uacacacaccucucgcaguuggc-5' | human | 44 ± 2 | SEQ ID NO:153<br>SEQ ID NO:154 |
| B135 | 135 | s: 5'-cgggcaucuucuccucccagc-3'<br>as: 3'-uggcccguagaagaggagggucg-5' | human | 42 ± 4 | SEQ ID NO:155<br>SEQ ID NO:156 |
| B559 | 559 | s: 5'-cuggauccaggauaacggagg-3'<br>as: 3'-uggaccuaggccuauugccucc-5' | human + mouse | 42 ± 2 | SEQ ID NO:157<br>SEQ ID NO:158 |
| B46 | 46 | s: 5'-gaaguacauccauuauaagcu-3'<br>as: 3'-uacuucauguagguaauauucga-5' | human | 42 ± 2 | SEQ ID NO:159<br>SEQ ID NO:160 |
| B616 | 616 | s: 5'-gcggccucuguuugauuucuc-3'<br>as: 3'-uacgccggagacaaacuaaagag-5' | humanα | 42 ± 4 | SEQ ID NO:161<br>SEQ ID NO:162 |
| B332 | 332 | s: 5'-uucgccgagauguccagccag-3'<br>as: 3'-ugaagcggcucuacaggucgguc-5' | human | 42 ± 3 | SEQ ID NO:163<br>SEQ ID NO:164 |
| B53 | 53 | s: 5'-auccauuauaagcugucgcag-3'<br>as: 3'-uguagguaauauucgacagcguc-5' | human | 42 ± 1 | SEQ ID NO:165<br>SEQ ID NO:166 |

TABLE 2-continued

List of siRNAs employed in the identification of siRNAs capable of efficiently inhibiting the expression of bcl2 in mammalian cells. Columns refer to: the denomination given to the siRNA, the number of the nucleotide within the human bcl-2 mRNA sequence, counting from its 5'-end, which marks the start of the 23mer sequence which the antisense strand of the siRNA is complementary to, the sequences of the sense (s) and the antisense (as) strand of the siRNA, the specificity for human bcl-2, human and mouse bcl-2 or the human splice variant bcl-2α, the efficacy of gene expression inhibition of human bcl-2 as determined by the FACS assay described hereinabove, given as % inhibition, ± standard deviation, in comparison to cells transfected with the null control siRNA denominated K4 and derived from the mRNA of the neomycin resistance gene, and the SEQ. ID of the strand sequences

| Name | 5'-Start nucleotide | Sequence | Specificity | Efficacy | Seq. ID |
|---|---|---|---|---|---|
| B474 | 474 | s: 5'-uggagagcgucaaccgggaga-3'<br>as: 3'-acaccucucgcaguuggcccucu-5' | human | 40 ± 9 | SEQ ID NO:167<br>SEQ ID NO:168 |
| B654 | 654 | s: 5'-ggagagcgucaaccgggagau-3'<br>as: 3'-caccucucgcaguuggcccucua-5' | human | 40 ± 2 | SEQ ID NO:169<br>SEQ ID NO:170 |
| B470 | 470 | s: 5'-uguguggagagcgucaaccgg-3'<br>as: 3'-acacacaccucucgcaguuggcc-5' | human | 39 ± 3 | SEQ ID NO:171<br>SEQ ID NO:172 |
| B330 | 330 | s: 5'-acuucgccgagaugúccagcc-3'<br>as: 3'-gcugaagcggcucuacaggucgg-5' | human | 38 ± 3 | SEQ ID NO:173<br>SEQ ID NO:174 |
| B29 | 29 | s: 5'-aaccgggagauagugaugaag-3'<br>as: 3'-uauuggcccucuaucacuacuuc-5' | human | 38 ± 2 | SEQ ID NO:175<br>SEQ ID NO:176 |
| B668 | 668 | s: 5'-gcccuggugggagcuugcauc-3'<br>as: 3'-accgggaccacccucgaacguag-5' | human α | 37 ± 3 | SEQ ID NO:179<br>SEQ ID NO:180 |
| B668 | 668 | s: 5'-gcccuggugggagcuugcauc-3'<br>as: 3'-accgggaccacccucgaacguag-5' | human α | 37 ± 3 | SEQ ID NO:177<br>SEQ ID NO:178 |
| B507 | 507 | s: 5'-uggacaacaucgcccugugga-3'<br>as: 3'-ccaccuguuguagcgggacaccu-5' | human +<br>mouse | 36 ± 4 | SEQ ID NO:181<br>SEQ ID NO:182 |
| B511 | 511 | s: 5'-caacaucgcccuguggaugac-3'<br>as: 3'-cuguuguagcgggacaccuacug-5' | human +<br>mouse | 35 ± 1 | SEQ ID NO:183<br>SEQ ID NO:184 |
| B7 | 7 | s: 5'-cgcugggagaacgggguacga-3'<br>as: 3'-gugcgacccucuugccccaugcu-5' | human | 35 ± 5 | SEQ ID NO:185<br>SEQ ID NO:186 |
| B556 | 556 | s: 5'-caccuggauccaggauaacgg-3'<br>as: 3'-guguggaccuaggúccuauugcc-5' | human +<br>mouse | 35 ± 2 | SEQ ID NO:187<br>SEQ ID NO:188 |
| B516 | 516 | s: 5'-ucgcccuguggaugacugagu-3'<br>as: 3'-guagcgggacaccuacugacuca-5' | human +<br>mouse | 34 ± 2 | SEQ ID NO:189<br>SEQ ID NO:190 |
| B557 | 557 | s: 5'-accuggauccaggauaacgga-3'<br>as: 3'-uguggaccuagguccuauugccu-5' | human +<br>mouse | 34 ± 1 | SEQ ID NO:191<br>SEQ ID NO:192 |
| B321 | 321 | s: 5'-accgccgcgacuucgccgaga-3'<br>as: 3'-gauggcggcgcugaagcggcucu-5' | human | 34 ± 3 | SEQ ID NO:193<br>SEQ ID NO:194 |
| B447 | 447 | s: 5'-ucuuugaguucggugggguca-3'<br>as: 3'-gaagaaacucaagccaccccagu-5' | human +<br>mouse | 32 ± 3 | SEQ ID NO:195<br>SEQ ID NO:196 |
| B515 | 515 | s: 5'-aucgcccuguggaugacugag-3'<br>as: 3'-uguagcgggacaccuacugacuc-5' | human +<br>mouse | 32 ± 3 | SEQ ID NO:197<br>SEQ ID NO:198 |
| B558 | 558 | s: 5'-ccuggauccaggauaacggag-3'<br>as: 3'-guggaccuagguccuauugccuc-5' | human +<br>mouse | 32 ± 1 | SEQ ID NO:199<br>SEQ ID NO:200 |
| B446 | 446 | s: 5'-uucuuugaguucggugggguc-3'<br>as: 3'-ggaagaaacucaagccacccag-5' | human +<br>mouse | 31 ± 2 | SEQ ID NO:201<br>SEQ ID NO:202 |
| B527 | 527 | s: 5'-augacugaguaccugaaccgg-3'<br>as: 3'-ccuacugacucauggacuuggcc-5' | human +<br>mouse | 31 ± 2 | SEQ ID NO:203<br>SEQ ID NO:204 |
| B381 | 381 | s: 5'-gacgcuuugccacgguggugg-3'<br>as: 3'-cccugcgaaacggugccaccacc-5' | human +<br>mouse | 30 ± 3 | SEQ ID NO:205<br>SEQ ID NO:206 |

TABLE 2-continued

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B27 | 27 | s: 5'-auaaccgggagauagugauga-3'<br>as: 3'-gcuauuggcccucuaucacuacu-5' | human | 30 ± 4 | SEQ ID NO:207<br>SEQ ID NO:208 |
| B530 | 530 | s: 5'-acugaguaccugaaccggcac-3'<br>as: 3'-acugacugauggacuuggccgug-5' | human | 30 ± 7 | SEQ ID NO:209<br>SEQ ID NO:210 |
| B10 | 10 | s: 5'-ugggagaacaggguacgacaa-3'<br>as: 3'-cgacccucuuguccccaugcuguu-5' | human | 29 ± 1 | SEQ ID NO:211<br>SEQ ID NO:212 |
| B132 | 132 | s: 5'-caccgggcaucuucuccuccc-3'<br>as: 3'-gcguggcccguagaagaggaggg-5' | human | 29 ± 3 | SEQ ID NO:213<br>SEQ ID NO:214 |
| B380 | 380 | s: 5'-ggacgcuuugccacgguggug-3'<br>as: 3'-ccccugcgaaacggugccaccac-5' | human + mouse | 29 ± 3 | SEQ ID NO:215<br>SEQ ID NO:216 |
| B452 | 452 | s: 5'-gaguucgguggggucaugugu-3'<br>as: 3'-aacucaagccaccccaguacaca-5' | human + mouse | 29 ± 7 | SEQ ID NO:217<br>SEQ ID NO:218 |
| B383 | 383 | s: 5'-cgcuuuugccacggugguggag-3'<br>as: 3'-cugcgaaacggugccaccaccac-5' | human + mouse | 29 ± 0 | SEQ ID NO:219<br>SEQ ID NO:220 |
| B51 | 51 | s: 5'-acauccauuauaagcugucgc-3'<br>as: 3'-cauguagguaauauucgacagcg-5' | human | 29 ± 4 | SEQ ID NO:221<br>SEQ ID NO:222 |
| B82 | 82 | s: 5'-cgagugggaugcgggagaugu-3'<br>as: 3'-augcucacccuacgcccucuaca-5' | human | 29 ± 3 | SEQ ID NO:223<br>SEQ ID NO:224 |
| B380 | 380 | s: 5'-ggacgcuuugccacgguggug-3'<br>as: 3'-ccccugcgaaacggugccaccac-5' | human + mouse | 29 ± 3 | SEQ ID NO:225<br>SEQ ID NO:226 |
| B51 | 51 | s: 5'-acauccauuauaagcugucgc-3'<br>as: 3'-cauguagguaauauucgacagcg-5' | human | 29 ± 4 | SEQ ID NO:227<br>SEQ ID NO:228 |
| B513 | 513 | s: 5'-acaucgcccuguggaugacug-3'<br>as: 3'-guuguagcgggacaccuacugac-5' | human + mouse | 28 ± 1 | SEQ ID NO:229<br>SEQ ID NO:230 |
| B49 | 49 | s: 5'-guacauccauuauaagcuguc-3'<br>as: 3'-uucauguagguaauauucgacag-5' | human | 28 ± 5 | SEQ ID NO:231<br>SEQ ID NO:232 |
| B554 | 554 | s: 5'-cacaccuggauccaggauaac-3'<br>as: 3'-acguguggaccuagguccuauug-5' | human + mouse | 27 ± 3 | SEQ ID NO:233<br>SEQ ID NO:234 |
| B326 | 326 | s: 5'-cgcgacuucgccgagaugucc-3'<br>as: 3'-cggcgcugaagcggcucuacagg-5' | human | 27 ± 4 | sEQ ID NO:235<br>SEQ ID NO:236 |
| B528 | 528 | s: 5'-ugacugaguaccugaaccggc-3'<br>as: 3'-cuacugacucauggacuuggccg-5' | human + mouse | 26 ± 2 | SEQ ID NO:237<br>SEQ ID NO:238 |
| B560 | 560 | s: 5'-uggauccaggauaacggaggc-3'<br>as: 3'-ggaccuagguccuauugccuccg-5' | human + mouse | 26 ± 5 | SEQ ID NO:239<br>SEQ ID NO:240 |
| B78 | 78 | s: 5'-gcuacgagugggaugcgggag-3'<br>as: 3'-cccgaugcucacccuacgcccuc-5' | human | 26 ± 4 | SEQ ID NO:241<br>SEQ ID NO:242 |
| B451 | 451 | s: 5'-ugaguucgguggggucaugug-3'<br>as: 3'-aaacucaagccaccccaguacac-5' | human + mouse | 25 ± 12 | SEQ ID NO:243<br>SEQ ID NO:244 |
| B454 | 454 | s: 5'-guucgguggggucaugugugu-3'<br>as: 3'-cucaagccaccccaguacacaca-5' | human + mouse | 25 ± 5 | SEQ ID NO:245<br>SEQ ID NO:246 |

TABLE 2-continued

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B569 | 569 | s: 5'-gauaacggaggcugggaugcc-3'<br>as: 3'-uccuauugccuccgacccuacgg-5' | human α + mouse | 25 ± 2 | SEQ ID NO:247<br>SEQ ID NO:248 |
| B670 | 670 | s: 5'-ccuggugggagcuugcaucac-3'<br>as: 3'-cgggaccacccucgaacguagug-5' | human α | 25 ± 4 | SEQ ID NO:249<br>SEQ ID NO:250 |
| B75 | 75 | s: 5'-ggggcuacgagugggaugcgg-3'<br>as: 3'-cuccccgaugcucacccuacgcc-5' | human | 25 ± 5 | SEQ ID NO:251<br>SEQ ID NO:252 |
| B23 | 23 | s: 5'-uacgacaaccgggagauagug-3'<br>as: 3'-ccaugcuguuggccucuaucac-5' | human | 24 ± 1 | SEQ ID NO:253<br>SEQ ID NO:254 |
| B295 | 295 | s: 5'-ggccggcgacgacuucucccg-3'<br>as: 3'-guccggccgcugcugaagaggggc-5' | human | 24 ± 7 | SEQ ID NO:255<br>SEQ ID NO:256 |
| B329 | 329 | s: 5'-gacuucgccgagauguccagc-3'<br>as: 3'-cgcugaagcggcucuacaggucg-5' | human | 24 ± 2 | SEQ ID NO:257<br>SEQ ID NO:258 |
| B505 | 505 | s: 5'-gguggacaacaucgcccugug-3'<br>as: 3'-gaccaccuguuguagcgggacac-5' | human + mouse | 24 ± 3 | SEQ ID NO:259<br>SEQ ID NO:260 |
| B81 | 81 | s: 5'-acgaguggggaugcgggagaug-3'<br>as: 3'-gaugcucacccuacgcccucuac-5' | human | 24 ± 2 | SEQ ID NO:261<br>SEQ ID NO:262 |
| B134 | 134 | s: 5'-ccgggcaucuucuccucccag-3'<br>as: 3'-guggcccguagaagaggagggguc-5' | human | 23 ± 6 | SEQ ID NO:263<br>SEQ ID NO:264 |
| B540 | 540 | s: 5'-ugaaccggcaccugcacaccu-3'<br>as: 3'-ggacuuggccguggacgugugga-5' | human | 23 ± 2 | SEQ ID NO:265<br>SEQ ID NO:266 |
| B458 | 458 | s: 5'-gguggggucaugugugugggag-3'<br>as: 3'-agccaccccaguacacacaccuc-5' | human | 23 ± 6 | SEQ ID NO:267<br>SEQ ID NO:268 |
| B448 | 448 | s: 5'-cuuugaguucggguggggucau-3'<br>as: 3'-aagaaacucaagccaccccagua-5' | human + mouse | 22 ± 9 | SEQ ID NO:269<br>SEQ ID NO:270 |
| B671 | 671 | s: 5'-cugguggggagcuugcaucacc-3'<br>as: 3'-gggaccacccucgaacguagugg-5' | human α | 22 ± 3 | SEQ ID NO:271<br>SEQ ID NO:272 |
| B323 | 323 | s: 5'-cgccgcgacuucgccgagaug-3'<br>as: 3'-uggcggcgcugaagcggcucuac-5' | human | 22 ± 2 | SEQ ID NO:273<br>SEQ ID NO:274 |
| B4 | 4 | s: 5'-gcacgcugggagaacggggua-3'<br>as: 3'-cgcgugcgacccucuugcccau-5' | human | 21 ± 1 | SEQ ID NO:275<br>SEQ ID NO:276 |
| B453 | 453 | s: 5'-aguucggguggggucaugugug-3'<br>as: 3'-acucaagccaccccaguacacac-5' | human + mouse | 21 ± 11 | SEQ ID NO:277<br>SEQ ID NO:278 |
| B6 | 6 | s: 5'-acgcugggagaacggggguacg-3'<br>as: 3'-cgugcgacccucuugcccaugc-5' | human | 21 ± 4 | SEQ ID NO:279<br>SEQ ID NO:280 |
| B659 | 659 | 5: 5'-cucaguuuggcccuggugggga-3'<br>as: 3'-gcgagucaaaccgggaccacccu-5' | human α | 21 ± 4 | SEQ ID NO:281<br>SEQ ID NO:282 |
| B50 | 50 | s: 5'-uacauccauuauaagcugucg-3'<br>as: 3'-ucauguaggguaauauucgacagc-5' | human | 21 ± 0 | SEQ ID NO:283<br>SEQ ID NO:284 |
| B334 | 334 | s: 5'-cgccgagauguccagccagcu-3'<br>as: 3'-aagcggcucuacaggucggucga-5' | human | 21 ± 5 | SEQ ID NO:285<br>SEQ ID NO:286 |

TABLE 2-continued

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B659 | 659 | s: 5'-cucaguuuggcccuggugggga-3'<br>as: 3'-gcgagucaaaccgggaccacccu-5' | human α | 21 ± 4 | SEQ ID NO:287<br>SEQ ID NO:288 |
| B289 | 289 | s: 5'-ccgccaggccggcgacgacuu-3'<br>as: 3'-gaggcgguccggccgcugcugaa-5' | human | 20 ± 3 | SEQ ID NO:289<br>SEQ ID NO:290 |
| B384 | 384 | s: 5'-gcuuugccacggguggguggagg-3'<br>as: 3'-ugcgaaacgugccaccaccucc-5' | human + mouse | 20 ± 2 | SEQ ID NO:291<br>SEQ ID NO:292 |
| B48 | 48 | s: 5'-aguacauccauuauaagcugu-3'<br>as: 3'-cuucauguagguaauauucgaca-5' | human | 20 ± 3 | SEQ ID NO:293<br>SEQ ID NO:294 |
| B538 | 538 | s: 5'-ccugaaccggcaccugcacac-3'<br>as: 3'-auggacuuggccguggacgugug-5' | human | 20 ± 4 | SEQ ID NO:295<br>SEQ ID NO:296 |
| B324 | 324 | s: 5'-gccgcgacuucgccgagaugu-3'<br>as: 3'-ggcggcgcugaagcggcucuaca-5' | human | 19 ± 6 | SEQ ID NO:297<br>SEQ ID NO:298 |
| B12 | 12 | s: 5'-ggagaacggggguacgacaacc-3'<br>as: 3'-acccucuugccccaugcuguugg-5' | human | 19 ± 3 | SEQ ID NO:299<br>SEQ ID NO:300 |
| B13 | 13 | s: 5'-gagaacggggguacgacaaccg-3'<br>as: 3'-cccucuugccccaugcuguuggc-5' | Human | 18 ± 3 | SEQ ID NO:301<br>SEQ ID NO:302 |
| B352 | 352 | s: 5'-gcugcaccugacgccuucac-3'<br>as: 3'-gucgacguggacugcgggaagug-5' | human + mouSe | 18 ± 5 | SEQ ID NO:303<br>SEQ ID NO:304 |
| B676 | 676 | s: 5'-gggagcuugcaucacccuggg-3'<br>as: 3'-caccucgaacguagugggaccc-5' | human α | 18 ± 3 | SEQ ID NO:305<br>SEQ ID NO:306 |
| B325 | 325 | s: 5'-ccgcgacuucgccgagauguc-3'<br>as: 3'-gcggcgcugaagcggcucuacag-5' | human | 18 ± 1 | SEQ ID NO:307<br>SEQ ID NO:308 |
| B322 | 322 | s: 5'-ccgccgcgacuucgccgagau-3'<br>as: 3'-auggcggcgcugaagcggcucua-5' | human | 18 ± 2 | SEQ ID NO:309<br>SEQ ID NO:310 |
| B333 | 333 | s: 5'-ucgccgagauguccagccagc-3'<br>as: 3'-gaagcggcucuacaggucggucg-5' | human | 18 ± 5 | SEQ ID NO:311<br>SEQ ID NO:312 |
| B450 | 450 | s: 5'-uugaguucgguggggucaugu-3'<br>as: 3'-gaaacucaagccaccccaguaca-5' | human + mouse | 17 ± 1 | SEQ ID NO:313<br>SEQ ID NO:314 |
| B83 | 83 | s: 5'-gagugggaugcgggagaugug-3'<br>as: 3'-ugcucacccuacgcccucuacac-5' | human | 17 ± 3 | SEQ ID NO:315<br>SEQ ID NO:316 |
| B582 | 582 | s: 5'-gggaugccuuuguggaacugu-3'<br>as: 3'-gacccuacggaaacaccuugaca-5' | human | 17 ± 3 | SEQ ID NO:317<br>SEQ ID NO:318 |
| B658 | 658 | s: 5'-gcucaguuuggcccugguggg-3'<br>as: 3'-gacgagucaaaccgggaccaccc-5' | human α | 16 ± 5 | SEQ ID NO:319<br>SEQ ID NO:320 |
| B80 | 80 | s: 5'-uacgaguggaugcgggagau-3'<br>as: 3'-cgaugcucacccuacgcccucua-5' | human | 16 ± 4 | SEQ ID NO:321<br>SEQ ID NO:322 |
| B130 | 130 | s: 5'-cgcaccgggcaucuucuccuc-3'<br>as: 3'-gggcguggcccguagaagaggag-5' | human | 15 ± 2 | SEQ ID NO:323<br>SEQ ID NO:324 |
| B294 | 294 | s: 5'-aggccggcgacgacuucuccc-3'<br>as: 3'-gguccggccgcugcugaagaggg-5' | human | 15 ± 2 | SEQ ID NO:325<br>SEQ ID NO:326 |

TABLE 2-continued

List of siRNAs employed in the identification of siRNAs capable of
efficiently inhibiting the expression of bcl2 in mammalian cells.
Columns refer to: the denomination given to the siRNA, the number
of the nucleotide within the human bcl-2 mRNA sequence, counting
from its 5'-end, which marks the start of the 23mer sequence which
the antisense strand of the siRNA is complementary to, the sequences
of the sense (s) and the antisense (as) strand of the siRNA, the
specificity for human bcl-2, human and mouse bcl-2 or the human splice
variant bcl-2α, the efficacy of gene expression inhibition of human
bcl-2 as determined by the FACS assay described hereinabove, given as %
inhibition, ± standard deviation, in comparison to cells transfected
with the null control siRNA denominated K4 and derived from the mRNA
of the neomycin resistance gene, and the SEQ. ID of the strand sequences

| Name | 5'-Start nucleotide | Sequence | Specificity | Efficacy | Seq. ID |
|---|---|---|---|---|---|
| B686 | 686 | s: 5'-aucacccuggugccuaucug-3'<br>as: 3'-cguagugggacccacggauagac-5' | human α | 15 ± 3 | SEQ ID NO:327<br>SEQ ID NO:328 |
| B292 | 292 | s: 5'-ccaggccggcgacgacuucuc-3'<br>as: 3'-gcgguccggccgcugcugaagag-5' | human | 15 ± 4 | SEQ ID NO:329<br>SEQ ID NO:330 |
| B291 | 291 | s: 5'-gccaggccggcgacgacuucu-3'<br>as: 3'-ggcguccggccgcugcugaaga-5' | human | 15 ± 3 | SEQ ID NO:331<br>SEQ ID NO:332 |
| B356 | 356 | s: 5'-caccugacgcccuucaccgcg-3'<br>as: 3'-acguggacugcgggaaguggcgc-5' | human + mouse | 14 ± 4 | SEQ ID NO:333<br>SEQ ID NO:334 |
| B663 | 663 | s: 5'-guuuggcccuggugggagcuu-3'<br>as: 3'-gucaaaccgggaccacccucgaa-5' | human α | 14 ± 3 | SEQ ID NO:335<br>SEQ ID NO:336 |
| B586 | 586 | s: 5'-ugccuuugugaacuguacgg-3'<br>as: 3'-cuacggaaacaccuugacaugcc-5' | human | 14 ± 2 | SEQ ID NO:337<br>SEQ ID NO:338 |
| B353 | 353 | s: 5'-cugcaccugacgcccuucacc-3'<br>as: 3'-ucgacguggacugcgggaagugg-5' | human + mouse | 13 ± 1 | SEQ ID NO:339<br>SEQ ID NO:340 |
| B512 | 512 | s: 5'-aacaucgcccuguggaugacu-3'<br>as: 3'-uguuguagcgggacaccuacuga-5' | human + mouse | 13 ± 1 | SEQ ID NO:341<br>SEQ ID NO:342 |
| B657 | 657 | s: 5'-ugcucaguuuggcccuggugg-3'<br>as: 3'-agacgacucaaaccgggaccacc-5' | human α | 13 ± 1 | SEQ ID NO:343<br>SEQ ID NO:344 |
| B473 | 473 | s: 5'-guggagagcgucaaccggag-3'<br>as: 3'-cacaccucucgcaguuggcccuc-5' | human | 13 ± 4 | SEQ ID NO:345<br>SEQ ID NO:346 |
| B532 | 532 | s: 5'-ugaguaccugaaccggcaccu-3'<br>as: 3'-ugacucauggacuuggccgugga-5' | human | 13 ± 1 | SEQ ID NO:347<br>SEQ ID NO:348 |
| B504 | 504 | s: 5'-ugguggacaacaucgcccugu-3'<br>as: 3'-ggaccaccuguuguagcgggaca-5' | human + mouse | 12 ± 3 | SEQ ID NO:349<br>SEQ ID NO:350 |
| B382 | 382 | s: 5'-acgcuuugccacgguggugga-3'<br>as: 3'-ccugcgaaacggugccaccaccu-5' | human + mouse | 12 ± 2 | SEQ ID NO:351<br>SEQ ID NO:352 |
| B355 | 355 | s: 5'-gcaccugacgcccuucaccgc-3'<br>as: 3'-gacguggacugcgggaaguggcg-5' | human + mouse | 11 ± 4 | SEQ ID NO:353<br>SEQ ID NO:354 |
| B673 | 673 | s: 5'-ggugggagcuugcaucacccu-3'<br>as: 3'-gaccacccucgaacguagggga-5' | human α | 11 ± 1 | SEQ ID NO:355<br>SEQ ID NO:356 |
| B561 | 561 | s: 5'-ggauccaggauaacggaggcu-3'<br>as: 3'-gaccuagguccuauugccuccga-5' | human + mouse | 10 ± 2 | SEQ ID NO:357<br>SEQ ID NO:358 |
| B16 | 16 | s: 5'-aacaggguacgauaaccggga-3'<br>as: 3'-ucuugucccaugcuauuggcccu-5' | human | 9 ± 3 | SEQ ID NO:359<br>SEQ ID NO:360 |
| B568 | 568 | s: 5'-ggauaacggaggcugggaugc-3'<br>as: 3'-guccuauugccuccgacccuacg-5' | human α + mouse | 9 ± 1 | SEQ ID NO:361<br>SEQ ID NO:362 |
| B664 | 664 | s: 5'-uuuggcccuggugggagcuug-3'<br>as: 3'-ucaaaccgggaccacccucgaac-5' | human α | 9 ± 3 | SEQ ID NO:363<br>SEQ ID NO:364 |
| B15 | 15 | s: 5'-gaacaggguacgauaaccggg-3'<br>as: 3'-cucaagacccaugcuauuggccc-5' | human | 8 ± 2 | SEQ ID NO:365<br>SEQ ID NO:366 |

TABLE 2-continued

List of siRNAs employed in the identification of siRNAs capable of efficiently inhibiting the expression of bcl2 in mammalian cells. Columns refer to: the denomination given to the siRNA, the number of the nucleotide within the human bcl-2 mRNA sequence, counting from its 5'-end, which marks the start of the 23mer sequence which the antisense strand of the siRNA is complementary to, the sequences of the sense (s) and the antisense (as) strand of the siRNA, the specificity for human bcl-2, human and mouse bcl-2 or the human splice variant bcl-2α, the efficacy of gene expression inhibition of human bcl-2 as determined by the FACS assay described hereinabove, given as % inhibition, ± standard deviation, in comparison to cells transfected with the null control siRNA denominated K4 and derived from the mRNA of the neomycin resistance gene, and the SEQ. ID of the strand sequences

| Name | 5'-Start nucleotide | Sequence | Specificity | Efficacy | Seq. ID |
|---|---|---|---|---|---|
| B354 | 354 | s: 5'-ugcaccugacgcccuucaccg-3'<br>as: 3'-cgacguggacugcgggaaguggc-5' | human + mouse | 8 ± 3 | SEQ ID NO:367<br>SEQ ID NO:368 |
| B664 | 664 | s: 5'-uuuggcccuggugggagcuug-3'<br>as: 3'-ucaaaccgggaccacccucgaac-5' | human α | 8 ± 5 | SEQ ID NO:369<br>SEQ ID NO:370 |
| B17 | 17 | s: 5'-acagguacgauaaccgggag-3'<br>as: 3'-cuugucccaugcuauuggcccuc-5' | human | 7 ± 0 | SEQ ID NO:371<br>SEQ ID NO:372 |
| B293 | 293 | s: 5'-caggccggcgacgacuucucc-3'<br>as: 3'-cgguccggccgcugcugaagagg-5' | human | 7 ± 1 | SEQ ID NO:373<br>SEQ ID NO:374 |
| B296 | 296 | s: 5'-gccggcgacgacuucucccgc-3'<br>as: 3'-uucggccgcugcugaagagggcg-5' | human | 7 ± 3 | SEQ ID NO:375<br>SEQ ID NO:376 |
| B303 | 303 | s: 5'-acgacuucucccgccgcuacc-3'<br>as: 3'-gcugcugaagagggcggcgaugg-5' | human | 7 ± 2 | SEQ ID NO:377<br>SEQ ID NO:378 |
| B455 | 455 | s: 5'-uucgguggggucaugugugug-3'<br>as: 3'-ucaagccaccccaguacacacac-5' | human + mouse | 7 ± 2 | SEQ ID NO:379<br>SEQ ID NO:380 |
| B8 | 8 | s: 5'-gcugggagaacaggguacgac-3'<br>as: 3'-ugcgaccucuugucccaugcug-5' | human | 7 ± 3 | SEQ ID NO:381<br>SEQ ID NO:382 |
| B129 | 129 | s: 5'-ccgcaccgggcaucuucuccu-3'<br>as: 3'-ggggcguggcccguagaagagga-5' | human | 6 ± 3 | SEQ ID NO:383<br>SEQ ID NO:384 |
| B304 | 304 | s: 5'-cgacuucucccgccgcuaccg-3'<br>as: 3'-cugcugaagagggcggcgauggc-5' | human | 6 ± 2 | SEQ ID NO:389<br>SEQ ID NO:390 |
| B682 | 682 | s: 5'-uugcaucacccugggugccua-3'<br>as: 3'-cgaacguagugggacccacggau-5' | human α | 6 ± 4 | SEQ ID NO:385<br>SEQ ID NO:386 |
| B682 | 682 | s: 5'-uugcaucacccugggugccua-3'<br>as: 3'-cgaacguagugggacccacggau-5' | human α | 6 ± 4 | SEQ ID NO:387<br>SEQ ID NO:388 |
| B506 | 506 | s: 5'-guggacaacaucgcccugugg-3'<br>as: 3'-accaccuguuguagcgggacacc-5' | human + mouse | 5 ± 6 | SEQ ID NO:391<br>SEQ ID NO:392 |
| B138 | 138 | s: 5'-gcaucuucuccucccagcccg-3'<br>as: 3'-cccguagaagaggagggucgggc-5' | human | 4 ± 2 | SEQ ID NO:393<br>SEQ ID NO:394 |
| B385 | 385 | s: 5'-cuuugccacggugguggagga-3'<br>as: 3'-gcgaaacggugccaccaccuccu-5' | human + mouse | 4 ± 2 | SEQ ID NO:395<br>SEQ ID NO:396 |
| B131 | 131 | s: 5'-gcaccgggcaucuucuccucc-3'<br>as: 3'-ggcguggcccguagaagaggagg-5' | human | 3 ± 6 | SEQ ID NO:397<br>SEQ ID NO:398 |
| B600 | 600 | s: 5'-uguacggccccagcaugcggc-3'<br>as: 3'-ugacaugccggggucguacgccg-5' | human α | 3 ± 1 | SEQ ID NO:399<br>SEQ ID NO:400 |
| B653 | 653 | s: 5'-acucugcucaguuuggcccug-3'<br>as: 3'-ucugagacgagucaaaccgggac-5' | human α | 3 ± 4 | SEQ ID NO:401<br>SEQ ID NO:402 |
| B665 | 665 | s: 5'-uuggcccuggugggagcuugc-3'<br>as: 3'-caaaccgggaccacccucgaacg-5' | human α | 3 ± 10 | SEQ ID NO:403<br>SEQ ID NO:404 |
| B666 | 666 | s: 5'-uggcccuggugggagcuugca-3'<br>as: 3'-aaaccgggaccacccucgaacgu-5' | human α | 3 ± 3 | SEQ ID NO:405<br>SEQ ID NO:406 |

TABLE 2-continued

List of siRNAs employed in the identification of siRNAs capable of efficiently inhibiting the expression of bcl2 in mammalian cells. Columns refer to: the denomination given to the siRNA, the number of the nucleotide within the human bcl-2 mRNA sequence, counting from its 5'-end, which marks the start of the 23mer sequence which the antisense strand of the siRNA is complementary to, the sequences of the sense (s) and the antisense (as) strand of the siRNA, the specificity for human bcl-2, human and mouse bcl-2 or the human splice variant bcl-2α, the efficacy of gene expression inhibition of human bcl-2 as determined by the FACS assay described hereinabove, given as % inhibition, ± standard deviation, in comparison to cells transfected with the null control siRNA denominated K4 and derived from the mRNA of the neomycin resistance gene, and the SEQ. ID of the strand sequences

| Name | 5'-Start nucleotide | Sequence | Specificity | Efficacy | Seq. ID |
|---|---|---|---|---|---|
| B684 | 684 | s: 5'-gcaucacccuggguugccuauc-3'<br>as: 3'-aacguagugggacccacggauag-5' | human α | 3 ± 1 | SEQ ID NO:407<br>SEQ ID NO:408 |
| B672 | 672 | s: 5'-ugguggagcuugcaucaccc-3'<br>as: 3'-ggaccacccucgaacguagggg-5' | human α | 2 ± 2 | SEQ ID NO:409<br>SEQ ID NO:410 |
| B602 | 602 | s: 5'-uacggccccagcaugcggccu-3'<br>as: 3'-acaugccggggucgacgccgga-5' | human α | 2 ± 3 | SEQ ID NO:411<br>SEQ ID NO:412 |
| B581 | 581 | s: 5'-ugggaugccuuuguggaacug-3'<br>as: 3'-cgacccuacggaaacaccuugac-5' | human | 2 ± 6 | SEQ ID NO:413<br>SEQ ID NO:414 |
| B14 | 14 | s: 5'-agaacaggguacgauaaccgg-3'<br>as: 3'-ccucuugcccaugcuauuggcc-5' | human | 1 ± 3 | SEQ ID NO:415<br>SEQ ID NO:416 |
| B305 | 305 | s: 5'-gacuucucccgccgcuaccgc-3'<br>as: 3'-ugcugaagagggcggcgauggcg-5' | human | 1 ± 2 | SEQ ID NO:417<br>SEQ ID NO:418 |
| B651 | 651 | s: 5'-agacucugcucaguuuggccc-3'<br>as: 3'-cuucugagacgagucaaaccggg-5' | human α | 1 ± 4 | SEQ ID NO:419<br>SEQ ID NO:420 |
| B675 | 675 | s: 5'-ugggagcuugcaucacccugg-3'<br>as: 3'-ccacccucgaacguagugggacc-5' | human α | 0 ± 11 | SEQ ID NO:421<br>SEQ ID NO:422 |
| B674 | 674 | s: 5'-gugggagcuugcaucacccug-3'<br>as: 3'-accacccucgaacguaguggggac-5' | human α | 0 ± 1 | SEQ ID NO:423<br>SEQ ID NO:424 |
| B290 | 290 | s: 5'-cgccaggccggcgacgacuuc-3'<br>as: 3'-aggcggguccggccgcugcugaag-5' | human | 0 ± 2 | SEQ ID NO:425<br>SEQ ID NO:426 |
| B73 | 73 | s: 5'- gaggggcuacgaguggggaugc-3'<br>as: 3'-gucuccccgaugcucacccuacg-5' | human + mouse | -1 ± 1 | SEQ ID NO:427<br>SEQ ID NO:428 |
| B162 | 162 | s: 5'-acacgccccauccagccgcau-3'<br>as: 3'-cgugugcggggguaggucggcgua-5' | human | -5 ± 1 | SEQ ID NO:429<br>SEQ ID NO:430 |
| B679 | 679 | s: 5'-agcuugcaucacccuggguuc-3'<br>as: 3'-ccucgaacguaguggggacccacg-5' | human α | -6 ± 1 | SEQ ID NO:431<br>SEQ ID NO:432 |
| B71 | 71 | s: 5'-cagaggggcuacgagugggau-3'<br>as: 3'-gcgucuccccgaugcucaccccua-5' | human | -6 ± 5 | SEQ ID NO:433<br>SEQ ID NO:434 |
| B599 | 599 | s: 5'-cuguacggccccagcaugcgg-3'<br>as: 3'-uugacaugccggggucgacgcc-5' | human α | -7 ± 7 | SEQ ID NO:435<br>SEQ ID NO:436 |
| B681 | 681 | s: 5'-cuugcaucacccuggguugccu-3'<br>as: 3'-ucgaacguaguggggacccacgga-5' | human α | -7 ± 1 | sEQ ID NO:437<br>SEQ ID NO:438 |
| B683 | 683 | s: 5'-ugcaucacccuggguugccuau-3'<br>as: 3'-gaacguagugggacccacggaua-5' | human α | -10 ± 4 | SEQ ID NO:439<br>SEQ ID NO:440 |
| B691 | 691 | s: 5'-ccugggugccuaucuggggcca-3'<br>as: 3'-ugggacccacggauagacccggu-5' | human α | -10 ± 6 | SEQ ID NO:441<br>SEQ ID NO:442 |
| B58 | 58 | s: 5'-uuauaagcugucgcagagggg-3'<br>as: 3'-guaauauucgacagcgucuccccc-5' | human | -16 ± 5 | SEQ ID NO:443<br>SEQ ID NO:444 |
| K4 negative control | 2606 of U55763 | s: 5'-gaugaggaucguuucgcauga-3'<br>as: 3'-uccuacuccuagcaaagcguacu-5' | n.a. | 0 | SEQ ID NO:445<br>SEQ ID NO:446 |

Example 2

Optimization of siRNAs by Chemical Modification

As has been experienced by those working in the antisense field, ribonucleic acids are often quickly degraded by a range of nucleases present in virtually all biological environments, e.g. endonucleases, exonucleases etc. This vulnerability may be circumvented by chemically modifying these oligonucleotides such that nucleases may no longer attack. Consequentially, 8 siRNAs were chosen, designated B21, B22, B25, B133, B442, B519, B522, B523, and B529 in Table 2, which showed superior activity in the assay described in Example 1, for the testing of the effect of stabilizing modifications on the activity of siRNAs to inhibit gene expression.

To establish whether the chemical modification of nucleotides interferes with the ability of siRNAs to inhibit gene expression, we chose to start with a minimal modification. siRNAs corresponding to B21, B22, B25, B133, B442, B519, B522, B523, and B529, but comprising 2'-O-Methyl substituted nucleotides in positions 21 and 22 (counting 5' to 3') of the antisense strands were synthesized and their activity was tested in KB-GFP-BCL2 cells as described in Example 1 above (B529-2OMe, B25-2OMe, B21-2OMe, B22-2OMe, B522-2OMe, B523-2OMe, B519-2OMe, B133-2OMe, B442-2OMe).

TABLE 3

List of siRNAs employed in testing the influence of 2'-O-Methyl nucleotide modifications on siRNA efficacy (spaces inserted in sense-strand sequences to show alignment)

| Name | 5'-Start nucleotide | Sequence | Efficacy of unmodified [%] | Efficacy [%] | Seq ID |
|---|---|---|---|---|---|
| B529-2OMe | 529 | s: 5'-g acugaguaccugaaccggca-3'<br>as: 3'-uamcmugacucauggacuuggccgu-5' | 81 ± 0 | 78 ± 4 | (SEQ ID NO:447)<br>(SEQ ID NO:448) |
| B25-2OMe | 25 | s: 5'-c gauaaccgggagauagugau-3'<br>as: 3'-aumgmcuauuggcccucuaucacua-5' | 80 ± 1 | 74 ± 4 | (SEQ ID NO:449)<br>(SEQ ID NO:450) |
| B21-2OMe | 21 | s: 5'-g guacgauaaccgggagauag-3'<br>as: 3'-ccmcmaugcuauuggcccucuauc-5' | 79 ± 2 | 82 ± 0 | (SEQ ID NO:451)<br>(SEQ ID NO:452) |
| B22-2OMe | 22 | s: 5'-g uacgauaaccgggagauagu-3'<br>as: 3'-ccmcmaugcuauuggcccucuauca-5' | 79 ± 1 | 83 ± 2 | (SEQ ID NO:453)<br>(SEQ ID NO:454) |
| B522-2OMe | 522 | s: 5'-u guggaugacugaguaccuga-3'<br>as: 3'-ggmamcaccuacugacucauggacu-5' | 79 ± 3 | 73 ± 3 | (SEQ ID NO:455)<br>(SEQ ID NO:456) |
| B523-2OMe | 523 | s: 5'-g uggaugacugaguaccugaa-3'<br>as: 3'-gamcmaccuacugacucauggacuu-5 | 75 ± 2 | 80 ± 2 | (SEQ ID NO:457)<br>(SEQ ID NO:458) |
| B519-2OMe | 519 | s: 5'-cccuguggaugacugaguacc-3'<br>as: 3'-gcmgmggacaccuacugacucaugg-5' | 73 ± 0 | 65 ± 3 | (SEQ ID NO:459)<br>(SEQ ID NO:460) |
| B133-2OMe | 133 | s: 5'-a ccgggcaucuucuccuccca-3'<br>as: 3'-cgmumggcccguagaagaggagggu-5' | 70 ± 1 | 66 ± 10 | (SEQ ID NO:461)<br>(SEQ ID NO:462) |
| B442-2OMe | 442 | s: 5'-g gccuucuuugaguucggugg-3'<br>as: 3'-camcmcggaagaaacucaagccacc-5' | 70 ± 5 | 72 ± 0 | (SEQ ID NO:463)<br>(SEQ ID NO:464) |

When comparing the efficacy of inhibition of the unmodified siRNAs (4th column in Table 3) to those of the siRNAs comprising the 2 2'-O-Methyl modifications (5th column in Table 3), it is evident that the modifications had only a minor effect on efficacy, often within error limits of the assay.

Another modification often employed in attempting to modify the properties of oligonucleotides, e.g. increase plasma binding, is the introduction of phosphorothioate linkages into the backbone of the oligonucleotide. To test the efficacy of phosphorothioate-modified siRNAs, we synthesized siRNAs wherein the phosphodiester linkages between positions 21 and 22, and 22 and 23, respectively, (counting 5' to 3') of the antisense strands of B529, B25, B519, and B442 were replaced by phosphorothioate linkages (B529-2PO, B25-2PO, B519-2PO, B442-2PO). In addition, one siRNA was synthesized wherein the phosphodiester linkages between positions 1 and 2, 2 and 3, 3 and 4, 4 and 5, 19 and 20, 20 and 21, 21 and 22, and 22 and 23 of the antisense strand, and 1 and 2, 2 and 3, 3 and 4, 4 and 5, 17 and 18, 18 and 19, 19 and 20, and 20 and 21 of the sense strand, respectively, (counting 5' to 3') of B442 were replaced by phosphorothioate linkages (B442-16PO).

TABLE 4

List of siRNAs employed in testing the influence of 2'-O-Methyl nucleotide modifications on siRNA efficacy

| Name | 5'-Start nucleotide | Sequence | Efficacy of unmodified [%] | Efficacy [%] | Seq. ID |
|---|---|---|---|---|---|
| B529-2PO | 529 | s: 5'-gacugaguaccugaaccggca-3'<br>as: 3'-uacugacucauggacuuggccgu-5' | 81 ± 0 | 79 ± 2 | SEQ ID NO:465<br>SEQ ID NO:466 |
| B25-2PO | 25 | s: 5'-cgauaaccgggagauagugau-3'<br>as: 3'-augcuauuggcccucuaucacua-5' | 80 ± 1 | 75 ± 2 | SEQ ID NO:467<br>SEQ ID NO:468 |
| B519-2PO | 519 | s: 5'-cccuguggaugacugaguacc-3'<br>as: 3'-gcgggacaccacugacucaugg-5' | 73 ± 0 | 70 ± 2 | SEQ ID NO:469<br>SEQ ID NO:470 |
| B442-2PO | 442 | s: 5'-ggccuucuuugaguucggugg-3'<br>as: 3'-caccggaagaaacucaagccacc-5' | 70 ± 5 | 75 ± 3 | SEQ ID NO:471<br>SEQ ID NO:472 |
| B442-16PO | 442 | s: 5'-ggccuucuuugaguucggugg-3'<br>as: 3'-caccggaagaaacucaagccacc-5' | 70 ± 5 | 72 ± 4 | SEQ ID NO:473<br>SEQ ID NO:474 |

Again, the replacement of phosphodiester linkages by phosphorothioate linkages had no significant effect on the efficacy of these siRNAs.

Next, we examined the effect of lipophilic groups linked to the 3'- or 5'-end of the sense and/or antisense strand of siRNAs. Lipophilic groups tethered to an oligonucleotide have been held to increase the permeation of oligonucleotides through the membrane of cells even in the absence of agents that aid transfection. We tested a 12-dodecanoic acid bisdecylamide group linked to the 5'-end of the sense strand, the 5'-end of the antisense strand, and to the 5'end of both strands, of B442-2OMe (B442-5'C32s, B442-5'C32as, B442-5'C32b). Furthermore, we tested a cholesteryl derivative linked via a phosphorothioate linkage to the 3'-end of the sense strand of B442-2OMe, combined with additional replacement of the phosphodiester linkages between positions 21 and 22, and 22 and 23, respectively, (counting 5' to 3') of the antisense strand (B442-3'Chol).

TABLE 5

List of siRNAs employed in testing the influence of lipophilic groups linked to the 3'- or 5'- end of the sense and/or antisense strand on siRNA efficacy (spaces inserted in sense-strand sequences to show alignment)

| Name | 5'-Start nucleotide | Sequence | Efficacy of B442-2OMe [%] | Efficacy [%] | Seq. ID |
|---|---|---|---|---|---|
| B442-5'C32s | 442 | s: 5'-C32-g gccuucuuugaguucggugg-3'<br>as: 3'-camcmcggaagaaacucaagccacc-5' | 72 ± 0 | 57 ± 3 | SEQ ID NO:475<br>SEQ ID NO:476 |
| B442-5'C32as | 442 | s: 5'-g gccuucuuugaguucggugg-3'<br>as: 3'-camcmcggaagaaacucaagccacc-C32-5' | 72 ± 0 | 68 ± 3 | SEQ ID NO:477<br>SEQ ID NO:478 |

TABLE 5-continued

List of siRNAs employed in testing the influence of lipophilic groups linked
to the 3'- or 5'- end of the sense and/or antisense strand on siRNA efficacy
(spaces inserted in sense-strand sequences to show alignment)

| Name | 5'-Start nucleotide | Sequence | Efficacy of B442-2OMe [%] | Efficacy [%] | Seq. ID |
|---|---|---|---|---|---|
| B442-5'C32b | 442 | s: 5'-C32-g gccuucuuugaguucggugg-3'<br>as: 3'-camcmcggaagaaacucaagccacc-C32-5' | 72 ± 0 | -23 ± 5 | SEQ ID NO:479<br>SEQ ID NO:480 |
| B442-3'Chol | 442 | s: 5'-g gccuucuuugaguucggugg-Chol-3'<br>as: 3'-camcmcggaagaaacucaagccacc-5' | 72 ± 0 | 54 ± 2 | SEQ ID NO:481<br>SEQ ID NO:482 |

As evident from Table 5, the lipophilic 12-dodecanoic acid bisdecylamide group had virtually no effect on gene inhibition efficacy when linked to the 5'-end of the antisense strand, slightly reduced efficacy when linked to the 5'-end of the sense strand, and abolished activity when linked to the 5'-end of both strands. Linking a cholesteryl derivative to the 3'-end of the sense strand and replacing two phosphodiester linkages on the 3'-end of the antisense strand with phosphorothioate linkages only slightly reduced activity.

Example 3
Inhibition of Bcl-2 Gene Expression by RNA Interference in MelJuso Cells To further test the ability of siRNAs bearing nucleotide modifications to inhibit the expression of Bcl-2, a range of differently modified siRNAs specific for Bcl-2, and derived from siRNA B442 above, was tested in MelJuso cells stably transfected with a Bcl-2/GFP-fusion protein. The siRNAs tested bore various combinations of the following modifications: 2'-O-Methyl groups in positions 21 and 22 (counting 5' to 3') of the antisense strand; phosphorothioate linkages between positions 21 and 22 (counting 5' to 3') of the antisense strand; phosphorothioate linkages between the 4 3'-most and the 4 5'-most nucleotides in the sense strand; all linkages replaced by phosphorothioates in the sense or antisense strand; and a cholesteryl derivative linked to the 5'-end of the sense or antisense strand via a phosphorothioate linkage.

Creation of Cell Line Mel Juso-GFP-BCL2

A reporter cell line for estimating the efficacy of siRNAs in inhibiting the expression of BCL2 is constructed by transfecting Mel Juso cells (DSMZ No ACC 74) with a reporter construct from which an mRNA is transcribed encoding an eGFP-BCL2 fusion protein. The efficacy of inhibition may be measured in such cells by comparing the fluorescence intensity of eGFP in such cells after treatment with a siRNA comprising a BCL2 sequence with the fluorescence intensity in such cells treated with a control siRNA.

The open reading frame of human BCL-2 (alpha splice form, GenBank accession number M13994) is PCR-amplified from a human BDTM Marathon-Ready cDNA library (BD Biosciences Clontech, Palo Alto, Calif., USA, Cat. #: 639343) using the BD Advantage HF 2 PCR kit (BD Biosciences Clontech, Palo Alto, Calif., USA Cat. #: 639123). Primer, nucleotide and enzyme concentration are used according to manufacturer's instructions. Amplification is performed in 30 cycles with the following three steps in each cycle: 20 sec. 95° C., 30 sec. 62° C., 60 sec. 72° C. A final step of 120 sec at 72° C. terminates the amplification reaction. Primers are AAA *CTC GAG* GCG CAC GCT GGG AGA ACG GGG (SEQ ID NO:490) (introducing a XhoI (italics) restriction site upstream of the codon coding for amino acid 2 of BCL2) and AAA TCT AGA TCA CTT GTG GCT CAG ATA GGC (SEQ ID NO:491) (introducing a XbaI restriction site (italics) after the BCL2 stop codon (double underlined)). The PCR product is gel-purified on a 0.8% agarose gel, digested with XhoI and XbaI and ligated into pEGFP-C3 (BD Biosciences Clontech, Palo Alto Calif., USA; Cat. #: 632315) digested with XhoI and XbaI. The correct insertion of the cDNA is verified by sequencing. The plasmid is transfected into Mel Juso cells by lipofection with FuGene6 (Roche Cat No. 1814443) and Neomycin-resistant and fluorescing clones are identified in three rounds of: selection in the presence of G418 for 48 h followed by selection of fluorescent cells and replating of single cells using FACS-analysis.

Introduction of siRNAs into Mel Juso-GFP-BCL2-cells and Determination of Gene Expression Inhibition by FACS Analysis Mel Juso-GFP-BCL2-Cells (about 80% confluent) were trypsinized from 96 mm Petri dishes with 5 ml trypsin-EDTA (0.25% Trypsin; 1 mM Na4-EDTA; Gibco/Invitrogen, Karlsruhe, Germany) for 3-5 min at 37° C. 5 ml cell culture medium (DMEM supplemented with 10% FCS and 2500 µg/ml Neomycin, all GBCO BRL, Paisley, UK) were added and cells were centrifuged at 400 g for 5 minutes at room temperature. The cell pellet was resuspended in 250 µl cell culture medium and the cell number per unit volume determined in a Neubauer chamber. The resuspended cells were diluted to a density of 50 000 cells per ml cell culture medium and 2 ml of this suspension were plated into one well of a 6 well plate. Mel Juso cells were seeded 24 h before siRNA treatment to allow adherent cell growth. After 24 h culture medium was removed and cultures were incubated for 4 h with 50 nM siRNA pre-complexed in Opti-MEM medium with Oligofectamin (both from Invitrogen, Carlsbad, USA) according to the manufacturer's protocol. After incubation, the incubation medium was replaced by complete medium and cells were cultivated under standard conditions 37° C. and 5% CO2 for 72 h (Heracell incubator, Kendro Laboratory products GmbH, Langenselbold, Germany).

Cells were harvested by removing the cell culture medium, adding 500 µl trypsin-EDTA (Gibco-Invitrogen GmbH, Karlsruhe, Germany) per well and incubating for 3-5 min at 37° C. 1 ml cell culture medium was added to the trypsin solution and the cells were resuspended. The suspension was transferred to FACS tubes (5 ml, Sarstedt AG & Co., Nümbrecht, Germany) and centrifuged at 400 g for 5 min. Pellets were resuspended in 1 ml PBS (Biochrom, Cambridge, UK) and eGFP-fluorescence was measured by flow-cytometry (FACS Calibur, Becton Dickinson, Franklin Lakes, N.J., USA) 10,000 cells were counted per tube.

TABLE 6

List of siRNAs employed in testing the influence of various modifications of the sense and/or antisense strand on siRNA efficacy in MelJuso cells, and the efficiency of a cholesteryl derivative tethered to one or both strands in facilitating cell entry of siRNAs without transfection aid

| Name | Lipofection | Sequence | Efficacy [%] | Seq. ID |
|---|---|---|---|---|
| AL-DUP-5108 | X | 5'-ggccuucuuugaguucggugg-3'<br>5'-ccaccgaacucaaagaaggccmamc-3' | 49 ± 6% | SEQ ID NO:483<br>SEQ ID NO:484 |
| AL-DUP-5109 | X | 5'-ggccuucuuugaguucggugg-3'<br>5'-ccaccgaacucaaagaaggccmamc-3' | 51 ± 14% | SEQ ID NO:485<br>SEQ ID NO:486 |
| AL-DUP-5110 | X | 5'-ggccuucuuugaguucggugg-3'<br>5'-ccaccgaacucaaagaaggccmamc-3' | 46 ± 12% | SEQ ID NO:485<br>SEQ ID NO:484 |
| AL-DUP-5111 | X | 5'-Chol-ggccuucuuugaguucggugg-3'<br>5'-ccaccgaacucaaagaaggccmamc-3' | 44 ± 3% | SEQ ID NO:487<br>SEQ ID NO:486 |
| AL-DUP-5112 | X | 5'-Chol-ggccuucuuugaguucggugg-3'<br>5'-ccaccgaacucaaagaaggccmamc-3' | 3 ± 2% | SEQ ID NO:488<br>SEQ ID NO:486 |
| AL-DUP-5113 | X | 5'-Chol-ggccuucuuugaguucggugg-3'<br>5'-ccaccgaacucaaagaaggccmamc-3' | -30 ± 14% | SEQ ID NO:488<br>SEQ ID NO:484 |
| AL-DUP-5114 | X | 5'-ggccuucuuugaguucggugg-3'<br>5'-Chol-ccaccgaacucaaagaaggccmamc-3' | -23 ± 1% | SEQ ID NO:483<br>SEQ ID NO:489 |
| AL-DUP-5115 | X | 5'-Chol-ggccuucuuugaguucggugg-3'<br>5'-Chol-ccaccgaacucaaagaaggccmamc-3' | 23 ± 3% | SEQ ID NO:487<br>SEQ ID NO:489 |
| AL-DUP-5116 | X | 5'-Chol-ggccuucuuugaguucggugg-3'<br>5'-Chol-ccaccgaacucaaagaaggccmamc-3' | 32 ± 2% | SEQ ID NO:488<br>SEQ ID NO:489 |
| AL-DUP-5117 | X | 5'-ggccuucuuugaguucggugg-3'<br>5'-Chol-ccaccgaacucaaagaaggccmamc-3' | -22 ± 2% | SEQ ID NO:485<br>SEQ ID NO:489 |
| AL-DUP-5121 | X | 5'-ggccuucuuugaguucggugg-3'<br>5'-ccaccgaacucaaagaaggccmamc-3' | 66 ± 11% | SEQ ID NO:483<br>SEQ ID NO:486 |
| AL-DUP-5110 | | 5'-ggccuucuuugaguucggugg-3'<br>5'-ccaccgaacucaaagaaggccmamc-3' | -2 ± 3% | SEQ ID NO:485<br>SEQ ID NO:484 |
| AL-DUP-5112 | | 5'-Chol-ggccuucuuugaguucggugg-3'<br>5'-ccaccgaacucaaagaaggccmamc-3' | 17 ± 1% | SEQ ID NO:488<br>SEQ ID NO:486 |
| AL-DUP-5113 | | 5'-Chol-ggccuucuuugaguucggugg-3'<br>5'-ccaccgaacucaaagaaggccmamc-3' | 15 ± 2% | SEQ ID NO:488<br>SEQ ID NO:484 |
| AL-DUP-5114 | | 5'-ggccuucuuugaguucggugg-3'<br>5'-Chol-ccaccgaacucaaagaaggccmamc-3' | 13 ± 1% | SEQ ID NO:483<br>SEQ ID NO:489 |
| AL-DUP-5115 | | 5'-Chol-ggccuucuuugaguucggugg-3'<br>5'-Chol-ccaccgaacucaaagaaggccmamc-3' | 13 ± 2% | SEQ ID NO:487<br>SEQ ID NO:489 |
| AL-DUP-5116 | | 5'-Chol-ggccuucuuugaguucggugg-3'<br>5'-Chol-ccaccgaacucaaagaaggccmamc-3' | 16 ± 1% | SEQ ID NO:485<br>SEQ ID NO:489 |

As is evident from Table 6, the modification of nucleotides with phosphorothioate linkages in the backbone was generally well tolerated, as were 2'-O-methyl modifications of nucleotides located near the 3'-terminus of the sense strand. The results obtained using this assay with cholesteryl-derivative modified siRNAs AL-DUP-5112 through AL-DUP-5117 are somewhat inconclusive when lipofection is employed to facilitate entry of the siRNA into the cell. However, we have observed in the past that lipofection agents in connection with phosphorothioate- and/or cholesteryl-modified oligonucleotides can sometimes give rise to experimental artifacts (data not shown). It should therefore not be concluded that the 5'-cholesteryl modification abolishes siRNA activity. In addition, from those results obtained with the same siRNAs in the absence of lipofection agent, it is clear that the cholesteryl modification allows entry of the siRNAs into cells in a setting that is more relevant to the situation encountered within the body of an animal, e.g. a human, namely the absence of high concentrations of a lipofection agent. AL-DUP-5110, which is identical to AL-DUP-5114 except for the cholesteryl-derivative ligand, did not have any effect when incubated with cells without lipofection agent, while AL-DUP-5114 inhibited bcl-2 expression under these circumstances.

Example 4

Inhibition of Bcl-2 Gene Expression by RNA Interference in Human Pancreatic Cancer YAP C Cells The cells of the human pancreatic Yap C cancer line (German Microorganism and Cell Culture Collection, Braunschweig, (No. ACC 382)), were cultured at 37° C., 5% $CO_2$ in RPMI 1640 medium (Biochrom Corp., Berlin) with 10% fetal calf serum (FCS) and 1% penicillin/streptomycin. Human skin fibroblasts were cultured under the same conditions in Dulbecco's MEM with 10% FCS and 1% penicillin/streptomycin.

The double-stranded oligoribonucleotides used for transfection have the following sequences, designated as SEQ ID No:1 to SEQ ID No:6 in the sequence protocol:

dsRNA 1, which is complementary to a first sequence of the human Bcl-2 gene:

```
S2: 5'- caggaccucgccgcugcagacc-3'    (SEQ ID NO: 1)

S1: 3'-cgguccuggagcggcgacgucugg-5'   (SEQ ID NO: 2)
``` dsRNA 2, which is complementary to a second sequence of the human Bcl-2 gene:

```
S2: 5'- gccuuguggaacuguacggcc-3'    (SEQ ID NO: 3)

S1: 3'-uacggaaacaccuugacaugccgg-5'  (SEQ ID NO: 4)
``` dsRNA 3, which is complementary to a sequence of the neomycin resistance gene:

```
S2: 5'- caaggaugaggaucguuucgca-3'   (SEQ ID NO: 5)

S1: 3'-ucuguccuacuccuagcaaagcg -5'  (SEQ ID NO: 6)
```

Transfection was carried out in a 6-well plate with oligofectamine (Invitrogen Corp., Karlsruhe). 250,000 cells were placed in each well. Transfection of the double-stranded oligoribonucleotides was carried out in accordance with the oligofectamine protocol recommended by Invitrogen (the data relate to 1 well of a 6-well plate):

10 μl of the double-stranded oligoribonucleotides (0.1-10 μM) were diluted with 175 μl cell culture medium without additives. 3 μl oligofectamine were diluted with 12 μl cell culture medium without additives, and incubated for 10 minutes at room temperature. The diluted oligofectamine was then added to the diluted double-stranded oligoribonucleotides, mixed, and incubated for 20 minutes at room temperature. During this time, the cells to be transfected were washed once with cell culture medium without additives, and 800 μl of fresh cell culture medium was added so that the transfection end volume was 1000 μl. This results in a double-stranded oligoribonucleotide end concentration of 1-100 μM. The transfection media was incubated with the cells for four hours at 37 IC. 500 μl of cell culture medium with 30% FCS were then placed in each well, i.e. final concentration of FCS was 10%. The cells were then incubated for 120 hours at 37° C., at which time they were washed with phosphate buffered saline (PBS), trypsinized and centrifuged for 10 minutes at 100 g. The supernatant fluid was discarded, and the pellet was incubated in the dark with hypotonic propidium iodide solution for 30 minutes at 4° C. The pelletted cells were then analyzed by flow cytometry using a FACSCalibur fluorescence-activated cell sorter (BD GmbH, Heidelberg).

Figure 2:
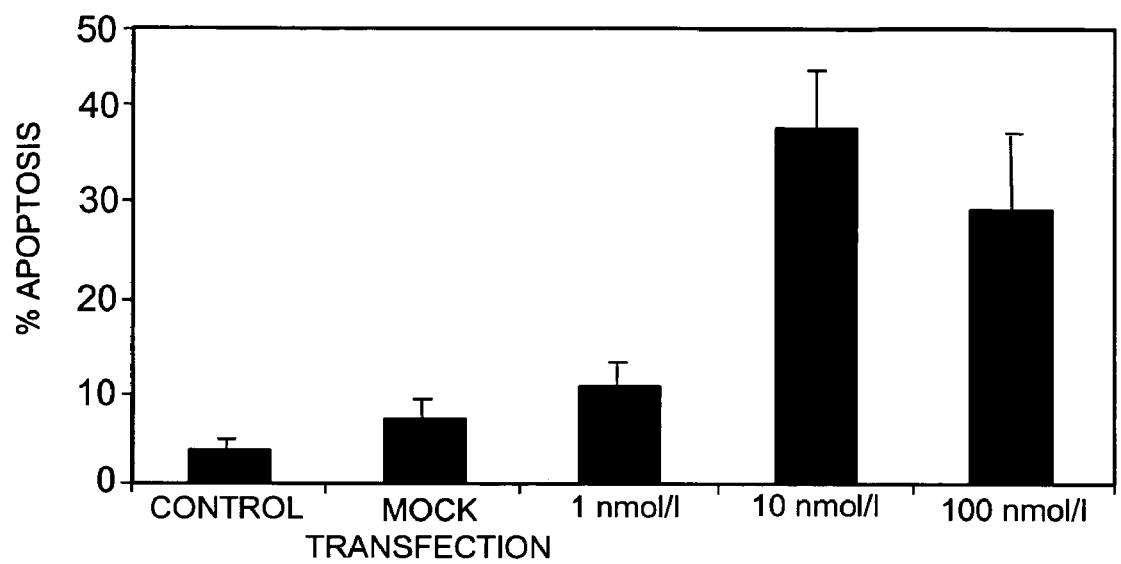
FIG. 2 shows the apoptosis rate (percent) of YAP C cells, 120 hours after transfection with dsRNA 2 that is complementary to a first sequence of the human Bcl-2 gene.
Figure 3:
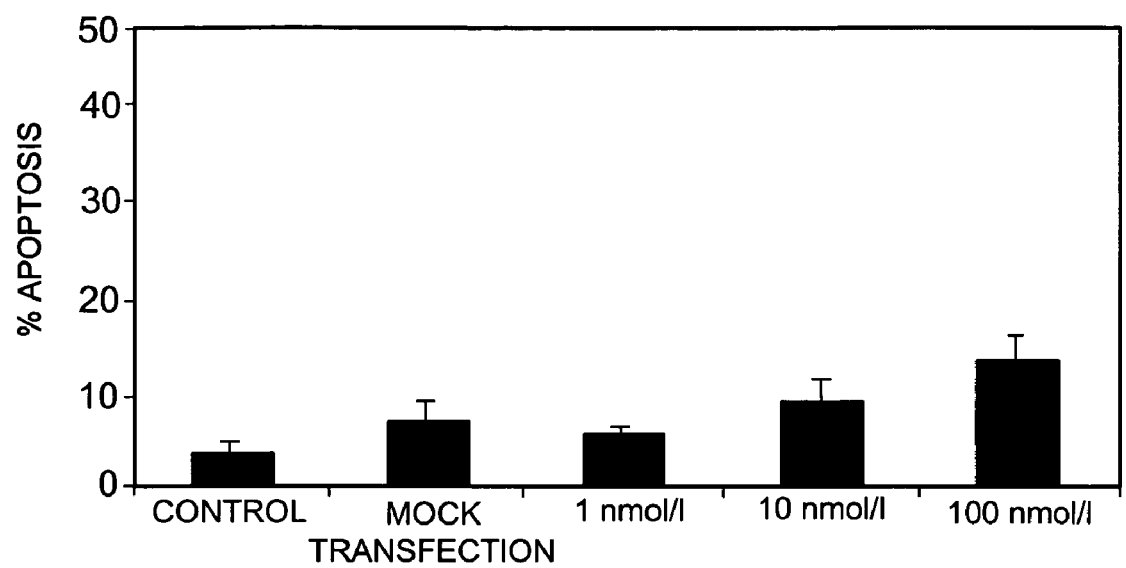
FIG. 3 shows the apoptosis rate (percent) of YAP C cells, 120 hours after transfection with dsRNA 3 that is complementary to a sequence of the neomycin resistance gene.

Both the double-stranded oligoribonucleotides dsRNA 1 and dsRNA 2 decreased the inhibition of apoptosis mediated by Bcl-2 in the human pancreatic cancer cells studied. No additional stimulation of apoptosis was required to induce or initiate apoptosis. The apoptosis rate rose independent of incubation time. FIG. 1 shows the result achieved with dsRNA 1 and FIG. 2 that with dsRNA 2. Whereas untreated YAP C control cells and cells with which the described methods of transfection were carried out without double-stranded oligoribonucleotides (mock-transfected cells) showed an apoptosis rate of only 3.8% and 7.1% after 120 hours incubation, the apoptosis rate achieved with 100 nM dsRNA rose to 37.2% for transfection with dsRNA 1 and 28.9% for transfection with dsRNA 2. Control transfection with dsRNA 3 led to a maximum apoptosis rate of 13.5%. This represents no significant increase when compared to mock-transfected cells, and proves the sequence specificity of the action of the dsRNA 1 and dsRNA 2. As a control, skin fibroblasts were transfected as non-transformed cells with dsRNA 1 and dsRNA 2. After 120 hours, these cells showed no significant increase in apoptosis rate.

Example 5

Treatment of a Pancreatic Cancer Patient with dsRNA 1 and 2

In this Example, dsRNA 1 and 2 are injected into a pancreatic cancer patient and shown to specifically inhibit Bcl-2 gene expression.

Synthesis and Preparation of dsRNAs dsRNA 1 and 2 directed against the Bcl-2 gene are chemically synthesized with or without a hexaethylene glycol linker. Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 nm (Dionex Corp.; low salt buffer: 20 mM Tris, 10 mM $NaClO_4$, pH 6.8, 10% acetonitrile; the high-salt buffer was: 20 mM Tris, 400 mM $NaClO_4$, pH 6.8, 10% acetonitrile. flow rate: 3 ml/min). Formation of double-stranded dsRNAs is then achieved by heating a stoichiometric mixture of the individual antisense strands (10 µM) in 10 mM sodium phosphate buffer, pH 6.8, 100 mM NaCl, to 80-90° C., with subsequent slow cooling to room temperature over 6 hours.

In addition, dsRNA molecules with linkers may be produced by solid phase synthesis and addition of hexaethylene glycol as a non-nucleotide linker (Jeremy, D., et al., *Biochem.* (1996), 35:14665-14670). A hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

dsRNA Administration and Dosage

The present example provides for pharmaceutical compositions for the treatment of human pancreatic cancer patients comprising a therapeutically effective amount of a dsRNA 1 and dsRNA 2 as disclosed herein, in combination with a pharmaceutically acceptable carrier or excipient. dsRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare dsRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa. (1980).

RNA Purification and Analysis

Efficacy of the dsRNA treatment is determined at defined intervals after the initiation of treatment using real time PCR on total RNA extracted from tissue biopsies. Cytoplasmic RNA from tissue biopsies, taken prior to and during treatment, is purified with the help of the RNeasy Kit (Qiagen, Hilden) and Bcl-2 mRNA levels are quantitated by real time RT-PCR as described previously (Eder, M., et al., *Leukemia* (1999) 13:1383-1389; Scherr, M., et al., *BioTechniques* (2001) 31:520-526). Analysis of Bcl-2 mRNA levels before and during treatment by real time PCR, provides the attending physician with a rapid and accurate assessment of treatment efficacy as well as the opportunity to modify the treatment regimen in response to the patient's symptoms and disease progression.

Example 6 dsRNA Expression Vectors

In another aspect of the invention, Bcl-2 specific dsRNA molecules that interact with Bcl-2 target RNA molecules and modulate Bcl-2 gene expression activity are expressed from transcription units inserted into DNA or RNA vectors (see, e.g., Couture, A, et al., *TIG.* (1996), 12:5-10; Skillem, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19 ; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single target gene or multiple target genes over a period of a week or more are also contemplated by the present invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The dsRNA 1 and 2 molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 7

Method of Determining an Effective Dose of a dsRNA

A therapeutically effective amount of a composition containing a sequence that encodes Bcl-2 specific dsRNA, (i.e., an effective dosage), is an amount that inhibits expression of the polypeptide encoded by the Bcl-2 target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the dsRNA may be desired. When an inducible promoter is included in the construct encoding an dsRNA, expression is assayed upon delivery to the subject of an appropriate dose of the substance used to induce expression.

Appropriate doses of a composition depend upon the potency of the molecule (the sequence encoding the dsRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the Bcl-2 target gene mRNA (e.g. using real time PCR) or the amount of polypeptide encoded by the target gene mRNA (Western blot analysis). In addition, the attending physician will monitor the symptoms associated with pancreatic cancer afflicting the patient and compare with those symptoms recorded prior to the initiation of dsRNA treatment.

I claim:

1. An isolated double-stranded ribonucleic acid (dsRNA), wherein said dsRNA comprises a sense strand consisting of SEQ ID NO: 29 and an antisense strand consisting of SEQ ID NO: 30, wherein said dsRNA is 21 to 30 nucleotides in length.

2. The dsRNA of claim 1, wherein said dsRNA comprises at least one modified nucleotide.

3. The dsRNA of claim 2, wherein said modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.

4. The dsRNA of claim 2, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

5. A cell comprising the dsRNA of claim 1.

* * * * *